US007186719B2

(12) United States Patent
Pratt et al.

(10) Patent No.: US 7,186,719 B2
(45) **Date of Patent: *Mar. 6, 2007**

(54) ANTIBACTERIAL AGENTS

(75) Inventors: Lisa Marie Pratt, Cowley (GB); Kenneth Noel Keavey, Cowley (GB); Gilles Denis Pain, Cowley (GB); Laurent Mounier, Cowley (GB)

(73) Assignee: British Biotech Pharmaceuticals (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/953,788

(22) Filed: Sep. 30, 2004

(65) Prior Publication Data

US 2005/0065095 A1 Mar. 24, 2005

Related U.S. Application Data

(62) Division of application No. 10/049,131, filed as application No. PCT/GB00/03078 on Aug. 10, 2000, now Pat. No. 6,846,825.

(30) Foreign Application Priority Data

Aug. 10, 1999 (GB) ................................ 9918869.0
Nov. 16, 1999 (GB) ................................ 9927093.6

(51) Int. Cl.
*C07D 401/12* (2006.01)
*C07D 401/14* (2006.01)
*C07D 405/10* (2006.01)
*A61K 31/4427* (2006.01)
*A61P 31/04* (2006.01)

(52) U.S. Cl. .................. 514/235.5; 546/188; 546/193; 546/196; 546/207; 546/214; 546/221; 544/129; 544/133; 514/237.2; 514/256; 514/337; 514/318; 514/336; 514/320

(58) Field of Classification Search ................ 546/188, 546/193, 194, 196, 207, 214, 221; 544/129, 544/133; 514/237.2, 235.5, 256, 337, 318, 514/336, 320
See application file for complete search history.

(56) References Cited

U.S. PATENT DOCUMENTS 6,787,522 B2 * 9/2004 Hunter et al. ................. 514/19

FOREIGN PATENT DOCUMENTS

| | | |
|---|---|---|
| JP | 08053403 | 2/1996 |
| WO | 91/02716 | 3/1991 |
| WO | 99/39704 | 8/1999 |
| WO | 99/57097 | 11/1999 |

OTHER PUBLICATIONS

Broughton, et al.: “Studies Concerning the Antibiotic Actinonin”, J. Chem. Soc., Perkin Trans 1, vol. 9, 1975, pp. 857-860, XP002157880, XP002157880.

Devlin, John P., et al: “Antibiotic actinonin, V. Synthesis of structural analogs of actinonin b the anhydride-ester method”, J.Chem. Soc., Perkin Trans. 1 (1975),(9), 846-848, XP002157881.

Penning, Thomas D., et al.: “Kelatorphan and related analogs: potent and selective inhibitors of leukotriene A4 hydrolase”, Bioorg. Med. Chem. Lett. (1995), 5(21), 2157-2522,XP002157882.

Chen, et al.: “Actinonin, a naturally occurring antibacterial agent, is a potent deformylase inhibitor”, BIOCHEMISTRY, vol. 39, Feb. 15, 2000, pp. 1256-1262, XP002158085.

Inaoka, et al.: “Propioxatins A and B, new enkephalinase B inhibitors”, J.Biochem. (Tokyo), vol. 104, 1988, pp. 706-711, XP000978993, table I, compd 4.

Bouboutou, et al.: “Inhibition of porcine synovial collengenase by actinonin and derivatives” Colloq. Inserm., vol. 174, 1989, pp. 341-344, XP000978992, Table I, Actinonin 2.

Inaoka, et al.: “propioxatins A and B, new enkephalinase B inhibitors”, J. Antiobiot., vol. 39, No. 10, 1986, pp. 1382-1385, XP000978947.

* cited by examiner

*Primary Examiner*—Kahsay Habte
(74) *Attorney, Agent, or Firm*—Banner & Witcoff, Ltd.

(57) ABSTRACT

Compounds of formula (II) are antibacterial agents wherein Q represents a radical of the formula: —N(OH)CH(═O) or the formula: —C(═O)NH(OH); $R_1$ represents hydrogen, $C_1$–$C_6$ alkyl or $C_1$–$C_6$ alkyl substituted by one or more halogen atoms, or, except when Q is a radical of the formula: —N(OH)CH(═O), a hydroxy, $C_1$–$C_6$ alkoxy, $C_1$–$C_6$ alkenyloxy, amino, $C_1$–$C_6$ alkylamino, or di-($C_1$–$C_6$ alkyl) amino group; $R_2$ represents a substituted or unsubstituted $C_1$–$C_6$ alkyl, cycloalkyl($C_1$–$C_6$ alkyl)- or aryl($C_1$–$C_6$ alkyl)-group; and A represents a group of formula (IIA), or (IIB) wherein $R_4$ represents the side chain of a natural or non-natural alpha amino acid, and $R_5$ and $R_6$ when taken together with the nitrogen atom to which they are attached form a saturated heterocyclic first ring of 5 to 7 atoms as specified in the description.

18 Claims, No Drawings

ANTIBACTERIAL AGENTS

This application is a divisional of U.S. Ser. No. 10/049,131 filed Feb. 8, 2002, now U.S. Pat. No. 6,846,825, issued on Jan. 25, 2005, which is a U.S. National Phase Application Under 35 USC 371 of PCT/GB00/03078, filed Aug. 20, 2000. Each of these applications is hereby incorporated by reference in its entirety. Applicants herewith claim the benefit of PCT/GB00/03078 filed Aug. 10, 2000, which was published Under PCT Article 21(2) in English on Feb. 12, 2001 and Great Britain Application No. 9918869.0 filed Aug. 10, 1999 and Great Britain Application No. 9927093.6 filed Nov. 16, 1999.

This invention relates to novel hydroxamic acid and N-formyl hydroxylamine derivatives having antibacterial activity, to methods of treatment using such compounds, and to pharmaceutical and veterinary compositions comprising such compounds.

BACKGROUND OF THE INVENTION

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those which have mechanisms of action fundamentally different from the known classes.

Amongst the Gram-positive pathogens, such as *Staphylococci, Streptococci, Mycobacteria* and *Enterococci*, resistant strains have evolved/arisen which makes them particularly difficult to eradicate. Examples of such strains are methicillin resistant *Staphylococcus aureus* (MRSA), methicillin resistant coagulase negative *Staphylococci* (MRCNS), penicillin resistant *Streptococcus pneumoniae* and multiply resistant *Enterococcus faecium.*

Pathogenic bacteria are often resistant to the aminoglycoside, β-lactam (penicillins and cephalosporins), and chloramphenicol types of antibiotic. This resistance involves the enzymatic inactivation of the antibiotic by hydrolysis or by formation of inactive derivatives. The β-lactam (penicillin and cephalosporin) family of antibiotics are characterised by the presence of a β-lactam ring structure. Resistance to this family of antibiotics in clinical isolates is most commonly due to the production of a "penicillinase" (β-lactamase) enzyme by the resistant bacterium which hydrolyses the β-lactam ring thus eliminating its antibacterial activity.

Recently there has been an emergence of vancomycin-resistant strains of enterococci (Woodford N. 1998 Glycopeptide-resistant enterococci: a decade of experience. Journal of Medical Microbiology. 47(10):849-62). Vancomycin-resistant enterococci are particularly hazardous in that they are frequent causes of hospital based infections and are inherently resistant to most antibiotics. Vancomycin works by binding to the terminal D-Ala-D-Ala residues of the cell wall peptidioglycan precursor. The high-level resistance to vancomycin is known as VanA and is conferred by a genes located on a transposable element which alter the terminal residues to D-Ala-D-lac thus reducing the affinity for vancomycin.

In view of the rapid emergence of multidrug-resistant bacteria, the development of antibacterial agents with novel modes of action that are effective against the growing number of resistant bacteria, particularly the vancomycin resistant *enterococci* and β-lactam antibiotic-resistant bacteria, such as methicillin-resistant *Staphylococcus aureus*, is of utmost importance.

BRIEF DESCRIPTION OF THE INVENTION

This invention is based on the finding that certain hydroxamic acid and N-formyl hydroxylamine derivatives have antibacterial activity, and makes available a new group of antibacterial agents. It has been found that the compounds with which this invention is concerned are antibacterial with respect to a range of bacteria, with potency against Gram-positive organisms generally being greater than against Gram-negatives. Many of the compounds of the invention show activity against bacteria responsible for respratory infections, such as *Streptococcus pneumoniae* and *Haemophilus influenzae.*

Although it may be of interest to establish the mechanism of action of the compounds with which the invention is concerned, it is their ability to inhibit bacterial growth that makes them useful. However, it is presently believed that their antibacterial activity is due, at least in part, to intracellular inhibition of bacterial polypeptide deformylase (PDF; EC 3.5.1.31).

All ribosome-mediated synthesis of proteins starts with a methionine residue. In prokaryotes the methionyl moiety carried by the initiator tRNA is N-formylated prior to its incorporation into a polypeptide. Consequently, N-formylmethionine is always present at the N-terminus of a nascent bacterial polypeptide. However, most mature proteins do not retain the N-formyl group or the terminal methionine residue. Deformylation is required prior to methionine removal, since methionine aminopeptidase does not recognise peptides with an N-terminal formylmethionine residue (Solbiati et al., J. Mol. Biol. 290:607–614, 1999). Deformylation is, therefore, a crucial step in bacterial protein biosynthesis and the enzyme responsible, PDF, is essential for normal bacterial growth. Although the gene encoding PDF (def) is present in all pathogenic bacteria for which sequences are known (Meinnel et al., J. Mol. Biol, 266:939–49, 1997), it has no eukaryotic counterpart, making it an attractive target for antibacterial chemotherapy.

The isolation and characterisation of PDF has been facilitated by an understanding of the importance of the metal ion in the active site (Groche et al., Biophys. Biochem. Res. Commun., 246:324–6, 1998). The $Fe^{2+}$ form is highly active in vivo but is unstable when isolated due to oxidative degradation (Rajagopalan et al., J. Biol. Chem. 273:22305–10, 1998). The $Ni^{2+}$ form of the enzyme has specific activity comparable with the ferrous enzyme but is oxygen-insensitive (Ragusa et al., J. Mol. Biol. 1998, 280: 515–23, 1998). The $Zn^{2+}$ enzyme is also stable but is almost devoid of catalytic activity (Rajagopalan et al., J. Am. Chem. Soc. 119:12418–12419, 1997).

Several X-ray crystal structures and NMR structures of *E. coli* PDF, with or without bound inhibitors, have been published (Chan et al., Biochemistry 36:13904–9, 1997; Becker et al., Nature Struct. Biol. 5:1053–8, 1998; Becker et al., J. Biol. Chem. 273:11413–6, 1998; Hao et al., Biochemistry, 38:4712–9, 1999; Dardel et al., J. Mol. Biol. 280: 501–13, 1998; O'Connell et al., J. Biomol. NMR, 13:311–24, 1999), indicating similarities in active site geometry to metalloproteinases such as thermolysin and the metzincins.

Recently the substrate specificity of PDF has been extensively studied (Ragusa et al., J. Mol. Biol. 289:1445–57, 1999; Hu et al., Biochemistry 38:643–50, 1999; Meinnel et al., Biochemistry, 38:4287–95, 1999). These authors conclude that an unbranched hydrophobic chain is preferred at P1', while a wide variety of P2' substituents are acceptable and an aromatic substituent may be advantageous at the P3' position. There have also been reports that small peptidic compounds containing an H-phosphonate (Hu et al., Bioorg. Med. Chem. Lett., 8:2479–82, 1998) or thiol (Meinnel et al., Biochemistry, 38:4287–95, 1999) metal binding group are micromolar inhibitors of PDF. Peptide aldehydes such as calpeptin (N-Cbz-Leu-norleucinal) have also been shown to inhibit PDF (Durand et al., Arch. Biochem. Biophys., 367: 297–302, 1999). However, the identity of the metal binding group and its spacing from the rest of the molecule ("recognition fragment") has not been studied extensively. Furthermore, non-peptidic PDF inhibitors, which may be desirable from the point of view of bacterial cell wall permeability or oral bioavailability in the host species, have not been identified.

RELATED PRIOR ART

Certain N-formyl hydroxylamine derivatives have previously been claimed in the patent publications listed below, although very few examples of such compounds have been specifically made and described:

| | |
|---|---|
| EP-B-0236872 | (Roche) |
| WO 92/09563 | (Glycomed) |
| WO 92/04735 | (Syntex) |
| WO 95/19965 | (Glycomed) |
| WO 95/22966 | (Sanofi Winthrop) |
| WO 95/33709 | (Roche) |
| WO 96/23791 | (Syntex) |
| WO 96/16027 | (Syntex/Agouron) |
| WO 97/03783 | (British Biotech) |
| WO 97/18207 | (DuPont Merck) |
| WO 98/38179 | (GlaxoWellcome) |
| WO 98/47863 | (Labs Jaques Logeais) |

The pharmaceutical utility ascribed to the N-formyl hydroxylamine derivatives in those publications is the ability to inhibit matrix metalloproteinases (MMPs) and in some cases release of tumour necrosis factor (TNF), and hence the treatment of diseases or conditions mediated by those enzymes, such as cancer and rheumatoid arthritis.

In addition to these, U.S. Pat. No. 4,738,803 (Roques et al.) also discloses N-formyl hydroxylamine derivatives, however, these compounds are disclosed as enkephalinase inhibitors and are proposed for use as antidepressants and hypotensive agents. Also, WO 97138705 (Bristol-Myers Squibb) discloses certain N-formyl hydroxylamine derivatives as enkephalinase and angiotensin converting enzyme inhibitors.

Our copending International Patent Application No. WO 99/39704 describes and claims, inter alia, the use of a compound of formula (I) or a pharmaceutically or veterinarily acceptable salt thereof in the preparation of an antibacterial composition:

(I)

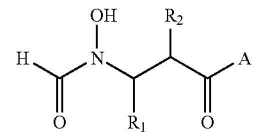

wherein $R_1$ represents hydrogen, $C_1$–$C_6$ alkyl or $C_1$–$C_6$ alkyl substituted by one or more halogen atoms; $R_2$ represents a substituted or unsubstituted $C_1$–$C_6$ alkyl, cycloalkyl($C_1$–$C_6$ alkyl) or aryl($C_1$–$C_6$ alkyly group; and A represents a group of formula (IA), or (IB):

(IA)

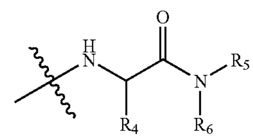

(IB)

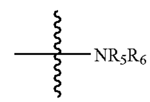

wherein $R_4$ represents the side chain of a natural or non-natural alpha amino acid, and $R_5$ and $R_6$ when taken together with the nitrogen atom to which they are attached form an optionally substituted saturated heterocyclic ring of 3 to 8 atoms which ring is optionally fused to a carbocyclic or second heterocyclic ring.

Very many hydroxamic acid derivatives are known. Many have been disclosed as having matrix metalloproteinase (MMP) inhibitory activity, and thus to be potentially useful for the treatment of diseases mediated by MMPs, for example cancer, arthritides, and conditions involving tissue remodeling such as wound healing, and restenosis. In addition our International Patent Application No. WO 99/59568 describes the use of analogues of the N-formylhydroxylamine derivatives of WO 99/39704 (wherein the N-formylhydroxylamine group is replaced by a hydroxamic acid group) in the preparation of an antibacterial composition.

BRIEF DESCRIPTION OF THE INVENTION

This invention relates to a group of antibacterially active hydroxamic acid and and N-formyl hydroxylamine compounds which differ in structure from those of International Patent Applications Nos. WO 99/59568 and WO 99/39704, principally in the nature of the —$NR_5R_6$ group (see formulae (I), (IA) and (IB) above and the hydroxamic acid analogues thereof). In those applications, the term "optionally substituted" as used in relation to the saturated heterocyclic ring formed by $R_5$, $R_6$ and the nitrogen to which they are attached is defined as meaning certain specific substituents. In the present compounds, the group —$NR_5R_6$ is also an optionally substituted saturated heterocyclic ring of 3 to 8 atoms which ring is optionally fused to a carbocyclic or second heterocyclic ring, but the substituents are different from those permitted by WO 99/59568 and WO 99/39704. The group —$NR_5R_6$ of the N-formyl hydroxylamines and hydroxamic acids of the invention is also believed to distinguish the present compounds from those known in the MMP, TNF, ACE, and enkephalinase inhibitor art.

DETAILED DESCRIPTION OF THE INVENTION

The present invention provides a compound of formula (II), or a pharmaceutically or veterinarily acceptable salt, hydrate or solvate thereof (II)

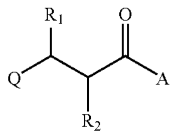

wherein

Q represents a radical of formula —N(OH)CH(═O) or formula —C(═O)NH(OH);

$R_1$ represents hydrogen, $C_1$–$C_6$ alkyl or $C_1$–$C_6$ alkyl substituted by one or more halogen atoms, or, except when Q is a radical of formula —N(OH)CH(═O), a hydroxy, $C_1$–$C_6$ alkoxy, $C_1$–$C_6$ alkenyloxy, amino, $C_1$–$C_6$ alkylamino, or di-($C_1$–$C_6$ alkyl)amino group;

$R_2$ represents a substituted or unsubstituted $C_1$–$C_6$ alkyl, cycloalkyl($C_1$–$C_6$ alkyl) or aryl($C_1$–$C_6$ alkyl) group;

and A represents a group of formula (IIA), or (IIB):

(IA)

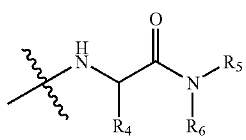

(IB)

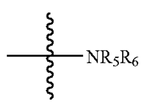

wherein $R_4$ represents the side chain of a natural or non-natural alpha amino acid, and $R_5$ and $R_6$ when taken together with the nitrogen atom to which they are attached form a saturated heterocyclic first ring of 5 to 7 atoms which is optionally fused to a saturated or unsaturated carbocyclic or heterocyclic second ring of 5 to 7 atoms; characterised in that (a) the said second ring is substituted by ($C_1$–$C_6$)alkyl, ($C_2$–$C_6$)alkenyl, ($C_2$–$C_6$)alkynyl, ($C_1$–$C_6$)alkoxy, hydroxy, mercapto, ($C_1$–$C_6$)alkylthio, halo, amino, trifluoromethyl, oxo, nitro, —COOH, —$CONH_2$—$COR^A$, —$COOR^A$, —$NHCOR^A$, —$CONHR^A$, —$NHR^A$, —$NR^AR^B$, or —$CONR^AR^B$ wherein $R^A$ and $R^B$ are independently a ($C_1$–$C_6$)alkyl group; and/or (b) the said first or second ring is substituted by a group of formula (IIC), provided that-the first ring is not substituted by phenoxy, benzyl or benzyl substituted by ($C_1$–$C_6$) alkyl, ($C_1$–$C_6$)alkoxy, phenoxy, hydroxy, mercapto, ($C_1$–$C_6$)alkylthio, amino, halo, trifluoromethyl, nitro, —COOH, —$CONH_2$—$COR^A$, —$COOR^A$, —$NHCOR^A$, —$CONHR^A$, —$NHR^A$, —$NR^AR^B$, or —$CONR^AR^B$ wherein $R^A$ and $R^B$ are independently a ($C_1$–$C_8$)alkyl group, (IIC)

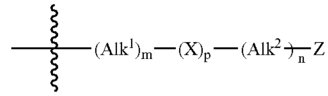

wherein m, p and n are independently 0 or 1;

Z represents, a hydroxy group, or a phenyl or heterocyclic ring of 5 to 7 atoms which is optionally fused to a saturated or unsaturated carbocyclic or heterocyclic second ring of 5 to 7 atoms $Alk^1$ and $Alk^2$ independently represent divalent $C_1$–$C_3$ alkylene radicals;

X represents —O—, —S—, —S(O)—, —S($O_2$)—, —C(═O)—, —NH—, —$NR_7$— where $R_7$ is $C_1$–$C_3$ alkyl;

and wherein $Alk^1$, $Alk^2$ and Z when Z is not a hydroxy group independently are optionally substituted by
- ($C_1$–$C_6$)alkyl, ($C_2$–$C_6$)alkenyl, or ($C_2$–$C_6$)alkynyl,
- phenyl, or halophenyl,
- trifluoromethyl,
- monocyclic 5 or 6membered hetrocyclic,
- benzyl, or halophenylmethyl,
- hydroxy, phenoxy, ($C_1$–$C_6$)alkoxy, or hydroxy($C_1$–$C_6$) alkyl,
- mercapto, ($C_1$–$C_6$)alkylthio or mercapto($C_1$–$C_6$)alkyl,
- oxo,
- nitro,
- cyano (—CN)
- halo (bromo, chloro, fluoro, or iodo)
- —COOH, or —$COOR^A$,
- —$CONH_2$, —$CONHR^A$, or —$CONR^AR^B$
- —$COR^A$, —$SO_2R^A$,
- —$NHCOR^A$,
- —$NH_2$, —$NHR^A$, or —$NR^AR^B$,
  - wherein $R^A$ and $R^B$ are independently a ($C_1$–$C_8$) alkyl group, $R^A$ and $R^B$ taken together with the nitrogen atom to which they are attached form a 5- or 6-membered heterocyclic ring which may be substituted by ($C_1C_3$)alkyl, hydroxy, or hydroxy($C_1$–$C_3$)alkyl.

A subset of compounds of the invention consists of those of formula (II) as defined above wherein:

(a) the said second ring is substituted by ($C_1$–$C_6$)alkyl, ($C_{2-C6}$)alkenyl, ($C_{2-C6}$)alkynyl, ($C_1$–$C_6$)alkoxy, hydroxy, mercapto, ($C_1$–$C_6$)alkylthio, amino, trifluoromethyl, oxo, nitro, —COOH, —$CONH_2$, —$COR^A$, —$COOR^A$, —$NHCOR^A$, —$CONHR^A$, —$NHR^A$, —$NR^AR^B$, or —$CONR^AR^B$ wherein $R^A$ and $R^B$ are independently a ($C_1$–$C_6$) alkyl group; and/or (b) the said first or second ring is substituted by a group of formula (IIC), provided that the first ring is not substituted by phenoxy, benzyl or benzyl substituted by ($C_1$–$C_6$) alkyl, ($C_1$–$C_6$)alkoxy, phenoxy, hydroxy, mercapto, ($C_1$–$C_6$)alkylthio, amino, halo, trifluoromethyl, nitro, —COOH, —$CONH_2$, —$COR^A$, —$COOR^A$, —$NHCOR^A$, —$CONHR^A$, —$NHR^A$, —$NR^AR$ , or —$CONR^AR^B$ wherein $R^A$ and $R^B$ are independently a ($C_1$–$C_6$)alkyl group, (IIC)

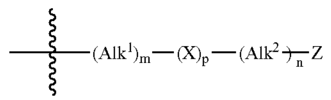

wherein m, p and n are independently 0 or 1;

Z represents, a hydroxy group, or a phenyl or heterocyclic ring of 5 to 7 atoms which is optionally fused to a saturated or unsaturated carbocyclic or heterocyclic second ring of 5 to 7 atoms $Alk^1$ and $Alk^2$ independently represent divalent $C_1$–$C_3$ alkylene radicals;

X represents —O—, —S—, —S(O)—, —$S(O_2)$—, —C(═O)—, —NH—, —$NR_7$— where $R_7$ is $C_1$–$C_3$ alkyl;

and wherein $Alk^1$, $Alk^2$ and Z when Z is not a hydroxy group independently are optionally substituted by ($C_1$–$C_6$)alkyl, ($C_2$–$C_6$)alkenyl, or ($C_2$–$C_6$)alkynyl, phenyl, or halophenyl, trifluoromethyl, monocyclic 5 or 6-membered hetrocyclic, benzyl, hydroxy, phenoxy, or ($C_1$–$C_6$)alkoxy, mercapto, or ($C_1$–$C_6$)alkylthio, oxo, nitro, —COOH, or —$COOR^A$, —$CONH_2$, —$CONHR^A$, or —$CONR^AR^B$

—$COR^A$,

—$NHCOR^A$,

—$NH_2$, —$NHR^A$, or —$NR^AR^B$, wherein $R^A$ and $R^B$ are independently a ($C_1$–$C_6$) alkyl group, In another aspect, the invention provides a method for the treatment of bacterial infections in humans and non-human mammals, which comprises administering to a subject suffering such infection an antibacterially effective dose of a compound of formula (II) as defined above.

In a further aspect of the invention there is provided a method for the treatment of bacterial contamination by applying an antibacterially effective amount of a compound of formula (II) as defined above to the site of contamination.

The compounds of formula (II) as defined above may be used as component(s) of antibacterial cleaning or disinfecting materials.

On the hypothesis that the compounds (II) act by inhibition of intracellular PDF, the most potent antibacterial effect may be achieved by using compounds which efficiently pass through the bacterial cell wall. Thus, compounds which are highly active as inhibitors of PDF in vitro and which penetrate bacterial cells are preferred for use in accordance with the invention. It is to be expected that the antibacterial potency of compounds which are potent inhibitors of the PDF enzyme in vitro, but are poorly cell penetrant, may be improved by their use in the form of a prodrug, ie a structurally modified analogue which is converted to the parent molecule of formula (II), for example by enzymic action, after it has passed through the bacterial cell wall.

As used herein the term "($C_1$–$C_6$)alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "divalent ($C_1$–$C_3$)alkylene radical" means a saturated hydrocarbon chain having from 1 to 3 carbon atoms and two unsatisfied valencies.

As used herein the term "($C_2$–$C_6$)alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

As used herein the term "heteroaryl" refers to a 5- or 6-membered aromatic ring containing one or more heteroatoms;. Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl.

As used herein the unqualified term "heterocyclyl" or "heterocyclic" includes "heteroaryl" as defined above, and in particular means a 5–7 membered aromatic or non-aromatic heterocyclic ring containing one or more heteroatoms selected from S, N and O, including for example, pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, maleimido and succinimido groups.

Unless otherwise specified in the context in which it occurs, the term "substituted" as applied to any moiety herein means substituted with up to four substituents, each of which independently may be ($C_1$–$C_6$)alkyl, ($C_1$–$C_6$)alkoxy, hydroxy, mercapto, ($C_1$–$C_6$)alkylthio, amino, halo (including fluoro, chloro, bromo and iodo), trifluoromethyl, nitro, —COOH, —$CONH_2$, —$COR^A$, —$COOR^A$, —$NHCOR^A$, —$CONHR^A$, —$NHR^A$, —$NR^AR^B$, or —$CONR^AR^B$ wherein $R^A$ and $R^B$ are independently a ($C_1$–$C_6$)alkyl group As used herein the terms "side chain of a natural alpha-amino acid" and "side chain of a non-natural alpha-amino acid" mean the group $R^x$ in respectively a natural and non-natural amino acid of formula $NH_2$—CH($R^x$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

In natural alpha-amino acid side chains which contain functional substituents, for example amino, carboxyl, hydroxy, mercapto, guanidyl, imidazolyl, or indolyl groups as in arginine, lysine, glutamic acid, aspartic acid, tryptophan, histidine, serine, threonine, tyrosine, and cysteine, such functional substituents may optionally be protected.

Likewise, in the side chains of non-natural alpha amino acids which contain functional substituents, for example amino, carboxyl, hydroxy, mercapto, guanidyl, imidazolyl, or indolyl groups, such functional substituents may optionally be protected.

The term "protected" when used in relation to a functional substituent in a side chain of a natural or non-natural alpha-amino acid means a derivative of such a substituent which is substantially non-functional. The widely used handbook by T. W. Greene and P. G. Wuts "Protective Groups in Organic Synthesis" Second Edition, Wiley, New York, 1991 reviews the subject. For example, carboxyl groups may be esterified (for example as a $C_1$–$C_6$ alkyl ester), amino groups may be converted to amides (for example as a $NHCOC_1$–$C_6$ alkyl amide) or carbamates (for example as an $NHC(=O)OC_1$–$C_6$ alkyl or $NHC(=O)OCH_2Ph$ carbamate), hydroxyl groups may be converted to ethers (for example an $OC_1$–$C_6$ alkyl or a $O(C_1$–$C_6$ alkyl) phenyl ether) or esters (for example a $OC(=O)C_1$–$C_6$ alkyl ester) and thiol groups may be converted to thioethers (for example a tert-butyl or benzyl thioether) or thioesters (for example a $SC(=O)C_1$–$C_6$ alkyl thioester).

There are several actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereoconfiguration of the carbon atom carrying the $R_2$ group is R; that of the carbon atom carrying the $R_4$ group (when asymmetric) is S; and that of the carbon atom carrying the $R_1$ group (when asymmetric) is R.

In the compounds of the invention:

$R_1$ may be, for example, hydrogen, methyl, or trifuoromethyl. Hydrogen is currently preferred.

$R_2$ may be, for example:

optionally substituted $C_1$–$C_8$ alkyl, $C_3$–$C_6$ alkenyl, $C_3$–$C_6$ alkynyl or cycloalkyl;

phenyl($C_1$–$C_6$ alkyly, phenyl($C_3$–$C_6$ alkenyl)- or phenyl ($C_3$–$C_6$ alkynyl)-optionally substituted in the phenyl ring;

cycloalkyl($C_1$–$C_6$ alkyl), cycloalkyl($C_3$–$C_6$ alkenyl) or cycloalkyl($C_3$–$C_6$ alkynyl)-optionally substituted in the cycloalkyl ring;

heterocyclyl($C_1$–$C_6$ alkyl), heterocyclyl($C_3$–$C_6$ alkenyl) or heterocyclyl($C_3$–$C_6$ alkynyl)-optionally substituted in the heterocyclyl ring; or $CH_3(CH_2)_pO(CH_2)_q$— or $CH_3(CH_2)_pS(CH_2)_q$, wherein p is 0, 1, 2 or 3 and q is 1, 2 or 3.

Specific examples of $R_2$ groups include methyl, ethyl, n- and iso-propyl, n- and iso-butyl, n-pentyl, iso-pentyl 3-methyl-but-1-yl, n-hexyl, n-heptyl, n-acetyl, n-octyl, methylsulfanylethyl, ethylsulfanylmethyl, 2-methoxyethyl, 2-ethoxyethyl, 2-ethoxymethyl, 3-hydroxypropyl, allyl, 3-phenylprop-3-en-1-yl, prop-2-yn-1-yl, 3-phenylprop-2-yn-1-yl, 3-(2-chlorophenyl) prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, and 4-methoxybenzyl.

Presently preferred groups at $R^2$ are ($C_1$–$C_6$)alkyl-, cycloalkylmethyl-, ($C_1$–$C_3$)alkyl-S-($C_1$–$C_3$)alkyl-, or ($C_1$–$C_3$)alkyl-O—($C_1$–$C_3$)alkyl-, especially n-propyl, n-butyl, n-pentyl, cyclopentylmethyl, cyclopentylethyl, cyclohexylmethyl or cyclohexylethyl.

$R_4$ may be, for example the characterising group of a natural a amino acid, for example benzyl, or 4-methoxyphenylmethyl, in which any functional group may be protected, any amino group may be acylated and any carboxyl group present may be amidated; or a group -$[Alk]_nR_9$ where Alk is a ($C_1$–$C_6$)alkylene or ($C_2$–$C_6$)alkenylene group optionally interrupted by one or more —O—, or —S— atoms or —N($R_{12}$)-groups [where $R_{12}$ is a hydrogen atom or a ($C_1$–$C_6$)alkyl group], n is 0 or 1, and $R_9$ is hydrogen or an optionally substituted phenyl, aryl, heterocyclyl, cycloalkyl or cycloalkenyl group or (only when n is 1) $R_9$ may additionally be hydroxy, mercapto, ($C_1$–$C_6$)alkylthio, amino, halo, trifluoromethyl, nitro, —COOH, —$CONH_2$, —$COOR^A$, —$NHCOR^A$, —$CONHR^A$, —$NHR^A$, —$NR^AR^B$, or —$CONR^AR^B$ wherein $R^A$ and $R^B$ are independently a ($C_1$–$C_6$)alkyl group; or a benzyl group substituted in the phenyl ring by a group of formula —$OCH_2COR_8$ where $R_8$ is hydroxyl, amino, ($C_1$–$C_6$)alkoxy, phenyl($C_1$–$C_6$)alkoxy, ($C_1$–$C_6$) alkylamino, di(($C_1$–$C_6$)alkyl)amino, phenyl($C_1$–$C_6$) alkylamino; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —$CR_aR_bR_c$ in which:

each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or $R_c$ is hydrogen and $R_a$ and $R_b$ are independently phenyl or heteroaryl such as pyridyl; or $R_c$ is hydrogen, ($C_1$–$C_6$)alkyl, ($C_2$–$C_6$)alkenyl, ($C_2C_6$) alkynyl, phenyl($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$)alkenyl, ($C_2$–$C_6$)alkynyl, phenyl($C_1$–$C_6$) alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2H$, ($C_1$–$C_4$)perfluoroalkyl, —$CH_2OH$, —$CO_2$($C_1$–$C_6$)alkyl, —O($C_1$–$C_6$)alkyl, —O($C_2$–$C_6$)alkenyl, —S($C_1$–$C_6$)alkyl, —SO($C_1$–$C_6$)alkyl, —$SO_2$($C_1$–$C_6$) alkyl, -S($C_2$–$C_6$)alkenyl, —SO($C_2$–$C_6$)alkenyl, —$SO_2$($C_2$–$C_6$)alkenyl or a group -Q-W wherein Q represents a bond or —O—, —S—, —SO— or —$SO_2$— and W represents a phenyl, phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —$CO_2H$, —$CO_2(C_1$–$C_6)$alkyl, —$CONH_2$, —$CONH(C_1$–$C_6)$alkyl, —$CONH(C_1$–$C_6$alkyl$)_2$, —CHO, —$CH_2OH$, $(C_1$–$C_4)$perfluoroalkyl, —$O(C_1$–$C_6)$alkyl, —$S(C_1$–$C_8)$alkyl, —$SO(C_1$–$C_6)$alkyl, —$SO_2(C_1$–$C_6)$alkyl, —$NO_2$, —$NH_2$, —$NH(C_1$–$C_6)$alkyl, —$N((C_1$–$C_6)$alkyl$)_2$, —$NHCO(C_1$–$C_6)$alkyl, $(C_1$–$C_6)$alkyl, $(C_2$–$C_6)$alkenyl, $(C_2$–$C_6)$alkynyl, $(C_3$–$C_8)$cycloalkyl, $(C_4$–$C_8)$cycloalkenyl, phenyl or benzyl.

Examples of particular $R_4$ groups include methyl, ethyl, benzyl, 4-chlorobenzyl, 4-hydroxybenzyl, phenyl, cyclohexyl, cyclohexylmethyl, pyridin-3-ylmethyl, tert-butoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxethyl, 2-carboxyethyl, 2-methylcarbamoylethyl, 2-carbamoylethyl, and 4-aminobutyl. Presently preferred $R_4$ groups include tert-butyl, iso-butyl, benzyl, isopropyl and methyl.

$R_5$ and $R_6$ taken together with the nitrogen atom to which they are attached form a saturated 5- to 7-membered monocyclic N-heterocyclic first ring which is attached via the N atom, and which is optionally fused to a saturated or unsaturated carbocyclic or heterocyclic second ring of 5 to 7 atoms. One or more additional ring hetero atoms such as nitrogen may be present in the first ring. Examples of such first rings are 1-pyrrolidinyl, piperidin-1-yl, 1-piperazinyl, hexahydro-1-pyridazinyl, morpholin-4-yl, tetrahydro-1,4-thiazin-4-yl, tetrahydro-1,4-thiazin-4-yl 1-oxide, tetrahydro-1,4-thiazinA-yl 1,1-dioxide, hexahydroazipino, thiomorpholino, diazepino, thiazolidinyl or octahydroazocino. Presently preferred are piperidin-1-yl and 1-piperazinyl. The substituent (IIC) may be present on a ring carbon atom or a ring nitrogen atom of the first or second rings.

In the substituent (IIC) (from whose definition benzyl, certain substituted benzyls, and phenoxy are excluded) $Alk^1$ and $Alk^2$ may independenty represent, for example —$(CH_2)$ or —$(CH_2CH_2)$. In the case where m is 0 and p is 1, X may be, for example —C(═O)— or —$S(O_2)$—. In such cases n may be 0 or 1, and when the —$NR_5R_6$ first ring contains a second ring nitrogen, the —C(═O)— or —$S(O_2)$— of (IIC) may be linked to that ring nitrogen in an amide or sulphonamide bond.

In the substituent (IIC) m, n and p may all be 0, so that the group Z is directly linked to the —$NR_5R_6$ first ring.

In a preferred subset of the compounds of the invention, the substituent (IIC) has the formula —$CH_2Z$, —OZ, or —(C═O)Z wherein (subject to the exclusion of benzyl, certain substituted benzyls, and phenoxy) Z is a phenyl, 3,4-methylenedioxyphenyl, morpholinyl, pyrimidinyl, 1,2,3-thiadiazolyl, 1,4-thiazolyl, benzofuranyl, furanyl, thienyl, pyranyl, pyrrolyl, pyrazolyl, isoxazolyl, or pyridyl ring which may optionally be substituted as specified. In particular, Z may be a phenyl, 3,4-methylenedioxyphenyl, morpholinyl, pyrimidin-2-yl, 1,2,3-thiadiazol-5-yl, 1,4-thiazol-5yl, benzofuran-2-yl, 2- or 3-furanyl, 2- or 3-thienyl, 2- or 3-pyranyl, 2-, 3- or 4-pyrrolyl, 3-, 4- or 5-pyazolyl, 3-, 4- or 5-isoxazolyl, or 2-, 3- or 4-pyridyl ring any of which may optionally be substituted as specified in the broad description of the compounds of the invention.

In the compounds of formula (II) as defined above wherein Q is a radical of formula —C(═O)NH(OH) the radicals $R_1$, $R_2$, and A may be any of those discussed ubove in relation to compounds (II) wherein Q is a radical of formula —N(OH)CH(═O). However, in addition, $R_1$ may be, for example, a hydroxy, methoxy, ethoxy, n-propyloxy, allyloxy, amino, methylamino, dimethyl amino, ethylamino, or diethylamino group.

Specific examples of substituents (IIC) include those present in the compounds specifically named, and/or exemplified herein.

Examples of specific compounds of the invention are those of the Examples herein. In those Examples, where a compound of formula (II) above wherein Q is an N-formylhydroxylamine radical —N(OH)CH(═O) is disclosed, it is to be understood that the equivalent compound wherein Q is a hydroxamate radical —C(═O)NH(OH) is also a specific compound of the invention, and vice versa.

Preferred compounds of the invention include those selected from the group consisting of compounds of formulae (IID)–(IIG) and (IIW)–(IIZ):

(IID)

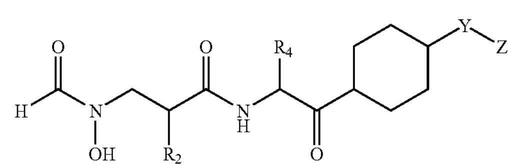

(IIE)

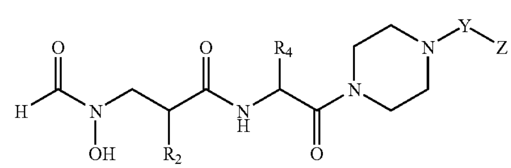

(IIF)

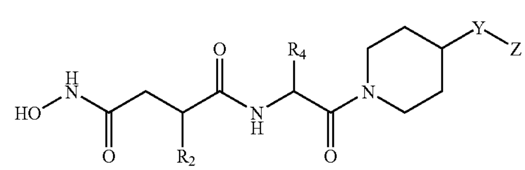

(IIG)

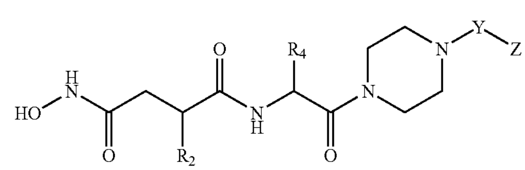

(IIW)

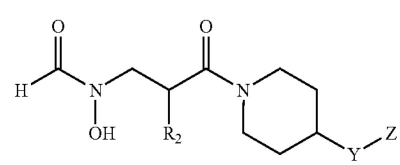

(IIX)

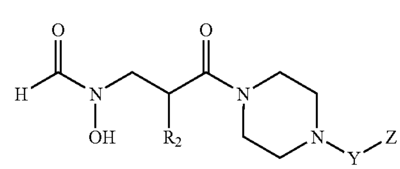

-continued (IIY)

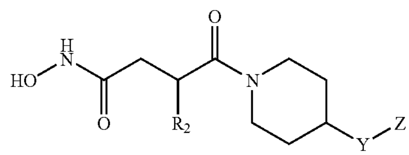

(IIZ)

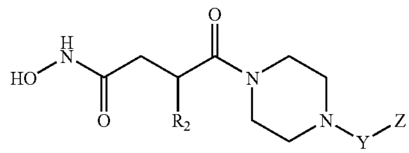

wherein $R_2$ is n-propyl, n-butyl, n-pentyl, cyclopentylmethyl, cyclopentylethyl, cyclohexylmethyl or cyclohexylethyl;

$R_4$ is tert-butyl, iso-butyl, benzyl or methyl;

Y is $—CH_2—$, —O— or —(C═O)—; and

Z is a phenyl, 3,4-methylenedioxyphenyl, morpholinyl, pyrimidinyl, 1,2,3-thiadiazolyl, 1,4-thiazolyl, benzofuranyl, furanyl, thienyl, pyranyl, pyrrolyl, pyrazolyl, isoxazolyl, or pyridyl ring; in particular, a phenyl, 3,4-methylenedioxyphenyl, morpholinyl, pyrimidin-2-yl, 1,2,3-thiadiazol-5-yl, 1,4-thiazol-5-yl, benzofuran-2-yl, 2-or 3-furanyl, 2- or 3-thienyl, 2- or 3-pyranyl, 2-, 3- or 4-pyrrolyl, 3-, 4- or 5-pyazolyl, 3, 4- or 5-isoxazolyl, or 2-, 3- or 4-pyridyl ring, which may optionally be substituted as specified in the general description of compounds of the invention.

Particular compounds of the invention, preferred for their potency against organisms which infect the respiratory system, include N-[1S-(4-benzo[1,3]dioxol-5-ylmethyl-piperazine-1-carbonyl)2,2-dimethyl-propyl]-2R-cyclopentylmethyl-3-(formyl-hydroxy-amino)-propionamide and N-[1S-(4-Benzol[1,3]dioxol-5-ylmethyl-piperazine-1-carbonyl)-2,2-dimethyl-propyl]-2R-cyclopentylmethyl-N-hydroxy-succinamide Compounds of the invention in which Q is an N-formyl-hydroxyamino group may be prepared by deprotecting an O-protected N-formyl-N-hydroxyamino compound of formula (III):

(III)

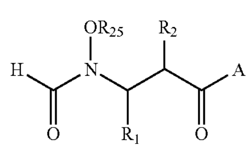

in which $R_1$, $R_2$, and A are as defined in general formula (I) and $R_{25}$ is a hydroxy protecting group removable to leave a hydroxy group by hydrogenolysis or hydrolysis. Benzyl is a preferred $R_{25}$ group for removal by hydrogenolysis, and tert-butyl and tetrahydropyranyl are preferred groups for removal by acid hydrolysis.

Compounds of the invention in which Q is a hydroxamic acid group may be prepared by reacting the parent compound wherein Q is a carboxylic acid group (IIIA)

(IIIA)

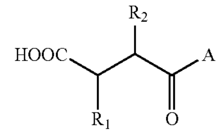

with hydroxylamine or an N- and/or O-protected hydroxylamine, and thereafter removing any O- or N-protecting groups Compounds of formula (III) or (IIIA) may be prepared by causing an acid of fornula (IV) or (IVC) or an activated derivative thereof to react with an amine of formula (IVA) or (IVB)

(IV)

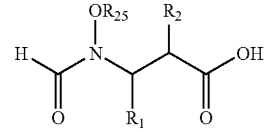

(IVA)

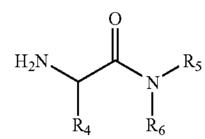

(IVB)

$HNR_5R_6$ (IVC)

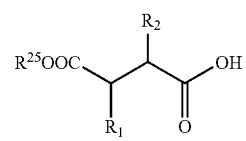

wherein $R_1$ $R_2$, $R_4$, $R_5$, and $R_6$ are as defined in general formula (II) except that any substituents in $R_1$ $R_2$, $R_4$, $R_5$, and $R_6$ which are potentially reactive in the coupling reaction may themselves be protected from such reaction, and $R_{25}$ is as defined in relation to formula (III) above, and optionally removing protecting groups $R_1$ $R_2$, $R_4$, $R_5$, and $R_6$.

Compounds of formula (IVA), (IVB) and (IVC) are prepared by standard literature methods, and many are commercially available.

Compounds of formula (IV) may be prepared by N-formylation, for example using acetic anhydride and formic acid, or 1-formylbenzotriazole, of compounds of formula (V)

(V)

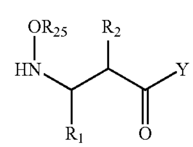

wherein $R_1$, $R_2$ and $R_{25}$ are as defined in relation to formula (III) and Y is either a chiral auxiliary or an $OR_{26}$ group wherein $R_{26}$ is hydrogen or a hydroxy protecting group. In the case where Y is an $OR_{26}$ group or a chiral auxiliary the hydroxy protecting group or auxiliary is removed after the formylation step to provide the compound of formula (IV). Suitable chiral auxiliaries include substituted oxazolidinones which may be removed by hydrolysis in the presence of base.

A compound of general formula (V) may be prepared by reduction of an oxime of general formula (VII)

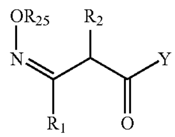
(VII)

wherein $R_1$, $R_2$, and $R_{25}$ are as defined above, and Y is either an $OR_{26}$ group as defined above or a chiral auxiliary. Reducing agents include certain metal hydrides (eg sodium cyanoborohydride in acetic acid, triethylsilane or borane/pyridine) and hydrogen in the presence of a suitable catalyst. Following the reduction when the group Y is a chiral auxiliary it may be optionally converted to a $OR_{26}$ group.

A compound of general formula (VII) can be prepared by reaction of β-keto carbonyl compound of general formula (VIII)

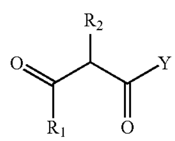
(VIII)

wherein $R_1$, $R_2$, and Y are as defined above, with an O-protected hydroxylamine.

β-keto carbonyl compounds (VIII) may be prepared in racemic form by formylation or acylabon of a carbonyl compound of general formula (IX)

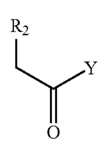
(IX)

wherein $R_2$ and Y are as defined above, with a compound of general formula (X)

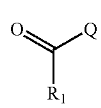
(X)

wherein $R_1$ is as defined above and Q is a leaving group such as halogen or alkoxy, in the presence of a base.

The Examples herein provide further details of routes and methods for the preparation of compounds of the invention.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

Compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutons or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate embodiments of the invention. Note that the "Preparative Example A" does not describe the preparation of a compound of the invention, but is included to provide details of synthetic routes and methods for the preparation of compounds of the invention $^1H$ and $^{13}C$ NMR spectra were recorded using a Bruker DPX 250 spectrometer at 250.1 and 62.9 MHz, respectively. Mass spectra were obtained using a Perkin Elmer Sciex API 165 spectrometer using both positive and negative ionisation modes. Infra-red spectra were recorded on a Perkin Elmer PE 1600 FTIR spectrometer. Analytical HPLC was performed on a Beckman System Gold, using Waters Nova Pak C18 column (150 mm, 3.9 mm) with 20 to 90% solvent B gradient (1 ml/min) as the mobile phase. [Solvent A: 0.05% TFA in 10% water 90% methanol; Solvent B: 0.05% TFA in 10% methanol 90%], detection wavelength at 230 nm. Preparative HPLC was performed on a Gilson autoprep instrument using a C18 Waters delta prep-pak cartridge (15 μm, 300 A, 25 mm, 10 mm) with 20 to 90% solvent B gradient (6 ml/min) as the mobile phase. [Solvent A water; Solvent B: methanol], UV detection was at 230 nm.

The following abbreviations have been used throughout:

DCM Dichloromethane

DEAD Diethyl-azo-dichlorocarboxylate

EDC N-Ethyl-N'-(3-dimethylaminopropyl)carbodiimide hydrochloride

HOAt 1-Hydroxy-7-aza-benzotriazole

HOBt 1-Hydroxybenzotriazole

HPLC High performance liquid chromatography

LRMS Low resolution mass spectrometry

NMR Nuclear magnetic resonance

RT Retention Time

TLC Thin layer chromatography

TFA Trifluoroacetic acid

THF Tetrahydrofuran

EXAMPLE 1

2R-[(Formyl-hydroxy-amino)-methyl]-hexanoic acid {1S-[4-(4-methoxy-benzoyl)-piperidine-1-carbonyl]-2,2-dimethyl-propyl}-amide

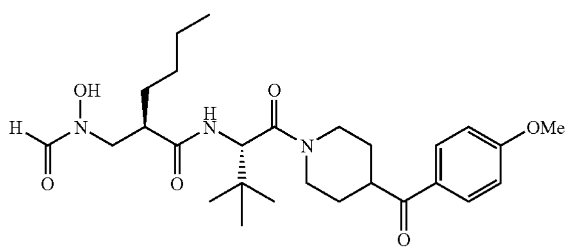

The title compound was prepared as detailed below (see also Scheme 1)

Scheme 1

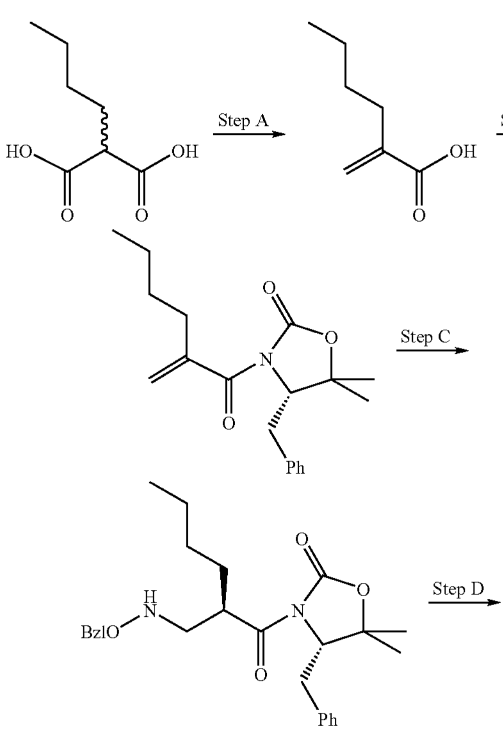

-continued

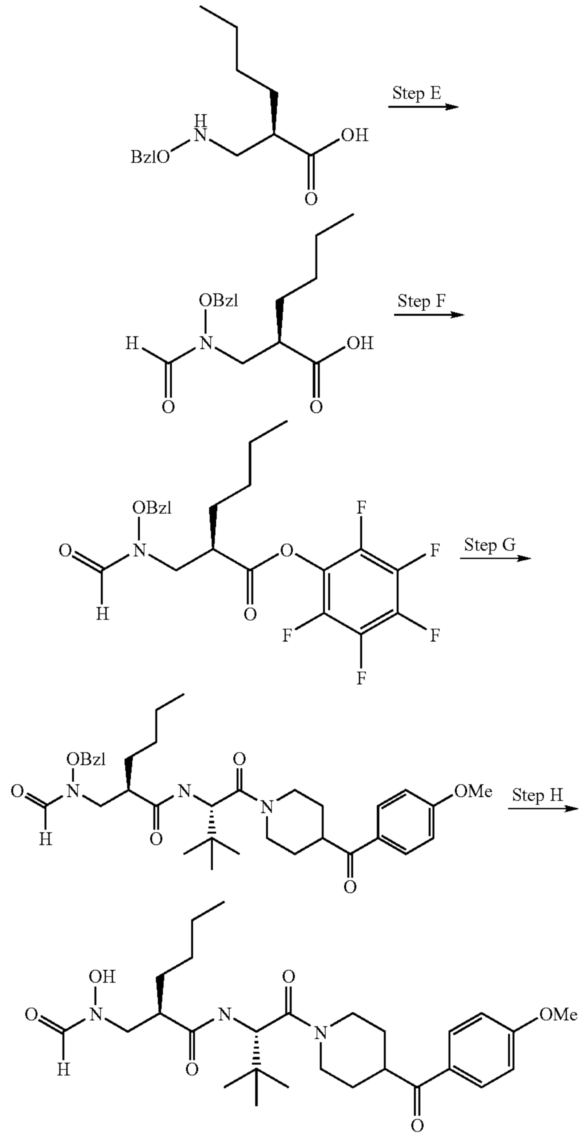

Step A: 2-Butyl acrylic acid

To a solution of n-butylmalonic acid (17.2 g, 107 mmol) in ethanol (200 ml) was added piperidine (12.76 ml, 129 mmol) and 37% aq. formaldehyde (40.3 ml, 538 mmol). The solution was heated to 80° C. during which time a precipitate appeared and gradually redissolved over 1 hour. The reaction mixture was stirred at 80° C. overnight then cooled to room temperature. The solvents were removed under reduced pressure and the residue was dissolved in ethyl acetate (200 ml), washed successively with 1 M hydrochloric acid and brine, dried over anhydrous magnesium sulfate and filtered. The filtrate was concentrated to give the title compound as a clear oil (13.37 g, 97%). $^1$H-NMR; δ ($CDCl_3$), 6.29 (1H, s), 5.65 (1H, s), 2.34–2.28 (2H, m), 1.54–1.26 (4H, M), 0.94 (3H, t, J=7.1 Hz).

Step B: 4S-Benzyl-3-(2-butyl-acryloyl)-5,5dimethyloxazolidin-2-one

2-Butyl acrylic acid (21.5 g, 168 mmol) was dissolved in dry THF (500 ml) and cooled to −78° C. under a blanket of argon. Triethylamine (30 ml, 218 mmol) and pivaloyl chloride (21 ml, 168 mmol) were added at such a rate that the temperature remained below −60° C. The mixture was stirred at −78° C. for 30 minutes, warmed to room temperature for 2 hours and finally cooled back to −78° C.

In a separate flask, 4S-benzyl-5,5-dimethyl-oxazolidin-2-one was dissoved in dry THF (500 ml) and cooled to −78° C. under a blanket of argon. n-Butyllithium (2.4 M solution in hexanes, 83 ml, 200 mmol) was added slowly and the mixture was stirred for 30 minutes at room temperature. The resulting anion was tranferred via a cannula into the original reaction vessel. The mixture was allowed to warm to room temperature and was stirred overnight at room temperature. The reaction was quenched with 1 M potassium hydrogen carbonate (200 ml) and the solvents were removed under reduced pressure. The residue was partitioned between ethyl acetate and water. The organic layer was washed with brine, dried over anhydrous magnesium sulfate, filtered and concentrated under reduced pressure to give an orange oil. TLC analysis revealed the presence of unreacted chiral auxiliary in addition to the required product. A portion of the material (30 g) was dissolved in dichloromethane and flushed through a silica pad to give pure title compound as a yellow oil (25.3 g). $^1$H-NMR; δ ($CDCl_3$), 7.31–7.19 (5H, m), 5.41 (2H,s), 4.51 (1H, dd, J=9.7 & 4.2 Hz), 3.32 (1H, dd, J=14.2 & 4.2 Hz), 2.82 (1H, dd, J=14.2 & 9.7 Hz), 2.40–2.34 (2H, m), 1.48–1.32 (4H, m), 1.43 (3H, s), 1.27 (3H, s), 0.91 (3H, t, J=7.1 Hz). Some chiral auxiliary was recovered by flushing the silica pad with methanol.

Step C: 4S-Benzyl-3-[2-(benzyloxyamino-methyl)-hexanoyl]-5,5-dimethyl-oxazolidin-2-one (p-toluenesulfonic acid salt)

4S-Benzyl-3-(2-butyl-acryloyl)-5,5-dimethyl-oxazolidin-2-one (19.8 g, 62.8 mmol) was mixed with O-benzylhydroxylamine (15.4 g, 126 mmol) and stirred overnight at room temperature. The mixture was dissolved in ethyl acetate and the solution was washed with 1 M hydrochloric acid, 1 M sodium carbonate and brine, dried over anhydrous magnesium sulfate and filtered. The filtrate was concentrated under reduced pressure to afford a pale yellow oil (25.3 g) which was shown by NMR and HPLC analysis to contain 4S-benzyl-3-[2-(benzyloxyamino-methyl)-hexanoy]-5,5-dimethyl-oxazolidin-2-one (ca. 82% d.e.) along with a trace of starting material. The product was combined with another batch (26.9 g, 76% d.e.) and dissolved in ethyl acetate (200 ml). p-Toluenesulfonic acid (22.7 g, 119 mmol) was added and the mixture was cooled to 0° C. The title compound was obtained as a white crystalline solid by seeding and scratching. Yield: 25.2 g, (34%, single diastereoisomer). A second crop (14.7 g, 20%, single diastereoisomer) was also obtained. $^1$H-NMR; δ ($CDCl_3$), 7.89 (2H, d, J=8.2 Hz), 7.37–7.12 (10H, m), 7.02 (2H, d, J=6.9 Hz), 5.28–5.19 (2H, m), 4.55 (1H, m), 4.23 (1H, m), 3.93 (1H, m), 3.58 (1H, m), 2.58 (1H, m), 2.35 (3H, s), 1.67–1.51 (2H, m), 1.29–1.16 (4H, m), 1.25 (3H, s), 1.11 (3H, s), 0.80–0.75 (3H, m).

Step D: 2R-(Benzyloxyamino-methyl)-hexanoic acid

4S-Benzyl-3-[2R-(benzyloxyamino-methylyhexanoyl]-5,5-dimethyl-oxazolidin-2-one p-toluenesulfonic acid salt (25.2 g, 40.2 mmol) was partitioned between ethyl acetate and 1 M sodium carbonate. The organic phase was dried over anhydrous magnesium sulfate, filtered and evaporated under reduced pressure. The residual oil was dissolved in THF (150 ml) and water (50 ml), cooled to 0° C. and treated with lithium hydroxide (1.86 g, 44.2 mmol). The solution was stirred for 30 minutes at 0° C., then overnight at room temperature. The reaction was acidified to pH4 with 1 M citric acid and the solvents were removed. The residue was partitioned between dichloromethane and 1 M sodium carbonate. The basic aqueous layer was acidified to pH4 with 1 M citric acid and extracted three times with ethyl acetate. The combined organic layers were dried over anhydrous magnesium sulfate, filtered and concentrated to provide the title compound as a colourless oil (7.4 g, 73%). $^1$H-NMR; δ ($CDCl_3$), 8.42 (2H, br s), 7.34–7.25 (5H, m), 4.76–4.66 (2H, m), 3.20–3.01 (2H, m), 2.73 (1H, m), 1.70–1.44 (2H, m), 1.34–1.22 (4H, m) and 0.92–0.86 (3H, m).

Step E: 2R-[(Benzyloxy-formylamino)-methyl)]-hexanoic acid

To a solution of 2R-(Benzyloxyamino-methyl)-hexanoic acid (30.6 g, 0.12 mol) in dry THF (300 ml) was added formic acetic anhydride (26.8 ml, 0.31 mol) at 0° C. Triethylamine (18.5 ml, 0.13 mol) was added and the reaction was stirred for 1 h at 0° C. and 60 h at room temperature. The solvent was removed in vacuo to yield the title compound as a yellow oil (33.6 g, 99%) which was used in Step F without further purification. $^1$H-NMR; ($CDCl_3$, rotamers), 8.20–8.08 (0.7H, br s), 8.07–7.92 (0.3H, br s), 7.50–7.25 (5H, br m), 5.07–4.70 (2H, br m), 3.95–3.52 (2H, br m), 2.90–2.66 (1H, br s), 1.72–1.20 (6H, br m), 1.00–0.78 (3H, br s). LRMS: +ve ion 280 [M+1].

Step F: 2R-[(Benzyloxy-formyl-amino)-methyl]-hexanoic acid pentafluoro-phenyl ester To a solution of 2R-[(Benzyloxy-formylaminoymethyl)]-hexanoic acid (7.8 g, 19.9 mmol) in dry THF (500 ml) was added pentafluorophenol (44.3 g, 0.24 mol), EDC (27.7 g, 0.14 mol) and HOBt (16.2 g, 0.12 mol). The reaction was stirred overnight at room temperature. The solvent was removed in vacuo and the residue was dissolved in ethyl acetate, washed successively with 1 M sodium carbonate (3×500 ml) and water (1×500 ml), dried over anhydrous magnesium sulfate and filtered. The solvent was removed in vacuo to yield a yellow oil (60 g) that was purified by flash chromatography (5:1, hexane:ethyl acetate→1:2 hexane: ethyl acetate) to yield a clear oil (42.0 g, 79%). $^1$H-NMR; δ($CDCl_3$, rotamers), 8.20–8.09 (0.7H, br s), 8.09–7.92 (0.3H, br s), 7.60–7.21 (5H, br m), 5.00–4.70 (2H, br m), 4.04–3.72 (2H, br m), 3.18–3.00 (1H, br s), 1.85–1.57 (2H, br m), 1.50–1.26 (4H, br m), 1.00–0.82 (3H, br m); LRMS: 466 [M+H].

Step G: 2R-[(Benzyloxy-formyl-amino)-methyl]-hexanoic acid {1S-[4-4-methoxy-benzoyl)-piperidine-1-carbonyl]-2,2-dimethyl-propyl}-amide 2R-[(Benzyloxy-formyl-amino)-methyl]-hexanoic acid pentafluorophenyl ester (231 mg, 0.52 mmol) and 2S-amino-1-[4-(4-methoxy-benzoyl)-piperidin-1-yl]-3,3-dimethyl-butan-1-one (prepared fromr N-benzyloxycarbonyl-L-tert-leucine) (259 mg, 0.78 mmol) were dissolved in dichloromethane (6 ml) and the mixture was stirred overnight at 27° C. An excess of Amberlyst A-21 ion exchange resin was added and the mixture stirred for 2.5 hrs before filtration. The resulting solution was then treated with methyl isocyanate polystyrene resin for 5 hrs. The mixture was filtered and solvent was removed under reduced pressure. Mass spectrometric analysis showed presence of pentafluorophenol, so the residue was dissolved in methanol (5 ml) and an excess of A-26 carbonate resin was added. The mixture was stirred overnight before filtration and removal of solvent under reduced pressure to afford the title compound as a brown oil (358 mg, 0.60 mmol). LRMS: +ve ion 594 [M+H].

Step H: 2R-[(Formyl-hydroxy-amino)-methyl]-hexanoic acid {1S-[4(4-methoxy-benzoyl)-piperidine-1-carbonyl]-2,2-dimethyl-propyl}-amide 2R-[(Benzyloxy-formyl-amino)-methyl]-hexanoic acid {1S-[4-(4-methoxy-benzoyl) piperidine-1-carbonyl-2,2-dimethyl-propyl)amide (358 mg, 0.60 mmol) was dissolved in ethanol (6 ml). Cyclohexene (0.60 ml) was added and the mixture placed under a blanket of argon. A suspension of 10% palladium on charcoal (40 mg) in ethyl acetate (1 ml) was added and the mixture was stirred at 70° C. for 5 hrs. The reaction mixture was cooled and the catalyst removed by filtration. The filtrate was concentrated to provide the title compound as a brown oil (294 mg, 0.58 mmol). Characterising data are provided in Table 1.

The compounds of Examples 2–13 were prepared by the synthetic route outlined in Scheme 1 and as described in detail for Example 1. Steps G and H were carried out in parallel for all examples. L-tert-leucine derivatives were prepared according to established literature methods. Purification of the final compounds, where necessary, was carried out by preparative HPLC.

TABLE 1

| Example | Structure | Mass Spec. Data | HPLC |
|---|---|---|---|
| 1 | 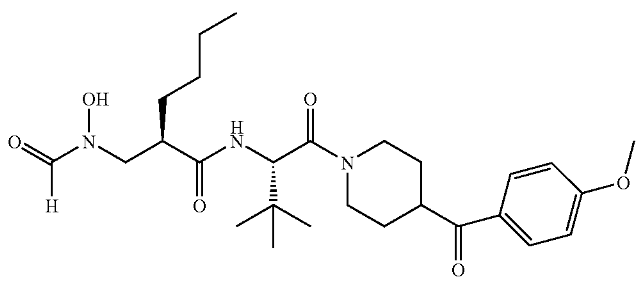 | [M + H] = 504 | RT = 21.7 mins<br>88% pure |
| 2 | 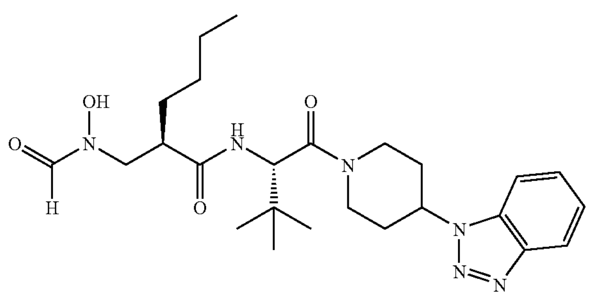 | [M + H] = 487 | RT = 20.1 mins<br>85% pure |
| 3 | 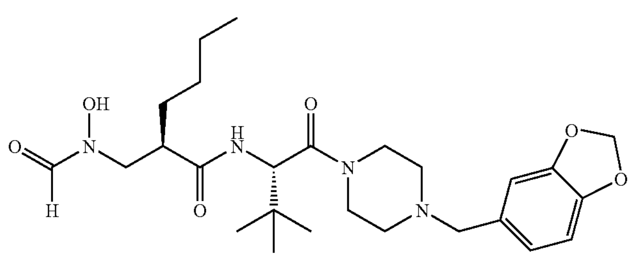 | [M + H] = 505<br>[M − H] = 503 | RT = 17.3 mins<br>83% pure |
| 4 | 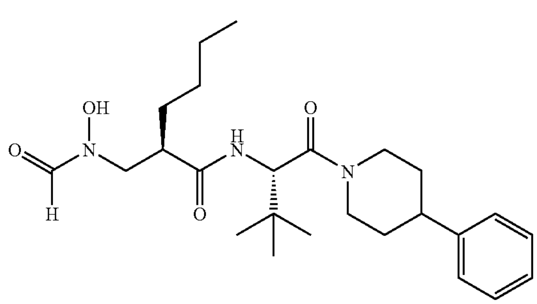 | [M + H] = 447<br>[M − H] = 445 | RT = 21.5 mins<br>90% pure |

TABLE 1-continued
| Example | Structure | Mass Spec. Data | HPLC |
|---|---|---|---|
| 5 | 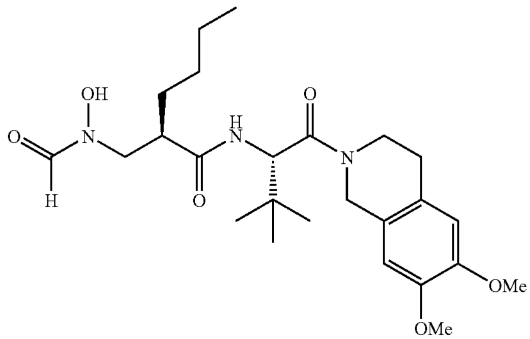 | [M + H] = 478<br>[M + Na] =500<br>[M − H] = 476 | RT = 20.8 mins<br>95% pure |
| 6 | 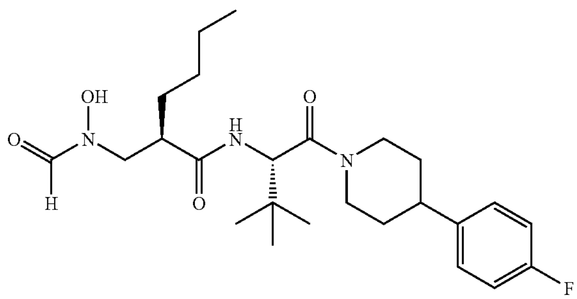 | [M + H] = 465<br>[M − H] = 463 | RT = 20.6 mins<br>93% pure |
| 7 | 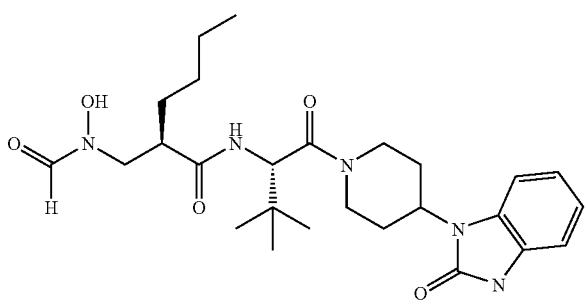 | [M + H] = 502<br>[M + Na] =524<br>[M − H] = 500 | RT = 19.3 mins<br>94% pure |
| 8 | 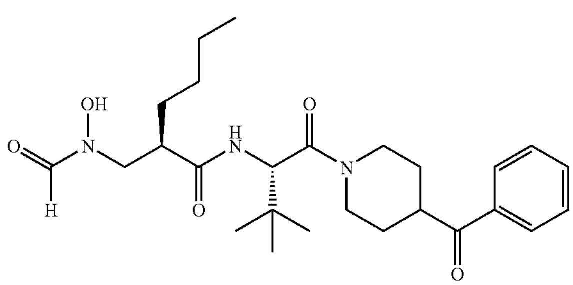 | [M + H] = 496<br>[M − H] = 472 | RT = 21.2 mins<br>91% pure |

TABLE 1-continued
| Example | Structure | Mass Spec. Data | HPLC |
|---|---|---|---|
| 9 | 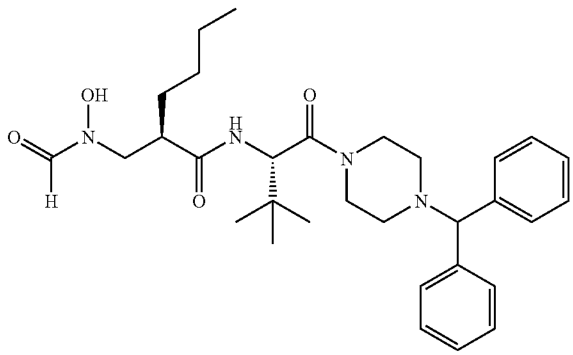 | [M + H] = 537<br>[M − H] = 535 | RT = 19.8 mins<br>95% pure |
| 10 | 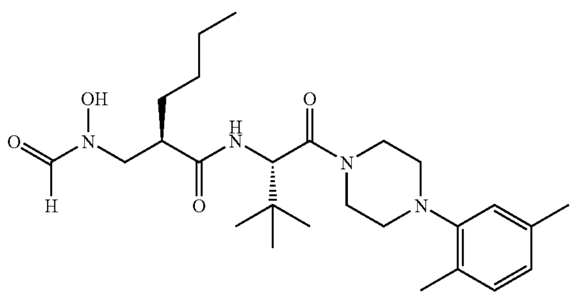 | [M + H] = 475<br>[M − H] = 473 | RT = 24.3 mins<br>87% pure |
| 11 | 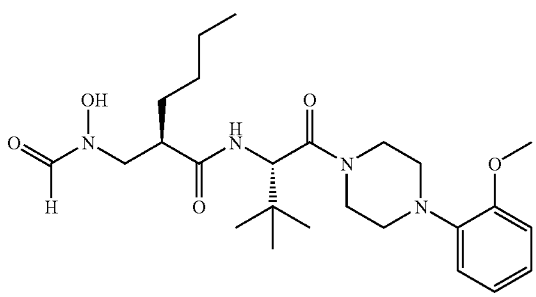 | [M + H] = 477<br>[M − H] = 475 | RT 20.3 mins<br>84% pure |
| 12 | 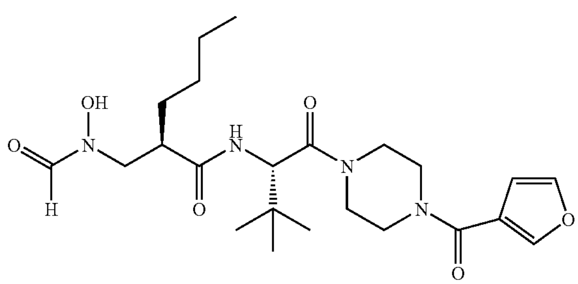 | [M + Na] = 487<br>[M − H] = 463 | RT = 18.7 mins<br>94% pure |
| 13 | 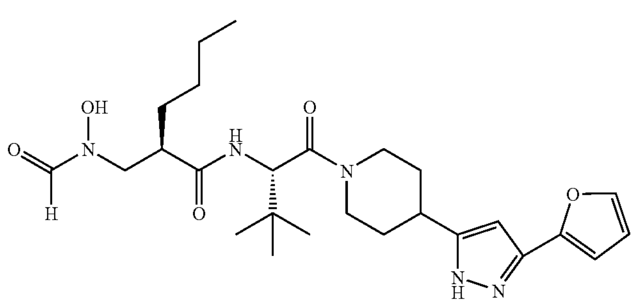 | [M + H] =502 | RT = 21.0 mins<br>88% pure |

TABLE 1-continued

| Example | Structure | Mass Spec. Data | HPLC |
|---|---|---|---|
| 14 | 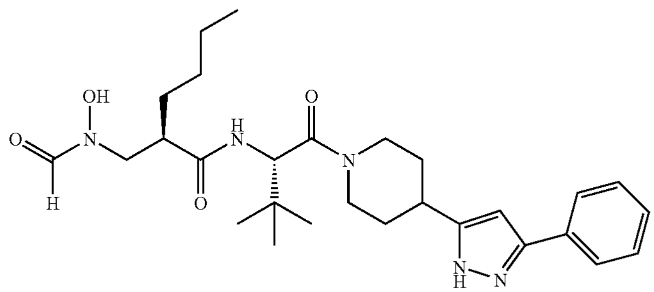 | [M + H] = 512<br>[M − H] = 510 | RT = 21.7 mins<br>84% pure |
| 15 | 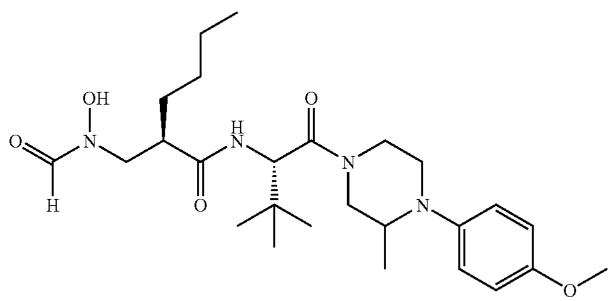 | [M + H] = 491<br>[M = H] = 489 | RT = 18.7 mins<br>98% pure |
| 16 | 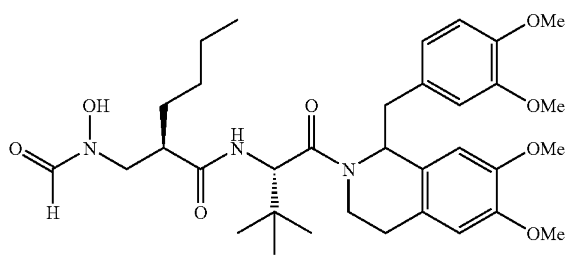 | [M + Na] = 650<br>[M − H] = 626 | RT = 21.5 mins<br>86% pure |
| 17* | 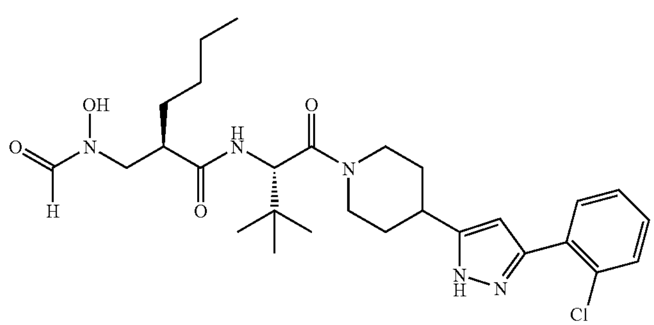 | [M + H] = 546<br>[M − H] = 544 | RT = 22.8 mins<br>88% pure |

#$^1$H-NMR; δ ($CD_3OD$, rotamers), 8.26 (0.4H ,s), 7.84 (0.6H, s), 7.69 (2H, m), 7.39 (2H, m), 6.49 (0.4H, s), 6.42 (0.6H, s), 5.01 (0.6H, s), 4.96 (0.4H, s), 4.64 (0.6H, d, J = 13.1 Hz), 4.51 (0.4H, d, J = 13.2 Hz), 4.36 (0.6H, d, J = 13.2 Hz), 4.29 (0.4H, d, J = 13.6 Hz), 3.10 (1H, m), 3.43 (0.4H, m), 3.32 (0.6H, m), 3.00 (2H, m), 2.86 (2H, m), 2.09 (2H, m), 1.59 (4H, m), 1.27 (4H, m), 1.02 (9H, m), 0.90 (1.4H, s) and 0.79 (1.6H, s).

The compounds of Examples 18 to 40 were prepared from 2R-[(Benzyloxy-formyl-amino)-methyl]-hexanoic acid pentafluorophenyl ester in a similar way to Example 1 but with the following modifications.

Step G: Generic Experimental Procedure for the Synthesis of an Array of Amides

The coupling of amines to the pentafluorophenyl ester were carried out on a Zymate XPII laboratory robot. To a solution of the pentafluorophenyl ester (55.8 mg, 0.12 mmol) in dichoromethane (2 ml) were added the individual amines (0.25 mmol) and the reaction mixtures were stirred at room temperature for 60 h. Purification was effected by removing excess amine and pentafluorophenol using scavenger resins. The pentafluorophenol was removed using a three fold excess (0.36 mmol) of A-26 carbonate resin (3.5 mmol loading). The resin was added to the reaction mixtures and agitated for 24 h, after which time it was filtered off. The excess amines were removed using a three fold excess (0.36 mmol) of methylisocyanate polystyrene resin (1.2 mmol loading). The resin was added to the reaction mixtures and agitated for 4 h, after which time it was filtered off. The solvent was removed in vacuo using a Savant Speed Vac Plus to yield the coupled products. Yields were not calculated and the purity and integrity of each compound was verified using HPLC and LRMS.

Step H: Generic Transfer Hydrogenation Procedure

Coupled products from Step G were taken up in an ethanol-cyclohexene solution (3 ml, 10% in cyclohexene) and Pd/C (20% w/w) was added and the reactions stirred at 80° C. for 24 h. The Pd/C was filtered off and the solvent was removed in vacuo using a Savant Speed Vac Plus to yield the title compounds (Examples 18 to 40, Table 2). Yields were not calculated and the purity and integrity of each compound was verified using HPLC and LRMS.

TABLE 2

| Example | Structure | Mass Spectral Data | HPLC | Purification |
|---|---|---|---|---|
| 18 | 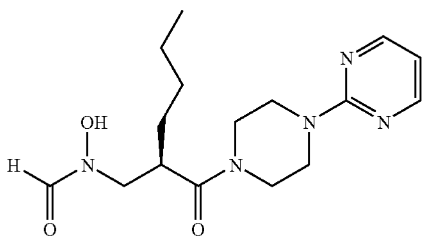 | 336(M + 1, 70) | RT 7.5 min 100% | Ion exchange resin, Prep HPLC |
| 19 | 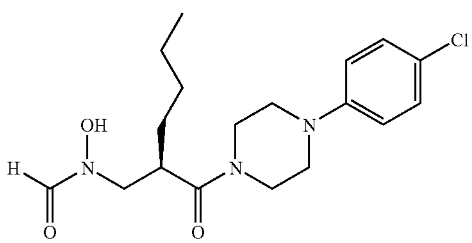 | 368(M + 1, 100) | RT 21.8 min 80% | Resins, Prep HPLC |
| 20 | 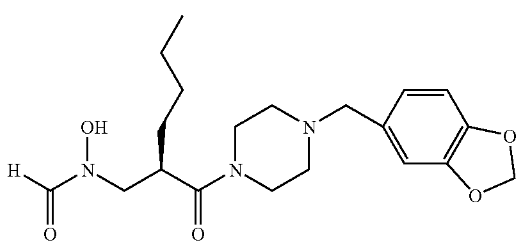 | 392(M + 1, 100) | RT 8.2 min 100% | Resins Prep HPLC |
| 21 | 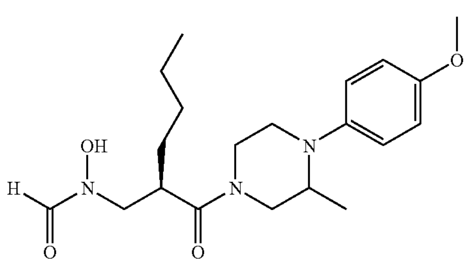 | 378(M + 1, 40) 362([M + 1]-Me, 100) | RT 12.0 min and 12.2 min (diastereomers) >98% | Resins Prep HPLC |
| 22 | 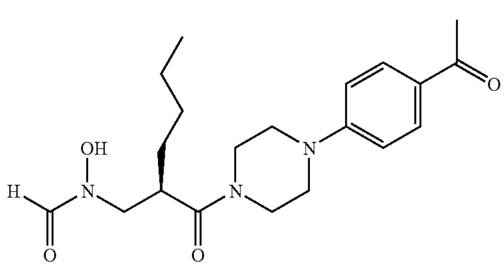 | 376(M + 1, 100) | RT 18.5 min 100% | Resins |

TABLE 2-continued
| Example | Structure | Mass Spectral Data | HPLC | Purification |
| --- | --- | --- | --- | --- |
| 23 | 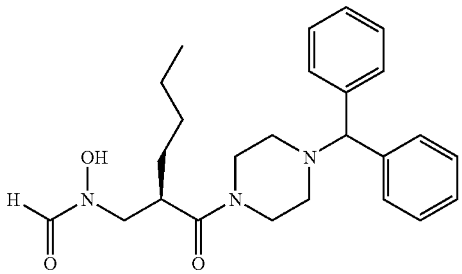 | 424(M + 1, 30),<br>258([M + 1]-<br>$[C_6H_5]_2CH$, 100) | RT 17.5 min<br>95% | Resins |
| 24 | 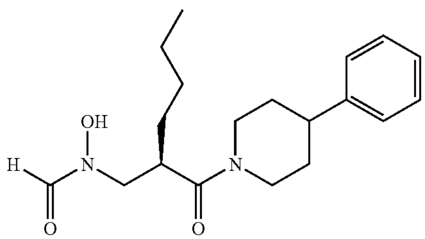 | 333(M + 1, 30) | RT 21.6 min<br>100% | Resins |
| 25 | 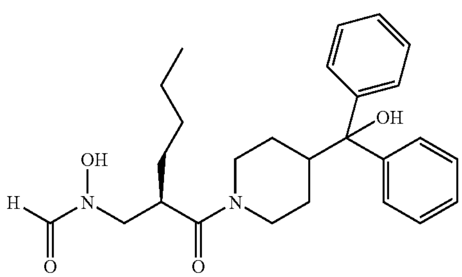 | 421(M + 1-$H_2O$, 50)<br>437(M − 1, 60) | RT 22.3 min<br>100% | Resins<br>prep HPLC |
| 26 | 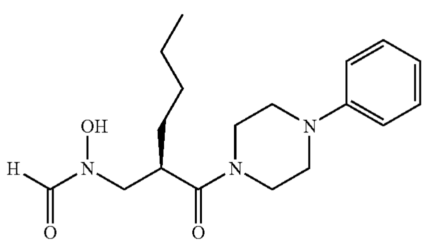 | 334(M + 1, 100) | RT 17.7 min<br>100% | Resins |
| 27 | 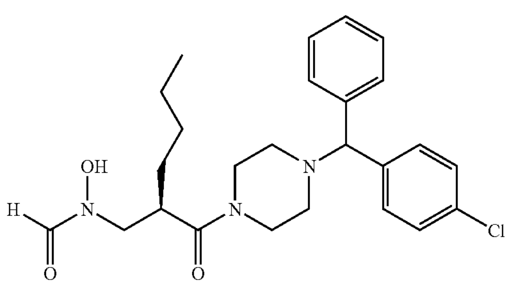 | 458(M + 1, 20)<br>258([M + 1]−<br>$[C_6H_5]C_6H_4ClCH$,<br>100) | RT 26.4 min<br>100% | Resins<br>prep HPLC |
| 28 | 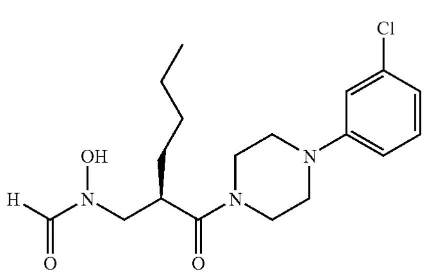 | 368(M + 1, 100) | RT 22.1 min<br>100% | Resins<br>prep HPLC |

TABLE 2-continued
| Example | Structure | Mass Spectral Data | HPLC | Purification |
|---|---|---|---|---|
| 29 | 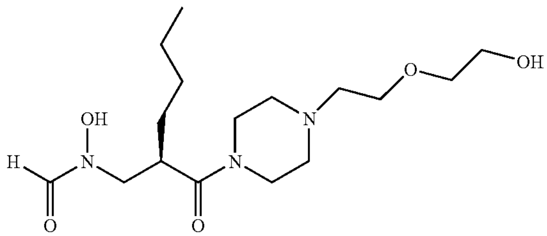 | 346(M + 1, 100) | 2 peaks, RT 3.2 min and 3.6 min 100% | Resins |
| 30 | 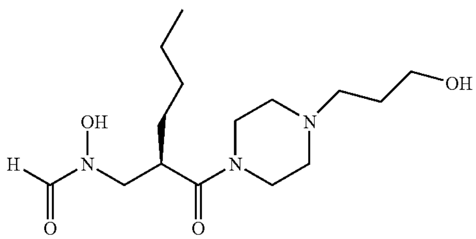 | 316(M + 1, 100) | 2 peaks RT 3.1 min and 3.5 min 100% | Resins |
| 31 | 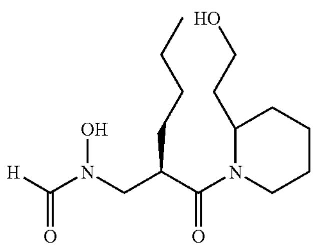 | 283([M + 1]-$H_2O$, 90) | 1 peak with shoulder, RT 16.8 min | Resins |
| 32 | 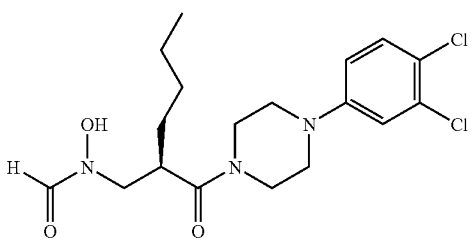 | 402(M + 1, 100) | RT 15.8 min >95% | Resins |
| 33 | 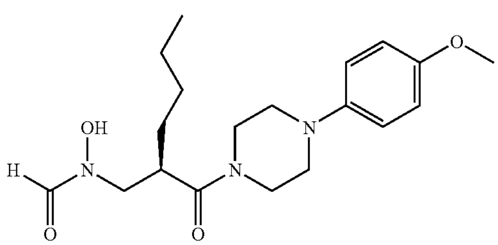 | 364(M + 1, 100) | RT 11.7 min >95% | Resins |
| 34 | 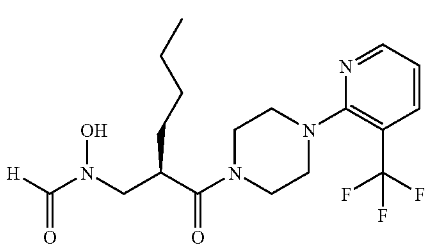 | 403(M + 1, 100) | RT 14.7 min 95% | Resins |

TABLE 2-continued
| Example | Structure | Mass Spectral Data | HPLC | Purification |
| --- | --- | --- | --- | --- |
| 35 | 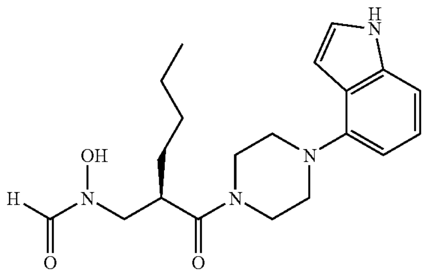 | 373(M + 1, 100) | RT 14.5 min<br>95% | Resins |
| 36 | 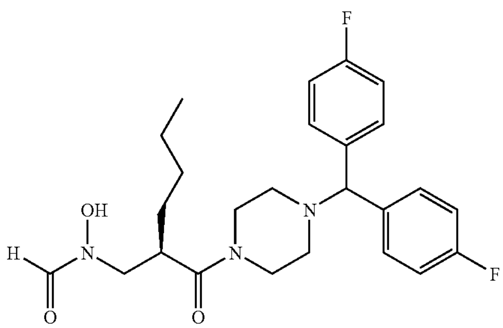 | 460(M + 1, 100) | RT 13.3 min<br>>95% | Resins<br>Prep HPLC |
| 37 | 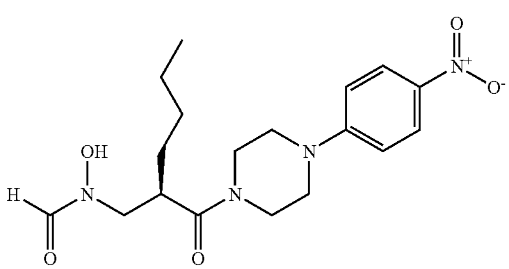 | 379(M + 1, 100), | RT 13.6 min<br>>95% | Resins |
| 38 | 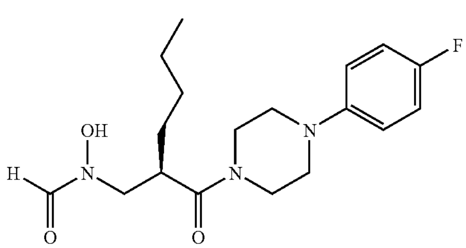 | 352(M + 1, 100) | RT 5.9 min<br>>95% | Resins |

TABLE 2-continued

| Example | Structure | Mass Spectral Data | HPLC | Purification |
|---|---|---|---|---|
| 39 | 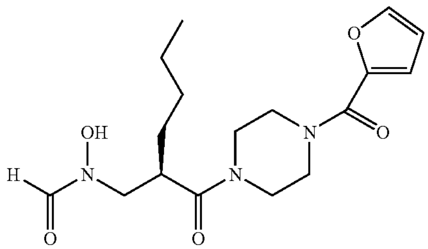 | 352(M + 1, 100) | RT 11.3 min >95% | Resins |
| 40 | 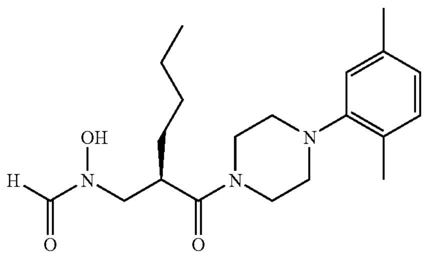 | 362(M + 1, 100) | 15.7 min >95% | Resins |

The compounds of the Examples 1–40 are named as follows:

EXAMPLE 1

2R-[(Formyl-hydroxy-amino)-methyl]-hexanoic acid

51{1S-[4-(4-methoxy-benzoyl)-piperidine-1-carbonyl]-2,2-dimethyl-propyl)-amide

EXAMPLE 2

2R-[(Formyl-hydroxy-amino)-methyl]-hexanoic acid

[1S-(4-benzotriazol-1-yl-piperidine-1-carbonyl)-2,2-dimethyl-propyl]-amide

EXAMPLE 3

2R-[(Formyl-hydroxy-amino)-methyl]-hexanoic acid

[1S-(4-benzo[1,3]dioxol-5-ylmethyl-piperazine-1-carbonyl)-2,2-dimethyl-propyl]-amide

EXAMPLE 4

2R-[(Formyl-hydroxy-amino)-methyl]-hexanoic acid

[2,2-dimethyl-1S-(4-phenyl-piperidine-1-carbonylypropyl]-amide

EXAMPLE 5

2R-[(Formyl-hydroxy-amino)methyl]-hexanoic acid

[1S-(6,7-dimethoxy-3,4-dihydro-1H-isoquinoline-2-carbonyl)2,2-dimethyl-propyl]-amide

EXAMPLE 6

2R-[(Formyl-hydroxy-aminoymethyl]-hexanoic acid

{1S-14-(4-fluoro-phenyl)-piperidine-1-carbonyl]-2,2-dimethyl-propyl}-amide

EXAMPLE 7

2R-[(Formyl-hydroxy-amino)-methyl]-hexanoic acid

{2,2-dimethyl-1S-[4-(2-oxo-2,3-dihydro-benzoimidazol-1-yl)piperidine-1-carbonyl]-pr opyl)amide

EXAMPLE 8

2R-[(Formyl-hydroxy-amino)-methyl]-hexanoic acid

[1S-(4-benzoyl-piperidine-1–Carbonyl)-2,2-dimethyl-propyl]-amide

EXAMPLE 9

2R-[(Formyl-hydroxy-amino)methyl]-hexanoic acid

[1S-(4-benzhydryl-piperazine-1-carbonyl)-2,2-dimethyl-propyl]-amide

EXAMPLE 10

2R-[(Formyl-hydroxy-amino)-methyl]-hexanoic acid

{1S-[4-(2,5-dimethyl-phenyl)-piperazine-1-carbonyl]-2,2-dimethyl-propyl}-amide

EXAMPLE 11

2R-[(Formyl-hydroxy-amino)methyl]-hexanoic acid

{1S-[4-(2-methoxy-phenyl)-piperazine-1-carbonyl]-2,2-dimethyl-propyl}-amide

EXAMPLE 12

2R-[(Formyl-hydroxy-amino)methyl]-hexanoic acid

{1S-[4-(furan-3-carbonyl)-piperazine-1-carbonyl]-2,2-dimethyl-propyl}-amide

EXAMPLE 13

2R-[(Formyl-hydroxy-amino)-methyl]-hexanoic acid

{1S-[4-(5-furan-2-yl-2H-pyrazol-3-yl)piperidine-1-carbonyl]-2,2-dimethyl-propyl}-amide

EXAMPLE 14

2R-[(Formyl-hydroxy-amino)-methyl]-hexanoic acid

{2,2-dimethyl-1S-[4-(5phenyl-2H-pyrazol-3-yl)-piperidine-1-carbonyl]-propyl}-amide

EXAMPLE 15

2R-[(Formyl-hydroxy-amino)-methyl]-hexanoic acid

{1S-[4-(4-methoxy-phenyl)-3-methyl-piperazine-I-carbonyl]-2,2-dimethyl-propyl}-amide

EXAMPLE 16

2R-[(Formyl-hydroxy-amino)-methyl]-hexanoic acid

{1S-[1-(3,4-dimethoxy-benzyl)-6,7-dimethoxy-3,4-dihydro-1H-isoquinoline-2-carbonyl ]-2,2-dimethyl-propyl}-amide

EXAMPLE 17

2R-[(Formyl-hydroxy-amino)-methyl]-hexanoic acid (1S-{4-[5(2-chloro-phenyl)-2H-pyrazol-3yl]-piperidine-1-carbonyl}-2,2-dimethyl-prop yl)-amide

EXAMPLE 18

N-Hydroxy-N-[2R-(4-pyrimidin-2-yl-piperazine-1-carbonyl)-hexyl]-formamide

EXAMPLE 19

N-2R-[4-(4-Chloro-phenyl)-piperazine-1-carbonyl)-hexyl}-N-hydroxy-formamide

EXAMPLE 20

N-[2R-(4-benzo[1,3]dioxol-5-ylmethyl-piperazine-1-carbonyl)-hexyl]-N-hydroxy-formamide

EXAMPLE 21

N-Hydroxy-N-{2R-[4-(4-methoxy-phenyl)-3-methyl-piperazine-1-carbonyl]-hexyl}-formamide

EXAMPLE 22

N-{2R-[4-(4-Acetyl-phenyl)-piperazine-1-carbonyl]-hexyl)-N-hydroxy-formamide

EXAMPLE 23

N-[2R-(4-Benzhydryl-piperazine-1-carbonyl)-hexyl]-N-hydroxy-formamide

EXAMPLE 24

N-Hydroxy-N-[2R-(4-phenyl-piperidine-1-carbonyl)-hexyl]-formamide

EXAMPLE 25

N-Hydroxy-N-2R-[4-hydroxy-diphenyl-methyl)-piperidine-1-carbonyl]-hexyl}-formamide

EXAMPLE 26

N-Hydroxy-N-[2R-(4-phenyl-piperazine-1-carbonyl)-hexyl]-formamide

EXAMPLE 27

N-(2R-{4-[(4-Chloro-phenyl)-phenyl-methyl]-piperazine-1-carbonyl}-hexyl)-N-hydroxy-for mamide

EXAMPLE 28

N-{2R-[4-(3–Chloro-phenyl)-piperazine-1-carbonyl]-hexyl}-N-hydroxy-formamide

EXAMPLE 29

N-Hydroxy-N-(2R-{4-[2-(2-hydroxy-ethoxy)-ethyl]-piperazine-1-carbonyl}-hexyl)-formamide

EXAMPLE 30

N-Hydroxy-N-{2R-[4-(3-hydroxy-propyl)-piperazine-1-carbonyl]-hexyl}-formamide

EXAMPLE 31

N-Hydroxy-N-{2R-[2-(2-hydroxy-ethyl)-piperazine-1-carbonyl]-hexyl}-formamide

EXAMPLE 32

N-{2R-[4-(3,4-Dichloro-phenyl)-piperazine-1-carbonyl]-hexyl}-N-hydroxy-formamide

EXAMPLE 33

N-Hydroxy-N-{2R-[4-(4-methoxy-phenyl)-piperazine-1-carbonyl]-hexyl}-formamide

EXAMPLE 34

N-Hydroxy-N-{2R-[4-(3-trifluoromethyl-pyridin-2-yl)-piperazine-1-carbonyl]-hexyl}-formamide

EXAMPLE 35

N-Hydroxy-N-{2R-[4-(1H-indol-7-yl)-piperazine-1-carbonyl]-hexyl}-formamide

EXAMPLE 36

N-(2R-{4-[Bis-(4-fluoro-phenyl)-methyl]-piperazine-1-carbonyl}-hexyl)-N-hydroxy-formamide

EXAMPLE 37

N-Hydroxy-N-{2R-[4-(4-nitro-phenyl)-piperazine-1-carbonyl]-hexyl}-formamide

EXAMPLE 38

N-{2R-[4-(4-Fluoro-phenyl)-piperazine-1-carbonyl]-hexyl}-N-hydroxy-formamide

EXAMPLE 39

N-{2R-[4-(Furan-2-carbonyl)-piperazine-1-carbonyl]-hexyl}-N-hydroxy-formamide

EXAMPLE 40

N-{2R-[4-(2,5-Dimethyl-phenyl)-piperazine-1-carbonyl]-hexyl}-N-hydroxy-formamide The compounds of Examples 41 and 42 below were prepared in solution by parallel synthesis. The general synthetic route (Scheme B) is outlined in detail below for Example 41. 2R-Cyclopentylmethyl-succinic acid 4-tert-butyl ester was prepared by analogy with methods in patent application number WO 92/13831

EXAMPLE 41

The preparation of 3R-Cyclopentylmethyl-4-[4-(4-fluoro-phenyl)-piperazin-1-yl]-N-hydroxy-4-oxo-butyramide Step A: 3R-Cyclopentylmethyl-4-[4-(4-fluoro-phenyl)-piperazin-1-yl]-4-oxo-butyric acid tert-butyl ester To a solution of 2R-Cyclopentylmethyl-succinic acid 4-tert-butyl ester 1 (250 mg, 1.0 mmol) in dichloromethane (5 ml) was added PyBOP (670 mg, 1.3 mmol), HOAt (145 mg, 1.0 mmol), DIPEA (278 µl, 1.7 mmol) and amine (211 mg, 1.2 mmol), the reaction mixture was stirred at room temperature for 24 h. The solvent was removed in vacuo to yield an orange oil (800 mg), which was taken up in ethyl acetate (50 ml) and was washed with 1M sodium carbonate (2×50 ml), water (1×50 ml) and dried over anhydrous magnesium sulphate. The solvent was removed in vacuo to yield the title compound as a yellow oil (600 mg), which was purified by preparative HPLC.

Step B: 3R-Cyclopentylmethyl-4-[4-(4-fluoro-phenyl)-piperazin-1-yl]-4-oxo-butyric acid To a solution of 3R-Cyclopentylmethyl-4-[4-(4-fluoro-phenyl)-piperazin-1-yl]-4-oxo-butyric acid tert-butyl ester in dichloromethane (3 ml) was added TFA (2 ml) at 0° C., the reaction mixture was stirred at 0° C. for 0.5 h and at room temperature for 1.5 h, after which time no starting material remained. The solvent was removed in vacuo and the TFA was azeotroped with toluene to yield the tite compound as an orange oil (364 mg), which was progressed to the next step without further purification.

Step C: 3R-Cyclopentylmethyl-4-[4-(4-fluoro-phenyl)-piperazin-1-yl]-N-hydroxy-4-oxo-butyramide To a solution of 3R-Cyclopentylmethyl-4-[4-(4-fluoro-phenyl)-piperazin-1-yl]4-oxo-butyric acid (364 mg, 1.0 mmol) in dichloromethane (3 ml) was added PyBOP (575 mg, 1.1 mmol), HOAt (14 mg, 0.1 mmol), and $Et_3N$ (279 µl, 2.0 mmol). To a solution of hydroxylamine hydrochloride (105 mg, 1.5 mmol) in a separate flask in DMF (2 ml) was Scheme B

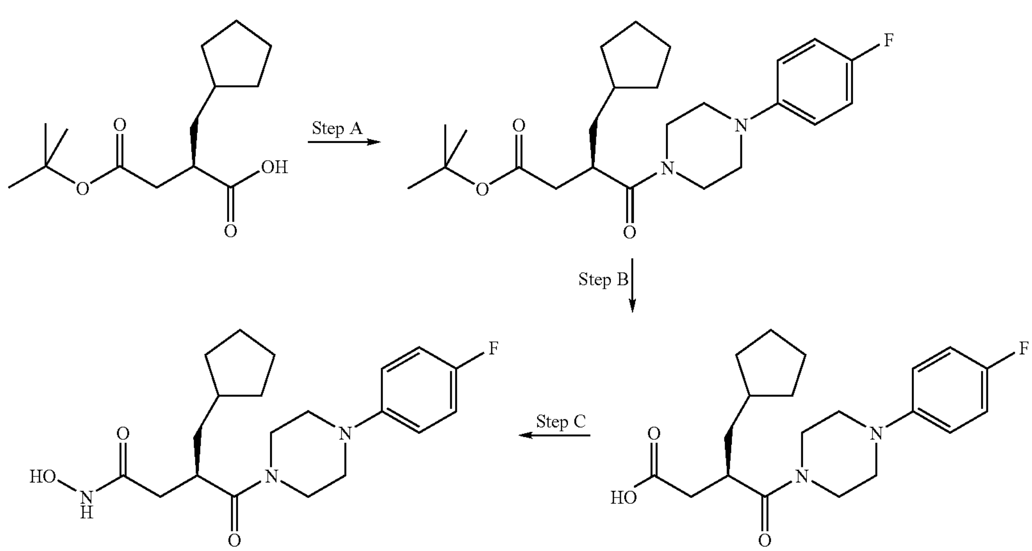

added NMM (161 µl, 1.5 mmol). This solution was then added to the solution of acid and the reaction mixture was stirred at RT for 60 h. The solvent was removed in vacuo and the resulting residue was taken up in dichloromethane (5 ml) and was washed with 1 M sodium carbonate (1×5 ml), water (1×5 ml) dried over anhydrous magnesium sulphate and the solvent removed in vacuo to yield a yellow oil (520 mg). The product was purified by prep HPLC. LRMS −ve ion: 376 (M−1, 80%), P; +ve ion 345 ([M+1]−32, 40%), P-NHOH; HPLC data: RT 5.6 min 97%

The following compound was prepared in a manner identical to that of Example 41 starting with 2R-Cyclopentylmethyl-succinic acid 4-tert-butyl ester and 3,4-dichlorophenyl-piperazine.

EXAMPLE 42

3R-Cyclopentylmethyl-4-[4-(3,4-dichloro-phenyl)-piperazin-1-yl]-N-hydroxy4-oxo-butyramide

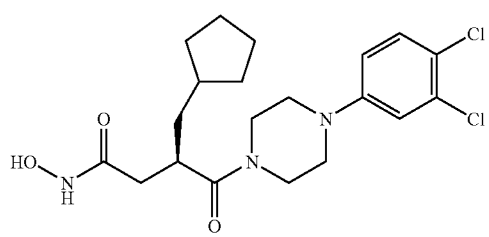

The title compound was purified by preparative HPLC. LRMS −ve ion: 326 (M−1, 40%); +ve ion: 395 ([M+1]−32, 40%), P-NHOH; HPLC data: RT 6.4 min, 98%.

EXAMPLE 43

2R-[(Formyl-hydroxy-amino)-methyl]-hexanoic acid {1S-[4-(4-cyano-benzyl)-piperazine-1-carbonyl]-2,2-dimethyl-propyl}-amide

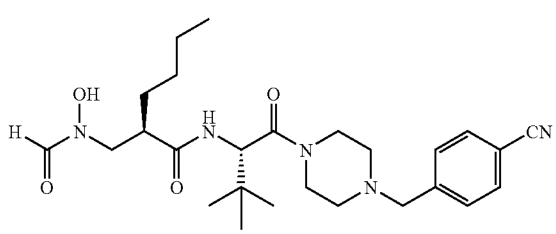

The title compound was prepared as detailed below (see Scheme 2) from 2R-[(Benzoyloxy-formylamino)-methyl]-hexanoic acid (see Scheme 1).

Scheme 2

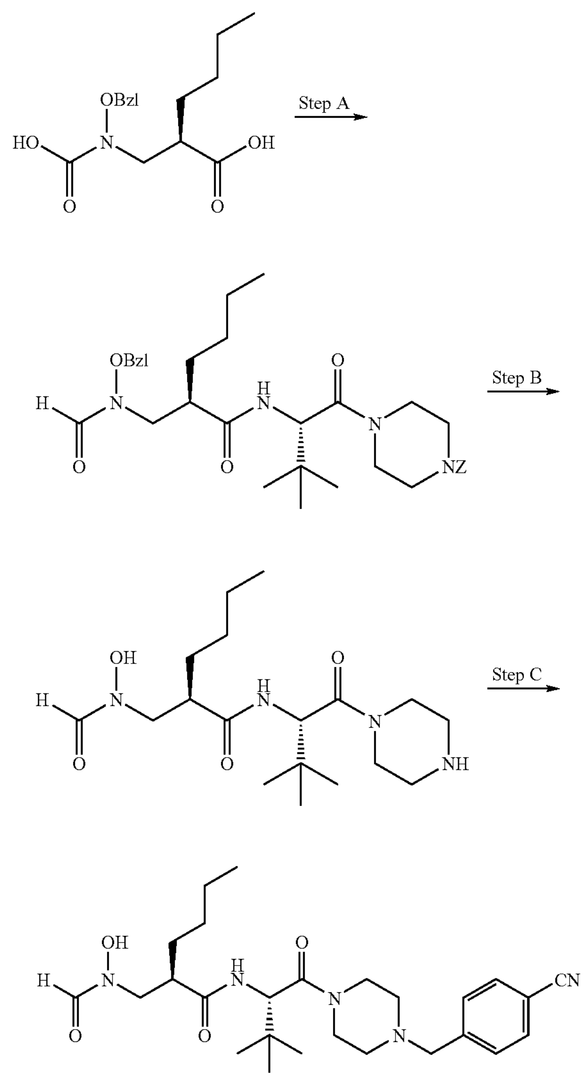

Step A: 2R-[(Benzyloxy-formyl-amino)-methyl]-hexanoic acid {2,2-dimethyl-1S-[4-(2-phenoxy-acetyl)-piperazine-1-carbonyl]-propyl}-amide To a solution of 2R-[(Benzoyloxy-formylamino)-methyl]-hexanoic acid (7.0 g, 25 mmols) in DMF was added EDC (5.3 g, 27.5 mmol), 4-(2S-Amino-3,3-dimethyl-butyryl)-piperazine-1-carboxylic acid benzyl ester (10.0 g, 30 mmol) and HOAt (0.34 g, 2.5 mmol). The reaction was stirred overnight at room temperature. The solvent was removed in vacuo and the residue was dissolved in ethyl acetate, washed successively with 1M hydrochloric acid, 1M sodium carbonate and saturated sodium chloride solution, dried over anhydrous magnesium sulfate and filtered. The solvent was removed in vacuo to yield a yellow oil (9.6 g) that was purified by flash chromatography (3% methanol/DCM) to yield a white foam (6.7 g, 45%). $^1$H-NMR; δ ($CDCl_3$, rotamers), 8.13 (0.6H, s), 7.89 (0.4H, s), 7.36 (10H, m), 6.26 (1H, d, J=9.2 Hz), 5.15 (2H, s), 4.88 (2H, m), 4.82 (1H, d, J=9.3 Hz), 3.56 (10H, m), 2.54 (1H, m), 1.25 (6H, m), 0.94 (9H, s), 0.83 (3H, t, J=6.9 Hz). LRMS: +ve ion 617 [M+Na].

Step B: 2R-[(Formyl-hydroxy-amino)-methyl]-hexanoic acid [2,2-dimethyl-1S-(piperazine-1-carbonyl)-propyl]-amide To a solution of 2R-[(Benzyloxy-formyl-amino)-methyl]-hexanoic acid {2,2-dimethyl-1S-[4-(2-phenoxy-acetyl)piperazine-1-carbonyl]-propyl}-amide (6.5 g, 11 mmol) in ethanol (100 ml), under a blanket of argon, was added a suspension of 10% palladium on charcoal (670 mg) in ethyl acetate (15 ml). Hydrogen was bubbled through the suspension for 30 minutes and then the reaction was stirred under an atmosphere of hydrogen for 3 hours 45 minutes. The palladium catalyst was filtered off and the solvent removed in vacuo to yield a white foam (4.28 g. 100%). $^1$H-NMR; δ ($CDCl_3$, rotamers), 8.39 (0.3H, s), 7.80 (0.7H, s), 6.82 (1H, m), 4.90 (1H, m), 3.87 (3H, m), 3.50 (3H, m), 2.80 (5H, m), 1.39 (6H, m), 0.99 (3H, s), 0.95 (6H, s), 0.87 (3H, t, J=6.7 Hz). LRMS +ve ion 397 [M+1], 419 [M+Na], −ve ion 395 [M−1].

Step C: 2R-[(Formyl-hydroxy-amino)-methyl]-hexanoic acid {1S-[4-(4-cyano-benzyl)-piperazine-1-carbonyl]-2,2-dimethyl-propyl}-amide To a stirred solution of 2R-[(Formyl-hydroxy-amino)-methyl]-hexanoic acid [2,2-dimethyl-1S-(piperazine-1-carbonyl)-propyl]-amide in dichloromethane (4 ml) was added triethylamine (85 μl, 0.6 mmol) and fpnitrile benzyl bromide (110 mg, 0.56 mmol). The reaction mixture was stirred at room temperature overnight. The solvent was removed in vacuo to yield a yellow oil that was purified by preparative HPLC to obtain a white foam (108 mg, 44%) Characterisation data is provided in Table 2.

The compounds of Examples 44–48 were prepared by the synthetic route outlined in Scheme 2 and as described in detail for Example 43. Step C was carried out in parallel for all examples. Characterisation data for the compounds is provided in Table 2. Examples 49–54 were prepared from 2R-[(Benzyloxy-formyl-amino)-methyl]-3-cyclopentyl-propionic acid in a similar manner. Characterisation data for the compounds is provided in Table 3. L-tert-leucine derivatives were prepared according to established literature methods. Purification of the final compounds, where necessary, was carried out by preparative HPLC.

TABLE 2

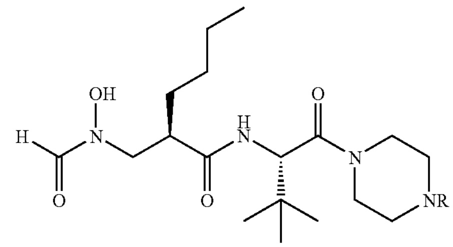

| Example | R= | LCMS ions seen | LCMS Retention time (min) | LCMS Purity (%) |
|---|---|---|---|---|
| 43 | 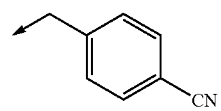 | M + 1 = 486<br>M + Na = 508 | 2.6 | >90 |
| 44 | 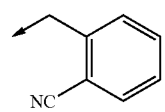 | M + 1 = 486<br>M + Na = 508 | 2.65 | >90 |
| 45 | 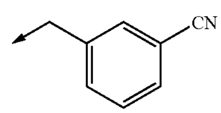 | M + 1 = 486<br>M + Na = 508 | 2.6 | >90 |
| 46 | 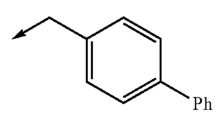 | M + 1 = 537<br>M + Na = 559 | 3.65 | >90 |
| 47 | 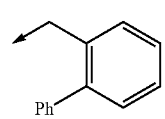 | M + 1 = 537<br>M + Na = 559 | 3.58 | >90 |
| 48 | 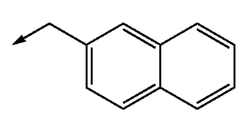 | M + 1 = 511<br>M + Na = 533 | 3.38 | >90 |

TABLE 3

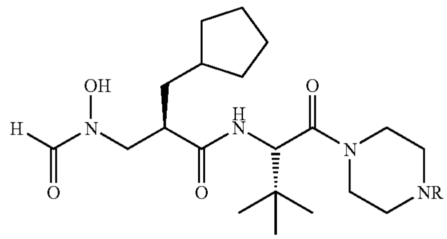

| Example | R = | LCMS ions seen | LCMS Retention time (mins) | LCMS Purity (%) |
|---|---|---|---|---|
| 49 | 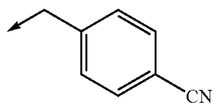 | M + 1 = 512<br>M + Na = 534 | 2.97 | >90 |
| 50 | 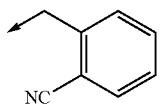 | M + 1 = 512<br>M + Na = 534 | 3.02 | >90 |
| 51 | 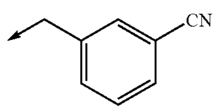 | M + 1 = 512<br>M + Na = 534 | 2.95 | >90 |
| 52 | 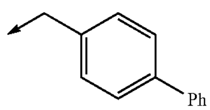 | M + = 563 | 3.88 | >90 |
| 53 | 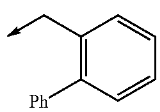 | M + 1 = 563<br>M + Na = 585 | 3.83 | >90 |
| 54 | 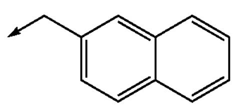 | M + 1 = 537<br>M + Na = 559 | 3.63 | >90 |

The compounds of examples 44–54 are named as follows:

EXAMPLE 44

2R-[(Formyl-hydroxy-amino)-methyl]-hexanoic acid {1S-[4-(2-cyano-benzyl)-piperazine-1-carbonyl]-2,2-dimethyl-propyl}-amide

EXAMPLE 45

2R-[(Formyl-hydroxy-amino)-methyl]-hexanoic acid (1S-[4-(3-cyano-benzyl)-piperazine-1-carbonyl]-2,2-dimethyl-propyl}-amide

EXAMPLE 46

2R-[(Formyl-hydroxy-amino)-methyl]-hexanoic acid [1S-(4-biphenyl-4-ylmethyl-piperazine-1-carbonyl)-2,2-dimethyl-propyl]-amide

EXAMPLE 47

2R-[(Formyl-hydroxy-amino)-methyl]-hexanoic acid [1S-(4-biphenyl-2-ylmethyl-piperazine-1-carbonyl)-2,2-dimethyl-propyl]-amide

EXAMPLE 48

2R-[(Formyl-hydroxy-amino)-methyl]-hexanoic acid [2,2-dimethyl-1S-(4-naphthalen-2-ylmethyl-piperazine-1-carbonyl)propyl]-amide

EXAMPLE 49

N-{1S-[4-(4-Cyano-benzyl)-piperazine-1-carbonyl]-2,2-dimethyl-propyl}-2R-cyclopentylmethyl-3-(formyl-hydroxy-amino)-propionamide

EXAMPLE 50

N-{1S-[4-(2-Cyano-benzyl)-piperazine-1-carbonyl]-2,2-dimethyl-propyl}-2R-cyclopentylmethyl-3-(formyl-hydroxy-amino)-propionamide

EXAMPLE 51

N-{1S-[4-(3–Cyano-benzyl)-piperazine-1-carbonyl]-2,2-dimethyl-propyl}-2S-cyclopentylmethyl-3-(formyl-hydroxy-amino)-propionamide

EXAMPLE 52

N-[1S-(4-Biphenyl-4-ylmethyl-piperazine-1-carbonyl)-2,2-dimethyl-propyl]-2R-cyclopentylmethyl-3-(formyl-hydroxy-amino)-propionamide

EXAMPLE 53

N-[1S-(4-Biphenyl-2-ylmethyl-piperazine-1-carbonyl)2,2-dimethyl-propyl]-2R-cyclopentylmethyl-3-(formyl-hydroxy-amino)-propionamide

EXAMPLE 54

2R-Cyclopentylmethyl-N-[2,2-dimethyl-1S-(4-naphthalen-2-ylmethyl-piperazine-1-carbonyl)-propyl)-3-(formyl-hydroxy-amino)-propionamide

EXAMPLE 55

2R-[(Formyl-hydroxy-amino)-methyl]-hexanoic acid {1S-[4-(3a,7a-dihydro-benzo[1,3]dioxole-5-carbonyl)-piperazine-1-carbonyl]-2,2-dimethyl-propyl}-amide

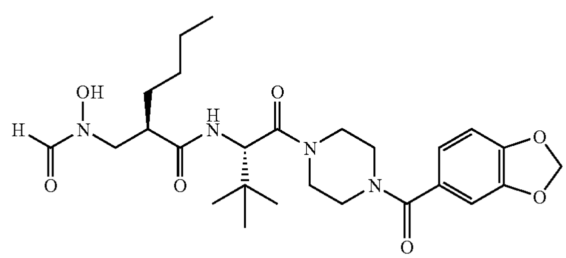

Example 55 was prepared from 2R-[(Benzoyloxy-formylamino)-methyl]-hexanoic acid by analogy with methods described in Scheme 1. 2-Amino-1S-[4-(3a,7a-dihydrobenzo[1,3]dioxole-5-carbonyl)-piperazin-1-yl]-3,3-dimethyl-butan-1-one was prepared as detailed below (Scheme 3).

Scheme 3

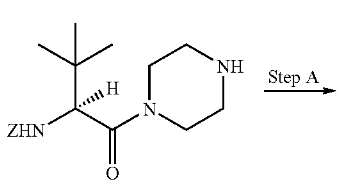

-continued

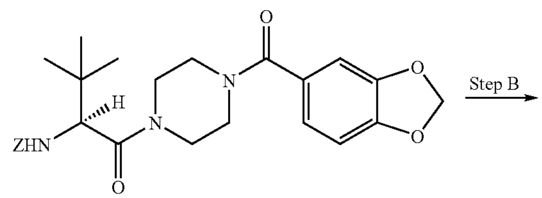

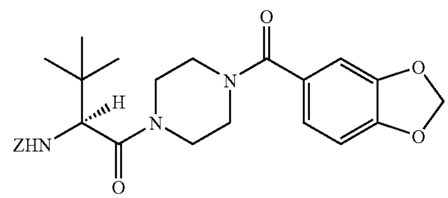

Reagents and conditions: $Et_3N$, 3,4 methlenedioxybenzol chloride, $CH_2Cl_2$ B. Pd/C, EtOH, $H_2(g)$.

Step A: {1S-[4-(3a,7a-Dihydro-benzo[1,3]dioxole-5-carbonyl)-piperazine-1-carbonyl]-2,2-dimethyl-propyl)-carbamic acid benzyl ester To a solution of [2,2-Dimethyl-1S-(piperazine-1-carbonyl)propyl]-carbamic acid benzyl ester (3.2 g, 9.6 mmol) in anhydrous dichloromethane (50 ml) under an atmosphere of argon, was added triethylamine (2.8 ml, 20 mmol) and 3,4 methylenedioxybenzoyl chloride (2.0 g, 10.8 mmol). The reaction was stirred overnight at room temperature. The reaction mixture was diluted with dichloromethane, washed successively with 1 M hydrochloric acid, 1 M sodium carbonate and saturated sodium chloride solution, dried over anhydrous magnesium sulfate and filtered. The solvent was removed in vacuo to yield a yellow oil which was purified by flash chromatography (5% methanol/dichloromethane) to obtain a white foam (3.5 g, 76%). LRMS: +ve ion 504 [M+Na], $^1$H-NMR; δ ($CDCl_3$), 7.35 (5H, s), 6.93 (2H, m), 6.84 (1H, m), 6.01 (2H, s), 5.55 (1H, d, J=9.5 Hz), 5.06 (2H, m), 4.54 (1H, d, J=9.7 Hz), 3.65 (8H, m), 0.99 (9H, s).

Step B: 2-Amino-1S-[4-(3a,7a-dihydro-benzo[1,3]dioxole-5-carbonyl)-piperazin-1-yl]-3,3-dimethyl-butan-1-one To a solution of {1S-[4-(3a,7a-Dihydro-benzo[1,3]dioxole-5-carbonyl)-piperazine-1-carbonyl]-2,2-dimethyl-propyl}-carbamic acid benzyl ester (3.5 g, 7.3 mmol) in ethanol (70 ml), under a blanket of argon, was added 10% palladium on charcoal (350 mg). Hydrogen was bubbled through the suspension for 1 hour and then the reaction was stirred under an atmosphere of hydrogen for 2 hours. The palladium catalyst was filtered off and the solvent removed in vacuo to yield a white foam (2.5 g. 99%). LRMS: +ve ion 348 [M+1], 370 [M+Na], $^1$H-NMR; δ ($CDCl_3$), 6.94 (2H, m), 6.84 (1H, m), 6.01 (2H, s), 3.64 (9H, m), 1.61 (2H, s), 0.98 (9H, s).

The following example 56 was prepared in a similar way to Example 55 except 3,4 methylenedioxybenzoyl chloride was replaced with 3-(bromomethyl) pyridine.

EXAMPLE 56

2R-[(Formyl-hydroxy-amino)-methyl]-hexanoic acid [2,2-dimethyl-1S-(4-pyridin-3-ylmethyl-piperazine-1-carbonyl)-propyl]-amide

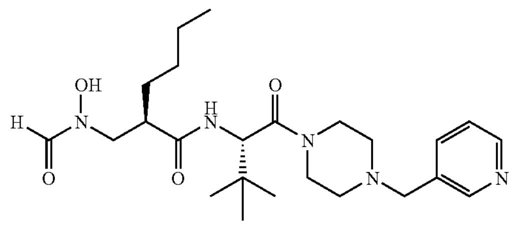

$^1$H-NMR; δ ($CDCl_3$, rotamers), 8.62 (2H, m), 8.39 (0.4H, s), 7.82 (0.6H, s), 7.67 (1H, d, J=7.7 Hz), 7.28 (1H, m), 6.92 (0.4H, m), 6.76 (0.6H, m), 4.91 (1H, m), 4.02 (0.4H, m), 3.82 (3H, m), 3.51 (4.6H, m), 2.84 (06H, m), 2.68 (0.4H, m), 2.36 (4H, m), 1.53 (2H, m), 1.25 (4H, m), 0.97 (3H, s), 0.93 (6H, s), 0.88 (3H, t, J=7.0 Hz). $^{13}$C-NMR; δ (CDCl3), 175.5, 173.3, 170.3, 170.2, 150.6, 149.1, 147.2, 133.6, 123.9, 66.2, 60.3, 54.8, 54.5, 53.7, 53.5, 53.4, 53.3, 53.1, 52.9, 52.8, 52.5, 48.9, 47.3, 47.1, 46.1, 45.1, 2.5 and 42.4. LRMS: +ve ion 484 [M+Na].

EXAMPLE 57

N-[1S-(4-Benzo[1,3]dioxol-5-ylmethyl-piperazine-1-carbonyl)-2,2-dimethyl-propyl]-2R-cyclopentylmethyl-3-(formyl-hydroxy-amino)-propionamide

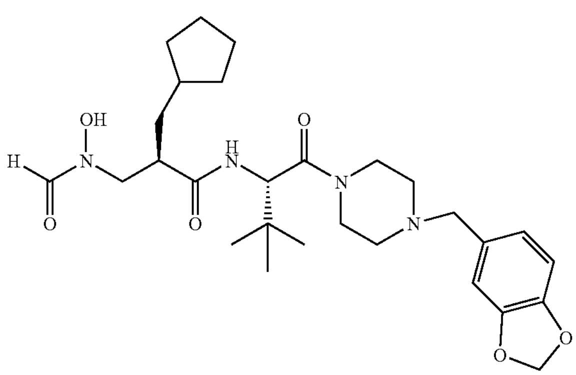

The title compound was prepared as detailed in scheme 1 from 2S-Amino-1-(4-benzo[1,3]dioxol-5-ylmethyl-piperazin-1-yl)-3,3-dimethyl-butan-1-one (see scheme 3, piperonyl piperazine is commerically available) and 2R-Cyclopentylmethyl-3-(formyl-hydroxy-amino)-propionic acid pentafluorophenyl ester.

$^1$H-NMR; δ ($CDCl_3$, rotamers), 8.40 (0.4H, bs), 7.82 (0.6H, bs), 6.83 (1H, bs), 6.76–6.63 (2H, m), 6.58–6.54 (1H, m), 5.94 (2H, s), 4.87 (1H, m), 4.10–3.28 (9H, M), 2.87–2.16 (7H, m), 1.85–1.33 (10H, m); 1.09 (1H, m); 0.98 (3.6H, m); 0.93 (5.4H, m); LRMS: +ve ion 531 [M+H], 553 [M+Na]. −ve ion 529 [M−1]; HPLC: RT=4.91 min, 97% pure.

Examples 58–67 were prepared by synthetic methods analogous to those described for Example 55, using the relevant acid chloride or carboxylic acid in Step A of Scheme 3. The compounds were synthesised in parallel and purification of the final compounds, where necessary, was carried out by preparative HPLC.

Characterisation data for these compounds are provided in Table 4.

Examples 68–79 were prepared by synthetic methods analogous to those described for Example 43, but using an acid chloride, carboxylic acid or sulfonyl chloride in place of the bromide in Step C of Scheme 2. Purification of the final compounds, where necessary, was carried out by preparative HPLC. Characterisation data for these compounds are provided in Table 5.

TABLE 4

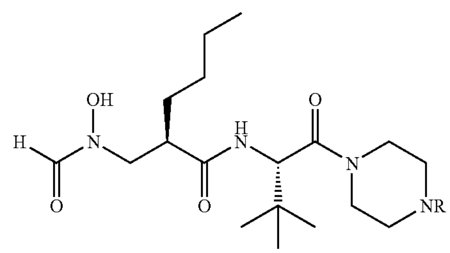

| Example | R= | Mass Spec. | HPLC Retention time | HPLC Purity (%) |
|---|---|---|---|---|
| 58 | 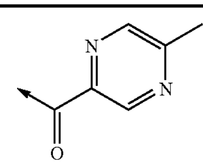 | M + Na = 513 | 4.9 | >84 |
| 59 | 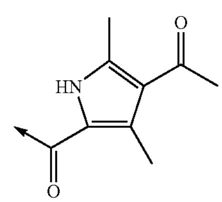 | M + Na = 556 | 5.1 | >87 |
| 60 | 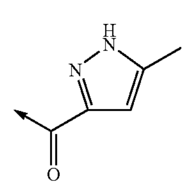 | M + Na = 501 | 4.8 | >84 |
| 61 | 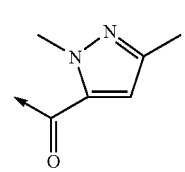 | M + Na = 515 | 5 | >85 |

TABLE 4-continued
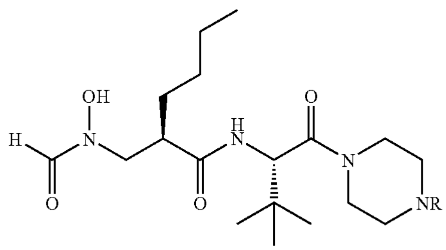
| Example | R= | Mass Spec. | HPLC Retention time | HPLC Purity (%) |
|---|---|---|---|---|
| 62 | 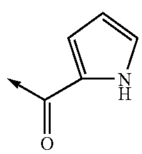 | M + Na = 486 | 5.1 | >83 |
| 63 | 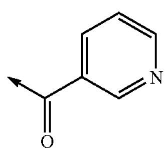 | M + Na = 498 | 3.8 | >95 |
| 64 | 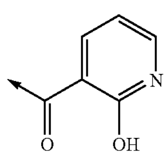 | M + Na = 514 | 4.4 | 98 |
| 65 | 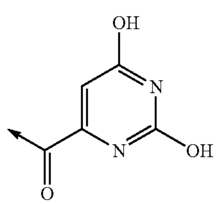 | M + Na = 531 | 4.5 | 93 |
| 66 | 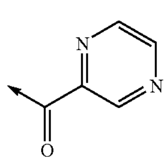 | M + Na = 499 | 7.8 | >96 |
| 67 | 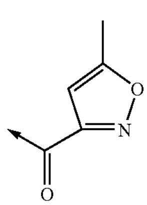 | M + Na = 502<br>M − 1 = 478 | 10.4 | 92 |
TABLE 5
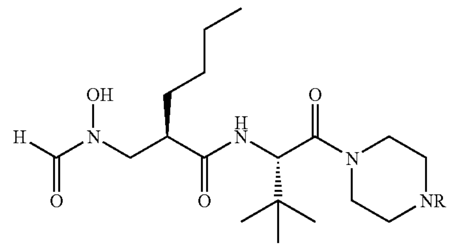
| Example | R= | Mass Spec. | HPLC Retention time | HPLC Purity (%) |
|---|---|---|---|---|
| 68 | 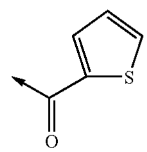 | M + Na = 503<br>M − 1 = 479 | 4.9 | 100 |
| 69 | 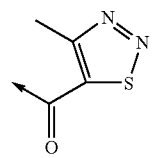 | M + Na = 519<br>M − 1 = 495 | 4.9 | 100 |
| 70 | 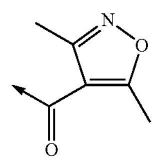 | M + Na = 516<br>M − 1 = 492 | 4.7 | 96 |
| 71 | 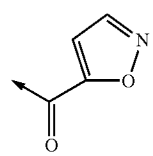 | M + Na = 488<br>M − 1 = 464 | 4.6 | 99 |
| 72 | 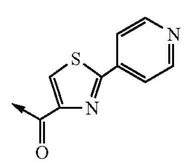 | M + 1 = 559<br>M + Na = 581<br>M − 1 = 557 | 4.5 | >88 |
| 73 | 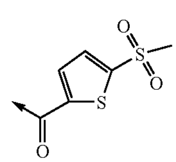 | M + 1 = 559<br>M + Na = 581<br>M − 1 = 557 | 5.2 | 100 |
| 74 | 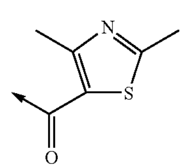 | M + 1 = 510<br>M + Na = 532<br>M − 1 = 508 | 5 | >95 |
| 75 | 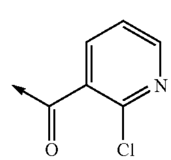 | M + Na = 532 | 4.96 | 99 |

TABLE 5-continued

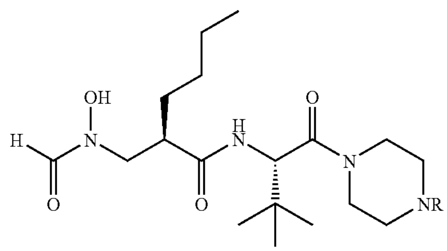

| Example | R= | Mass Spec. | HPLC Retention time | HPLC Purity (%) |
|---|---|---|---|---|
| 76 | 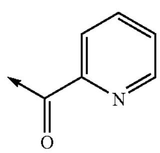 | M + 1 = 476<br>M + Na = 498<br>M − 1 = 474 | 4.77 | 95 |
| 77 | 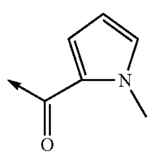 | M + 1 = 478<br>M + Na = 500<br>M − 1 = 476 | 5.09 | 100 |
| 78 | 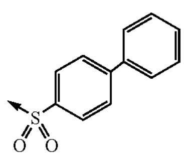 | M + 1 = 587<br>M + Na = 609<br>M − 1 = 585 | 6.08 | 100 |
| 79 | 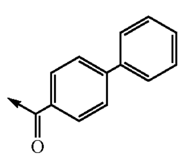 | M + 1 = 551<br>M + Na = 573<br>M − 1 = 549 | 6.01 | 97 |

The compounds of Examples 58–79 are named as follows:

EXAMPLE 58

2R-[(Formyl-hydroxy-amino)-methyl]-hexanoic acid {2,2-dimethyl-1S-[4-(5-methyl-pyrazine-2-carbonyl)-piperazine-1-carbonyl]-propyl}-amide

EXAMPLE 59

2R-[(Formyl-hydroxy-amino)-methyl]-hexanoic acid (1S-[4-(4-acetyl-3,5-dimethyl-H-pyrrole-2-carbonyl)-piperazine-1-carbonyl]-2,2-dimethyl-propyl}-amide

EXAMPLE 60

2R-[(Formyl-hydroxy-amino)-methyl]-hexanoic acid (2,2-dimethyl-1S-[4-(5-methyl-1H-pyrazole-3-carbonyl)-piperazine-1-carbonyl]-propyl}-amide

EXAMPLE 61

2R-[(Formyl-hydroxy-amino)methyl]-hexanoic acid {1S-[4-(2,5-dimethyl-2-H-pyrazole-3-carbonyl)-piperazine-1-carbonyl]-2,2-dimethyl-propyl}-amide

EXAMPLE 62

2R-[(Formyl-hydroxy-amino)methyl]-hexanoic acid {2,2-dimethyl-1S-[4-(1-H-pyrrole-2-carbonyl)-piperazine-1-carbonyl]-propyl}-amide

EXAMPLE 63

2R-[(Formyl-hydroxy-amino)-methyl]-hexanoic acid {2,2-dimethyl-1S-[4-(pyridine-3-carbonyl)-piperazine-1-carbonyl]-propyl}-amide

EXAMPLE 64

2R-[(Formyl-hydroxy-amino)-methyl]-hexanoic acid {1S-[4-(2-hydroxy-pyridine-3-carbonyl)-piperazine-1-carbonyl]-2,2-dimethyl-propyl}-amide

EXAMPLE 65

2R[(Formyl-hydroxy-amino)-methyl]-hexanoic acid {1S-[4-(2,6-dihydroxy-pyrimidine-4-carbonyl)-piperazine-1-carbonyl]-2,2-dimethyl-propyl}-amide

EXAMPLE 66

2R-[(Formyl-hydroxy-amino)-methyl]-hexanoic acid {2,2-dimethyl-1S-[4-(pyrazine-2-carbonyl)piperazine-1-carbonyl]-propyl}-amide

EXAMPLE 67

2R-[(Formyl-hydroxy-amino)-methyl]-hexanoic acid {2,2-dimethyl-1S-[4-(5-methyl-isoxazole-3-carbonyl)-piperazine-1-carbonyl]-propyl}-amide

EXAMPLE 68

2R-[(Formyl-hydroxy-amino)-methyl]-hexanoic acid {2,2-dimethyl-1S-[4-(thiophene-2-carbonyl)-piperazine-1-carbonyl]-propyl}-amide

EXAMPLE 69

2R-[(Formyl-hydroxy-amino)-methyl]-hexanoic acid {2,2-dimethyl-1S-[4-(4-methyl-[1,2,3]thiadiazole-5-carbonyl)-piperazine-1-carbonyl]-propyl}-amide

EXAMPLE 70

2R-[(Formyl-hydroxy-amino)-methyl]-hexanoic acid {1S-[4-(3,5-dimethyl-isoxazoleA-carbonyl)-piperazine-1-carbonyl]-2,2-dimethyl-propyl}-amide

EXAMPLE 71

2R-[(Formyl-hydroxy-amino)-methyl]-hexanoic acid {1S-[4-(isoxazole-5-carbonyl)-piperazine-1-carbonyl]-2,2-dimethyl-propyl}-amide

EXAMPLE 72

2R-[(Formyl-hydroxy-amino)-methyl]-hexanoic acid {2,2-dimethyl-1S-[4-(2-pyridin4-yl-thiazole-4-carbonyl)-piperazine-1-carbonyl]-propyl}-amide

EXAMPLE 73

2R-[(Formyl-hydroxy-amino)-methyl]-hexanoic acid {1S-[4-(5-methanesulfonyl-thiophene-2-carbonyl)-piperazine-1-carbonyl]-2,2-dimethyl-propyl}-amide

EXAMPLE 74

2R-[(Formyl-hydroxy-amino)-methyl]-hexanoic acid {1S-[4-(2,4-dimethyl-thiazole-5-carbonyl)-piperazine-1-carbonyl]-2,2-dimethyl-propyl}-amide

EXAMPLE 75

2R-[(Formyl-hydroxy-amino)-methyl]-hexanoic acid {1S-[4-(2-chloro-pyridine-3-carbonyl)-piperazine-1-carbonyl]-2,2-dimethyl-propyl}-amide

EXAMPLE 76

2R-[(Formyl-hydroxy-amino)-methyl]-hexanoic acid {2,2-dimethyl-1S-[4-(pyridine-2-carbonyl)piperazine-1-carbonyl]-propyl}-amide

EXAMPLE 77

2R-[(Formyl-hydroxy-amino)-methyl]-hexanoic acid {2,2-dimethyl-1S-[4-(1-methyl-1-H-pyrrole-2-carbonyl)-piperazine-1-carbonyl]-propyl}-amide

EXAMPLE 78

2R-[(Formyl-hydroxy-amino)-methyl]-hexanoic acid {1S-[4-(biphenyl-4-sulfonyl)-piperazine-1-carbonyl]-2,2dimethyl-propyl}-amide

EXAMPLE 79

2R-[(Formyl-hydroxy-amino)-methyl]-hexanoic acid {1S-(4-(biphenyl-4-carbonyl)-piperazine-1-carbonyl]-2,2-dimethyl-propyl}-amide Examples 80 and 81 were prepared in a similar manner to Example 43 from 2R-[(Benzyloxy-formyl-amino)-methyl]-3-cyclopentyl-propionic acid.

EXAMPLE 80

2R-[(Formyl-hydroxy-amino)-methyl]-hexanoic acid (2,2-dimethyl-1S-{4-[4-(morpholine-4-carbonyl)-benzyl]-piperazine-1-carbonyl}-propyl)-amide

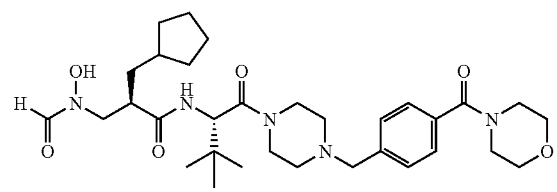

$^1$H-NMR; δ ($CDCl_3$, rotamers), 8.38 (0.4 H, s), 7.81 (0.6H, s), 7.36 (4H, s), 6.77 (0.4H, d, J=8.9 Hz), 6.62 (0.6H, d, J=9.3 Hz), 4.88 (1H, m), 4.03 (0.4H, dd, J=14.6, 7.1 Hz), 3.91 (1H, m), 3.76 (8H, m), 3.51 (5.6H, m), 3.38 (1H, m), 2.84 (0.6H, m), 2.69 (0.4H, m), 2.55 (2H, m), 2.30 (2H, m), 1.57 (9H, m), 1.05 (2H, m), 0.98 (3H, s), 0.94 (6H, s). $^{13}$C-NMR; δ ($CDCl_3$, rotamers), 176.0, 173.3, 170.7, 170.1, 156.5, 140.2, 134.8, 129.5, 127.7, 67.3, 62.8, 55.0, 54.5, 53.8, 53.6, 53.2, 53.1, 52.2, 49.0, 47.4, 47.2, 46.0, 44.9, 42.7, 42.4, 38.5, 38.2, 36.9, 36.7, 35.9, 33.2, 27.0, 25.6 and 25.5. LRMS: +ve ion 600 [M+H], 622 [M+Na]. HPLC: RT=4.63 min, 100% pure.

EXAMPLE 81

2R-[(Formyl-hydroxy-amino)-methyl]-hexanoic acid [2,2-dimethyl-1S-(4-pyridin-3-ylmethyl-piperazine-1-carbonyl)-propyl]-amide

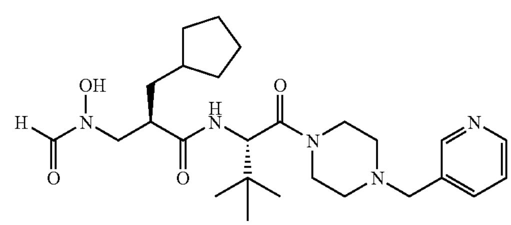

$^1$H-NMR; δ ($CDCl_3$ rotamers), 8.53 (2 H, m), 8.40 (0.3H, s), 7.81 (0.7H, s), 7.65 (1H, d, J=7.7 Hz), 7.27 (1H, m), 6.76 (0.3H, d, J=8.8 Hz), 6.67 (0.7H, d, J=8.9 Hz), 4.89 (1H, m), 4.03 (0.3H, m), 3.92 (1H, m0, 3.77 (1.7H, m) 3.47 (5H, m), 2.86 (0.7H, m), 2.69 (0.3H, m), 2.56 (2H, m0, 2.31 (2H, m), 1.64 (9H, m), 1.07 (2H, m), 0.98 (3H, s), 0.93 (6H, s). $^{13}$C-NMR; δ ($CDCl_3$, rotamers), 175.5, 173.0, 169.8, 150.3, 148.8, 136.7, 133.1, 123.4, 60.0, 54.6, 54.1, 53.4, 53.2, 52.8, 52.7, 52.1, 48.7, 46.9, 46.8, 45.6, 44.5, 42.2, 42.0, 38.2, 37.9, 36.5, 36.3, 35.6, 32.8, 32.7, 6.7, 25.3 and 25.2. LRMS: +ve ion 488 [M+H], 510 [M+Na]. HPLC: RT=4.48 min, 98% pure.

EXAMPLE 82

2R-(Formyl-hydroxy-amino)-methyl]-hexanoic acid {1S-[4-4-hydroxymethyl-phenyl)-piperazine-1-carbonyl]-2,2-dimethyl-propyl}-amide

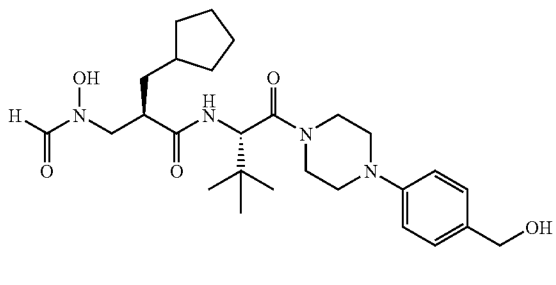

LRMS: +ve ion 485 [M−OH]$^+$, −ve ion 501 [M−H]. HPLC RT=5.8 min, 95% pure.

The title compound was prepared from 3-(Benzyloxy-formyl-amino)-2R-cyclopentylmethyl-propionic acid pentafluoro-phenyl ester and 4-(4-Benzyl-piperazin-1-yl)-benzoic acid ethyl ester which is a known literature compound. {1-[4-(4-Hydroxymethyl-phenyl)-piperazine-1-carbonyl]-2,2-dimethyl-propyl}-carbamic acid benzyl ester (Scheme 4) was deprotected and coupled to the pentafluorophenyl ester in a manner identical to that in Scheme 1.

Scheme 4

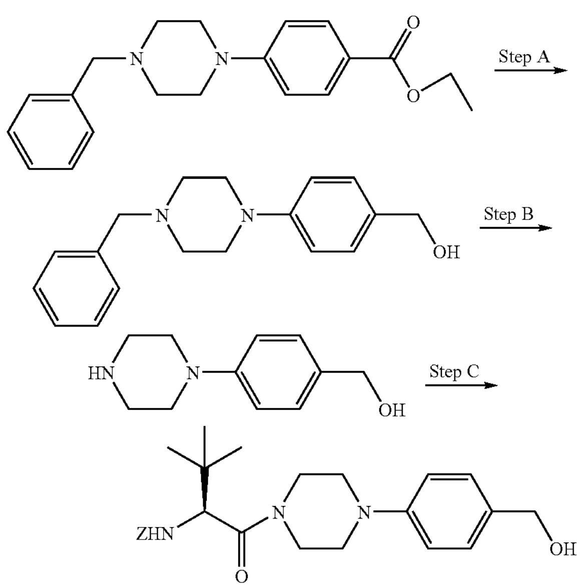

Step A [4-(4-Benzyl-piperazin-1-yl)-phenyl]-methanol

To a solution of lithium aluminium hydride (88 mg, 2.3 mmol) in dry THF (20 ml) was added 4-(4-Benzyl-piperazin-1-yl)-benzoic acid ethyl ester (500 mg, 1.5 mmol). The suspension was stirred at 75° C. for 4 h. The reaction mixture was allowed to cool and a few drops of water were added followed by 1–2 drops of 1M sodium hydroxide. A white precipitate formed and was filtered off, the THF was removed in vacuo, and brine (10 ml) was added to the residue. This mixture was washed with ether (2×50 ml, the ether layers were combined and dried over anhydrous magnesium sulphate and the solvent removed in vacuo to yield a yellow solid (405 mg). Flash chromatography (3% MeOH/$CH_2Cl_2$) allowed the isolation of the title compound as a white solid (331 mg, 76%). $^1$H-NMR δ ($CDCl_3$) 7.38–7.21 (7H, m, ArH), 6.91–6.85 (2H, m, ArH), 4.59 (2H, s), 3.57 (2H, s), 3.21–3.17 (4H, m), 2.61–2.58 (4H, m). HPLC: 2.4 min (99%@214 nm); LRMS +ve: 283 (M+1, 80).

Step B: (4-Piperazin-1-yl-phenyl)-methanol

To a solution of [4-(4-Benzyl-piperazin-1-yl)phenyl]-methanol in EtOH (50 ml) under a blanket of argon was added a suspension of 10% palladium on charcoal (1.5 g) in EtOH (150 ml). Hydrogen was bubbled through the suspension for 1 h and then the reaction mixture was stirred under a blanket of hydrogen for 60 h at RT. The catalyst was filtered off and the solvent removed in vacuo to yield the title compound as a white solid (4.8 g, 100%). $^1$H-NMR δ ($CDCl_3$) 7.30–7.21 (2H, m, ArH), 6.94–6.88 (2H, m, ArH), 4.59 (2H, s), 3.18–2.98 (8H, m). HPLC: 0.5 min (37%@214 nm), 0.7 min (55%@214 nm), multiple peaks due to salt formation from TFA buffer; LRMS +ve: 193 (M+1, 70).

Step C: {1-[4-(4-Hydroxymethyl-henyl)-piperazine-1-carbonyl]-2,2-dimethyl-propyl}-carbamic acid benzyl ester To a solution of CBz protected teit-leucine (7.4 g, 28 mmol) in dichloromethane (20 ml) was added (4-Piperazin-1-yl-phenyl)-methanol in a solution of DMF/dichloromethane (50:50, 250 ml). EDC (7.3 g, 38 mmol), HOAt (0.34 g, 2.5 mmol) and triethylamine (7.0 ml, 50 mmol) were subsequently added. The reaction mixture was stirred at RT for 18 h. The solvent was removed in vacuo to yield a yellow oil, which was taken up in dichloromethane (300 ml) and was washed with 1M sodium carbonate (2×200 ml), 1M hydrochloric acid (1×200 ml), brine (1×200 ml) dried (anhydrous magnesium sulphate) and the solvent removed in vacuo to yield a white foam (11.8 g). Flash chromatography 2% MeOH/dichloromethane allowed the isolation of the title compound as a white foam (7.01 g, 63%). HPLC 5.7 min (100% @ 214 nm). LRMS +ve 462 (M+Na, 60), 440 (M+1, 20), 422 (M−OH, 100).

EXAMPLE 83

2R-[(Formyl-hydroxy-amino)-methyl]-hexanoic acid [2,2-dimethyl-1S-(4-pyrimidin-2-yl-piperazine-1-carbonyl)-propyl]-amide

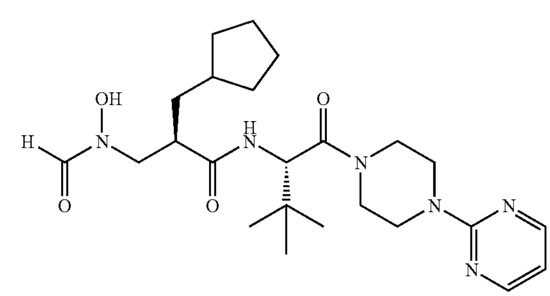

Prepared by method analogous to Example 82.

$^1$H-NMR; δ ($CDCl_3$), 8.40 (0.3H, s), 8.33 (2H, d, J=4.8 Hz), 7.82 (0.7H, s), 6.76 (1H, d, J=8.4 Hz), 6.55 (1H. t, J=4.7 Hz), 4.94 (1H, m), 4.09–3.37 (10H, m), 2.86–2.78 (0.7H, m), 2.72–2.65 (0.3H, m,) 1.63–1.18 (6H, m), 1.02 (3H, s), 0.97 (6H, s), 0.85 (3H, m). $^{13}$C-NMR; δ ($CDCl_3$), 176.0, 173.3, 170.5, 161.9, 158.2, 111.1, 55.3, 54.7, 52.1, 48.7, 47.1, 47.0, 46.5, 45.1, 44.3, 44.2, 44.0, 43.9, 42.6, 42.4, 35.9, 30.3, 30.2, 29.7, 29.6, 27.1, 22.9 and 14.3. LRMS: +ve ion 449 [M+H], 471 [M+Na], −ve ion 447 [M−H]. HPLC: RT=4.99 min, 100% pure.

EXAMPLE 84

$N^1$-{1S-[4-(Benzo[1,3]dioxole-5carbonyl)-piperazine-1-carbonyl]-2,2-dimethyl-propyl}-2R-cyclopentylmethyl-$N^4$-hydroxy-succinamide

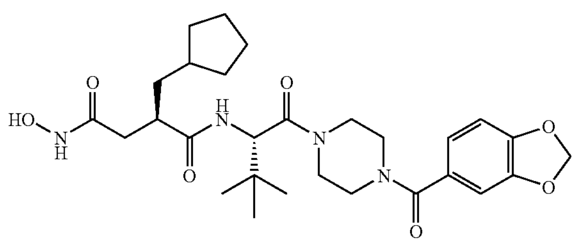

Example 84 was prepared as detailed below (see Scheme 5) from 2R-Cyclopentylmethyl-succinic acid 4-tert-butyl ester, prepared by analogous methods described in patent WO 92/13831, and 2-Amino-1S-[4-(benzo[1,3]dioxole-5-carbonyl)-piperazin-1-yl]-3,3-dimethyl-butan-1-one, prepared by methods described in Scheme 3.

Scheme 5

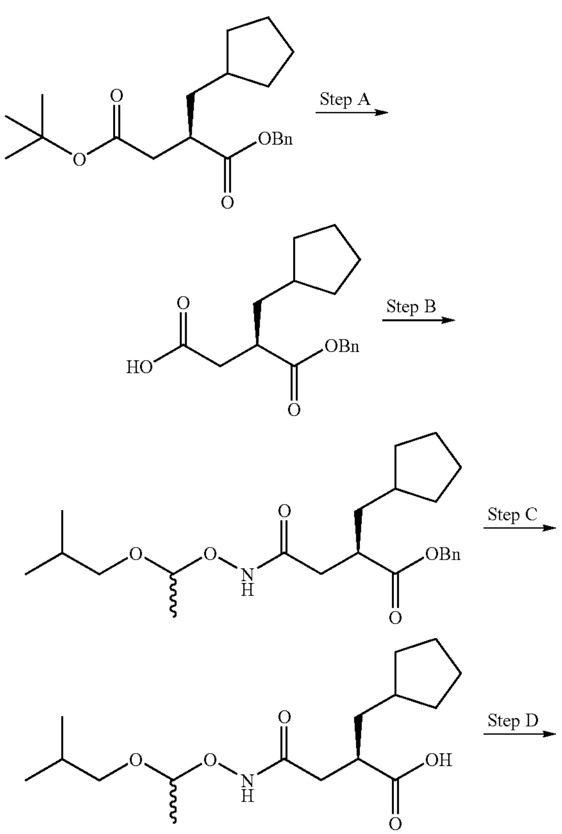

-continued

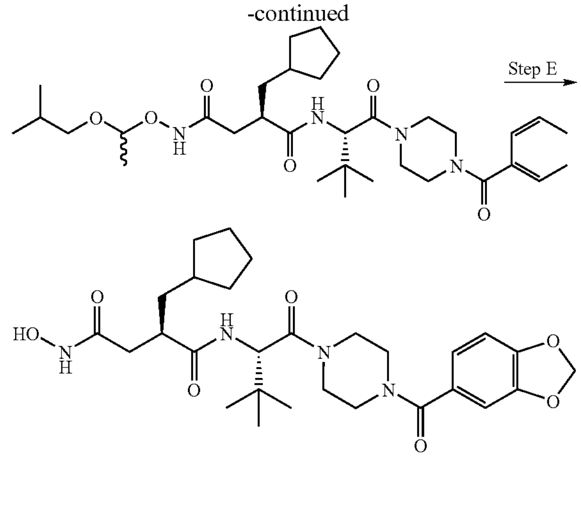

Reagents and conditions: A. TFA, $CH_2Cl_2$; B. EDC, DMF, HOAt, hydroxylamine. C. Pd/C, EtOH, $H_{2(g)}$. D. EDC, DMF. E. MeOH, 1M HCl.

Step A: 2R-Cyclopentylmethyl-succinic acid 1-benzyl ester

To a solution of 2R-Cyclopentylmethyl-succinic acid 4-tert-butyl ester (960 mg, 2.7 mmol) in dichloromethane (30 ml), was added TFA (30 ml). The reaction mixture was left at −4° C. for 18 h. The solvent was removed in vacuo and the TFA co-evaporated with toluene and ether in vacuo to yield a yellow oil (810 mg, 100%). $^1$H-NMR δ ($CDCl_3$), 7.38–7.29 (5H, m), 5.15 (2H, s), 2.93–2.87 (1H, m), 2.78 (1H, dd, $J_1$=9.485 $J_2$=16.81), 2.52 (1H, dd, $J_1$=4.92 $J_2$=17.01), 1.84–1.63 (3H, M), 1.62–1.53 (2H, m), 1.52–1.40 (3H, m), 1.09–1.02 (2H, m).

Step B: 2R-Cyclopentylmethyl-N-(1-isobutoxy-ethoxy)-succinamic acid benzyl ester To a solution of 2R-Cyclopentylmethyl-succinic acid 1-benzyl ester (810 mg, 2.8 mmol) in DMF, was added EDC (805 mg, 4.2 mmol), HOAt, (10% w/w) and O-(1-Isobutoxy-ethyl)-hydroxylamine (745 mg, 5.6 mmol). The reaction was left stirring for 60 h at room temperature. The solvent was removed in vacuo, the residue was taken up in ethyl acetate and washed successively with 1M hydrochloric acid, 1M sodium carbonate and saturated sodium chloride solution. The organic phase was dried over anhydrous magnesium sulfate and concentrated in vacuo to yield a yellow oil (1.07 g, 97%).

$^1$H NMR; δ ($CDCl_3$), 8.05 (1H, bs), 7.34–7.27 (5H, m), 5.17:5.10 (2H, AB q, J=12.36), 4.92–4.88 (1H, m), 3.52 (1H, dd, $J_1$=6.643 $J_2$=9.340), 3.271 (1H, dd, $J_1$=6.734 $J_2$=9.267), 3.06–2.95 (1H, m), 2.52–2.23 (2H, m), 1.89–1.41 (11H, m), 1.36 (3H, dd, $J_1$=3.53 $J_2$=5.303), 1.06 (2H, bs), 0.919. (6H, d, 6.63).

ESMS; +ve ion 428 [M+Na]

Step C: 2R-Cyclopentylmethyl-N-(1-isobutoxy-ethoxy)-succinamic acid

To a solution of 2R-Cyclopentylmethyl-N-(1-isobutoxy-ethoxy)-succinamic acid benzyl ester (925 mg, 2.3 mmol) in ethanol, under a blanket of argon, was added palladium on charcoal (10% w/w). Hydrogen was bubbled through the suspension for 30 minutes and the reaction stirred under an atmosphere of hydrogen for 3 hours. The palladium catalyst was filtered off and the solvent removed in vacuo to yield a yellow oil (720 mg, 100%).

$^1$H-NMR; δ ($CDCl_3$), 4.93 (1H, m), 3.559 (1H, dd, $J_1$=6.620 $J_2$=9.292), 3.292 (1H, dd, $J_1$=6.70 $J_2$=9.330), 2.94 (1H, m), 2.49–2.29 (2H, m), 1.93–1.75 (5H, M), 1.61–1.44 (6H, m), 1.377 (3H, dd, $J_1$=1.237 $J_2$=5.237), 1.08 (2H, m), 0.919 (6H, d, $J_1$=6.65). ESMS; +ve ion 338 [M+Na], −ve ion 314 [M−1]

Step D: $N^1$-{1S-[4-(Benzo[1,3]dioxole-5-carbonyl)-piperazine-1-carbonyl]-2,2-dimethyl-propyl}-2R-cyclopentylmethyl-$N^4$-(1-isobutoxy-ethoxy)-succinamide To a solution of 2R-Cyclopentylmethyl-N-(1-isobutoxy-ethoxy)-succinamic acid (150 mg, 0.48 mmol) in DMF (7.5 ml), was added 2-Amino-1S-[4-(benzo[1,3]dioxole-5-carbonyl)-piperazin-1-yl]-3,3-dimethyl-butan-1-one (165 mg, 0.5 mmol) and stirred for 5 minutes. EDC (96 mg, 0.5 mmol) was added and the reaction mixture stirred at room temperature over the weekend. The solvent was removed in vacuo and the residue taken up in ethyl acetate and washed successively with 1M hydrochloric acid, 1M sodium carbonate and saturated sodium chloride solution. The organic phase was dried over anhydrous magnesium sulfate and concentrated in vacuo to yield an 'off white' solid (227 mg, 74%).

$^1$H-NMR; δ ($CDCl_3$), 6.87 (2H, m), 6.01 (2H, s), 4.873 (1H, m), 3.94–3.67 (4H, m), 3.64–3.23 (10H, m), 2.773 (1H, m), 2.43–2.19 (2H, m), 1.89–1.39 (14H, m), 1.357 (3H. dd, $J_1$=2.350 $J_2$=5.306), 1.117 (2H, m), 0.987 (9H, s), 0.913 (6H, d, $J_1$=6.66).ESMS; +ve ion 667 [M+Na]

Step E: $N^1$-{1S-[4-(Benzo[1,3]dioxole-5-carbonyl)-piperazine-1-carbonyl]-2,2-dimethyl-propyl}-2R-cyclopentylmethyl-$N^4$-hydroxy-succinamide $N^1$-{1S-[4-(Benzo[1,3]dioxole-5-carbonyl)-piperazine-1-carbonyl]-2,2-dimethyl-propyl-2R-cyclopentylmethyl-$N^4$-(1-isobutoxy-ethoxy)-succinamide(198 mg, 0.31 mmol) was dissolved in a 50/50 mixture of methanol and 1M hydrochloric acid (16 ml) and stirred at room temperature for 30 minutes. Pre-washed Amberlyst resin 95 was added until pH 7 was reached and was then filtered under suction and washed with methanol. The filtrate was concentrated in vacuo with ethanol to yield a yellowish solid that was purified by preparative HPLC to yield the title compound as a white foam (62 mg). $^1$H-NMR; δ (MeOD), 6.935 (1H, s), 6.926 (2H, dd, $J_1$=7.854 $J_2$=34.375), 6.018 (2H, s), 4.863 (1H, s), 3.902–3.384 (8H, m), 2.893 (1H, m), 2.323 (1H, dd, $J_1$=7.86 $J_2$=14.31), 2.193 (1H, dd, $J_1$=6.23 $J_2$=14.39), 1.824 (1H, m), 1.645 (5H, m), 1.491 (2H, m), 1.374 (1H, m), 1.033 (11H, m); $^{13}$C-NMR; δ (MeOD), 177.7, 172.8, 172.2, 171.0, 151.3, 149.7, 130.2, 123.3, 109.7, 103.5, 56.5, 48.1, 43.6, 43.4, 40.1, 39.8, 37.4, 36.4, 34.0, 27.5, 26.5; ESMS; +ve ion 567 [M+Na], −ve ion 543 [M−1]

PREPARATIVE EXAMPLE A

2R-Cyclopentylmethyl-$N^1$-{2,2-dimethyl-1S-[4-(4-methyl-benzyl)-piperazine-1-carbonyl]-propyl}-$N^4$-hydroxy-succinamide

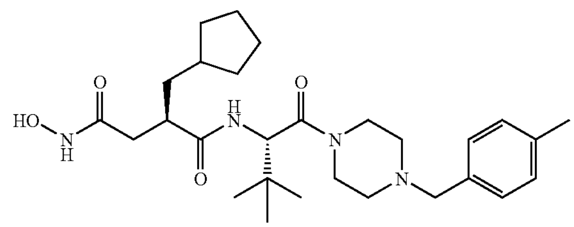

The title compound was prepared as detailed below (see scheme 6) from 2-Cyclopentylmethyl-N-(1-isobutoxy-ethoxy)succinamic acid (scheme 5).

Scheme 6

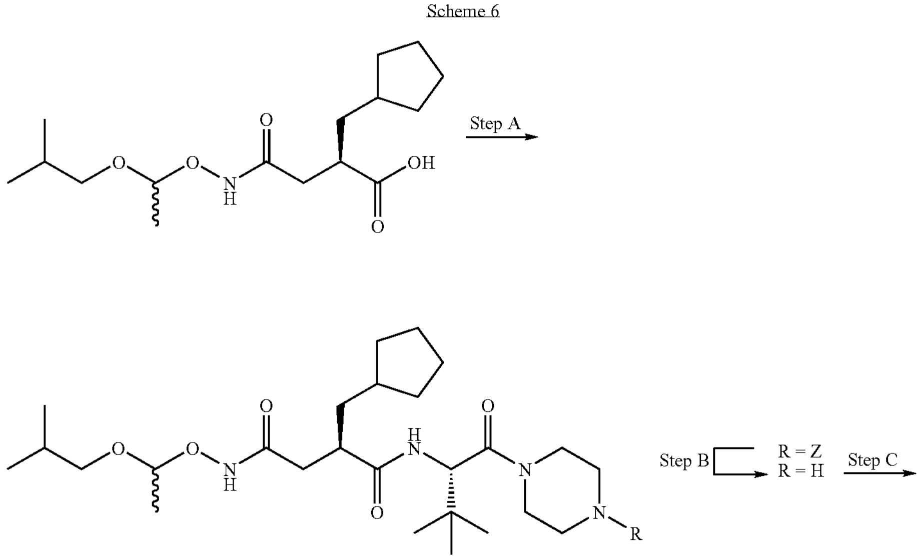

-continued

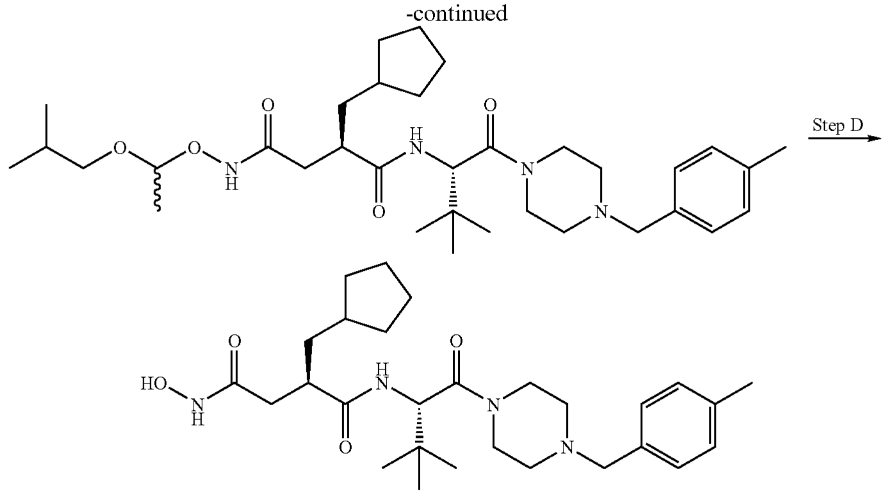

Step A: 4-(2S-[2R-Cyclopentylmethyl-3-(1-isobutoxy-ethoxycarbamoyl)-propionylamino]-3,3-dimethyl-butyryl}-piperazine-1-carboxylic acid benzyl ester To a cold (0° C.) solution of the acid (6.8 g, 16.1 mmol) in dichloromethane (80 ml), the hydrochloride salt of the amine (8.65 g, 19.4 mmol) was added followed by triethylamine (2.92 ml, 21 mmol) and then WSC (3.72 g, 19.4 mmol). The reaction mixture was stirred overnight allowing the temperature to come back to room temperature. The reaction mixture was then diluted with dichloromethane and washed with water (80 ml), with $Na_2CO_3$ and brine. The combined organic layer was dried over $MgSO_4$ and the solvent was removed in vacuo to yield a yellowish foam which was purified through flash chromatography to give a 100% pure compound (8 g, 79% yield).

$^1$H-NMR, δ ($CDCl_3$), 8.20 (1H,m), 7.32 (5H, m), 6.45 (1H, m), 5.11 (2H, s), 4.91–4.82 (2H, m), 3.87–3.21 (12H, m), 2.41 (1H, m), 2.73 (1H, m), 1.90–1.40 (14H, m), 1.36 (3H, m), 0.98 (9H, s), 0.90 (6H, d)

Step B: 2R-Cyclopentylmethyl-$N^1$-[2,2-dimethyl-1S-(piperazine-1-carbonyl)-propyl]-$N^4$-(1-isobutoxyethoxy)-succinamide To a suspension of the Z-protected piperazine (8 g, 12.7 mmol) in MeOH (100 ml) was added Pd/C (0.8 g) and then $H_2$ was bubbled for 1 h. The reaction mixture was then stirred under a blanket of $H_2$ for another hour. Pd/C was filtered off through a celite pad to give the desired compound in a 99% yield.

ESMS; +ve ion 498 [M+1], −ve ion 496 [M−1]; HPLC: RT=5.21 min

Step C: 2R-Cyclopentylmethyl-$N^1$-{2,2-dimethyl-1S-[4-(4-methyl-benzyl)-piperazine-1-carbonyl]-propyl}-$N^4$-(1-isobutoxyethoxy)-succinamide To a solution of 4-methyl benzyl bromide (74 mg, 0.4 mmol) in dichloromethane (2 ml) were added a solution of the piperazine in dichloromethane (1.2 ml, 0.33 mmol) and $Net_3$ (60 ml, 0.4 mmol). The reaction mixture was stirred at room temperature for 12 hours. Water was added (1.5 ml) and the resulting solution filtered through polypropylene hydrophobic cartridges (1PS filter). The solvent was then removed under reduced pressure to afford the expected adduct.

Step D: 2R-Cyclopentylmethyl-$N^1$-{2,2-dimethyl-1S-[4-(4-methyl-benzyl)-piperazine-1-carbonyl]-propyl}-$N^4$-hydroxy-succinamide To a solution of the latter in MeOH (4 ml) was added HCl 1N (600 ml) and the reaction mixture was stirred for 2 h. Then 60 ml of $NEt_3$ were added and the solvent was removed under reduced pressure. The crude reaction mixture was purified through HPLC.

The compounds of Examples 85–87 were prepared by the synthetic route outlined in Scheme 5 and as described in detail for Preparative Example A. Step C and Step D were carried out in parallel format for all examples. Characterisation data for the compounds are provided in Table 6.

TABLE 6

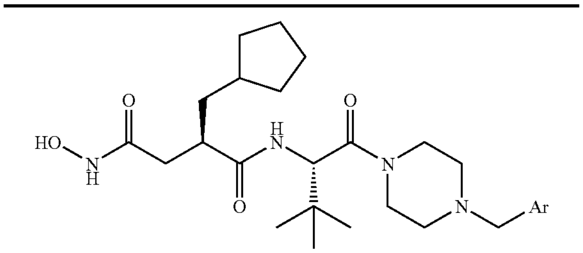

| Example | Structures | Mass Spec | Retention Time (min) |
|---|---|---|---|
| 85 | 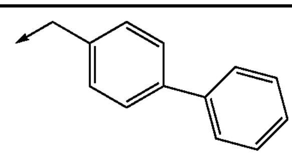 | M + 1 = 563<br>M − 1 = 561 | 5.2 |
| 86 | 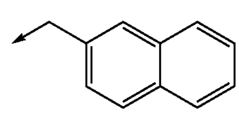 | M + 1 = 537<br>M − 1 = 535 | 5.03 |
| 87 | 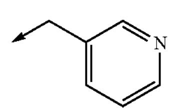 | M + 1 = 488<br>M − 1 = 486 | 4.17 |

The compounds of Examples 85–87 are named as follows:

EXAMPLE 85

$N^1$-[1S-(4-Biphenyl-4-ylmethyl-piperazine-1-carbonyl)-2,2-dimethyl-propyl]-2R-cyclopentylmethyl-$N^4$-hydroxy-succinamide

EXAMPLE 86

2R-Cyclopentylmethyl-$N^1$-[2,2-dimethyl-1S-(4-naphthalen-2-ylmethyl-piperazine-1-carbonyl)-propyl]-$N^4$-hydroxy-succinamide

EXAMPLE 87

2R-Cyclopentylmethyl-$N^1$-[2,2-dimethyl-1S-(4-pyridin-3-ylmethyl-piperazine-1-carbonyl)-propyl]-$N^4$-hydroxy-succinamide

EXAMPLE 88

4-(1-{2S-[3-(Benzyloxy-formyl-amino)-2R-cyclopentylmethyl-propionylamino]-3,3-dimethyl-butyryl)}-piperidin-4-yloxy)-N,N-dimethyl benzamide

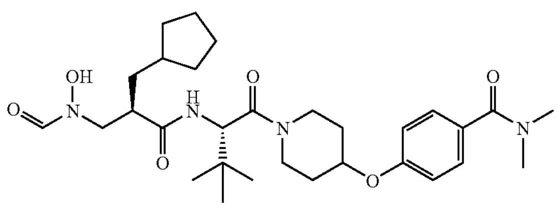

The title compound was prepared as detailed below (see scheme 8) from the the 3-(Benzyloxy-formyl-amino)-2R-cyclopentylmethyl-propionic acid pentafluorophenyl ester and 4-[1-(2S-Benzyloxycarbonylamino-3,3-dimethyl-butyryl)-piperidin-4-yloxy]-benzoic acid methyl ester (see scheme 7).

Scheme 7

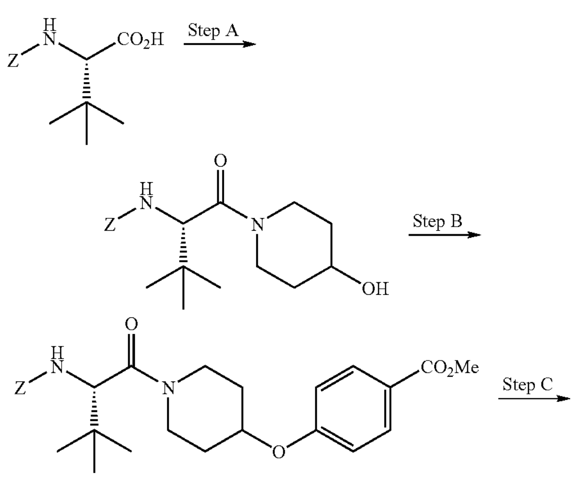

-continued

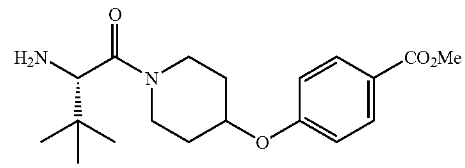

Step A: [1S-(4-Hydroxy-piperidine-1-carbonyl)-2,2-dimethyl-propyl]-carbamic acid benzyl ester To a cold solution (0° C.) of the Z-tert-leucine (3.48 g, 13.1 mmol) and 4-hydroxy piperidine (1.4 g, 13.7 mmol) in $CH_2Cl_2$ (40 ml) were added WSC (2.75 g, 14.4 g) followed by HOAt (18 mg, 0.13 mmol). The reaction mixture was stirred at room temperature for 12 hours and then washed with water and brine. The combined organic layer was dried over $MgSO_4$ and the solvent removed under reduced pressure to furnish a yellow oil which was purified through flash chromatography. The desired compound was obtained in 64% yield.

$^1$H NMR; δ ($CDCl_3$), 7.34 (5H, s), 5.58 (1H, m), 5.08 (2H, m), 4.60 (1H, m), 3.91 (3H, m), 3.49–3.05 (2H, m), 1.91 (4H, m). 0.98 (9H, d, J=3.57); ESMS; +ve ion 371 [M+Na]; HPLC: RT=5.44 min.

Step B: 4-[1-(2S-Benzyloxycarbonylamino-3,3-dimethyl-butyryl)-piperidin4-yloxy]-benzoic acid methyl ester To a cold solution (0° C.) of the latter compound (1.45 g, 4.2 mmol), 4-hydroxy methyl benzoate (0.7 g, 4.6 mmol) and triphenylphosphine (1.48 g, 5.46 mmol) were added dropwise followed by the addition of DEAD (0.86 ml, 5.46 mmol). The reaction mixture was stirred at 0° C. for 2.5 hours. Thf was removed in vacuo and the crude residue was taken-up in ethyl acetate. The organic layer was washed with water and brine and subsequently dried over $MgSO_4$. After purification through flash chromatography the expected compound was obtained as a pure white foam in 70% yield.

$^1$H NMR; δ ($CDCl_3$), 7.99 (2H, dd, $J_1$=1.23 $J_2$=8.82 ), 7.35 (5H, m), 6.92 (2H, dd, $J_1$=1.18 $J_2$=8.76), 5.58 (1H, m), 5.09 (2H, m), 4.62 (2H, m), 3.89 (4H, m), 3.72 (1H, m), 3.61 (2H, m), 1.90 (4H, m), 0.99 (9H, s); ESMS; +ve ion 505 [M+Na]; HPLC: RT=6.73 min.

Step C: 4-[1S-(2-Amino-3,3-dimethyl-butyryl)-piperidin4-yloxy]-benzoic acid methyl ester To a solution of the latter compound (650 mg, 1.35 mmol) in EtOH (10 ml) was added Pd/C (65 mg) and $H_2$ was bubbled through the resulting suspension for 4 hours. Pd/C was then removed by filtration through a celite pad. The solvent was removed under reduced pressure to give the desired compound in quantitative yield.

$^1$H NMR; δ ($CDCl_3$), 7.99 (2H, d, J=8.82), 6.92 (2H, d, J=8.47), 4.65 (1H, m), 3.89 (3H, s), 3.72 (2H, m), 3.56 (1H, d, J=4.82), 1.95 (4H, m), 0.99 (9H, s); ESMS; +ve ion 349 [M+1].

Scheme 8

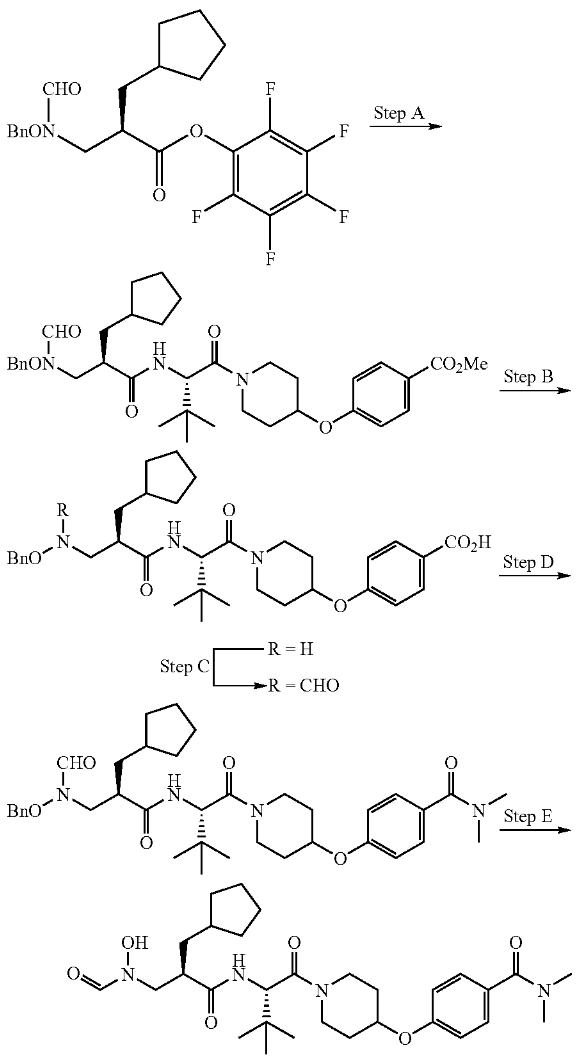

Step A: 4-(1-{2S-[3-(Benzyloxy-formyl-amino)-2R-cyclopentylmethyl-propionylamino]-3,3-dimethyl-butyryl}-piperidin-4-yloxy)-benzoic acid methyl ester To a solution of the amine (3.4 g, 9.70 mmol) in DMF were added the PFP ester (4 g, 8.50 mmol) followed by $NEt_3$ (1.3 ml, 9.34 mmol). The reaction mixture was stirred overnight at room temperature. The solvent was removed under reduced pressure and the crude dissolved in ethyl acetate. The work-up was made by means of water, sodium carbonate, ammonium chloride and brine. The combined organic layer was dried over $MgSO_4$ and the solvent removed under reduced pressure to yield a foam. The crude product was purified through flash chromatography to yield the desired compound as a white foam in 98% yield.

$^1$H-NMR; δ ($CDCl_3$ rotamers), 8.01–7.96 (2H, m), 7.38 (5H, bs), 6.93–6.88 (2H, m), 6.32–6.29 (1H, m), 5.01–4.52 (7H, m), 4.02–3.52 (7H, m), 3.89 (3H, s), 2.68–2.50 (1H, m), 1.98–1.34 (15H, m), 0.95 (9H, s); LRMS: +ve ion 436 [M+H], 658 [M+Na]. HPLC: RT=6.79 min, 98% pure.

Step B: 4-{1-[2S-(3-Benzyloxyamino-2R-cyclopentylmethyl-propionylamino)-3,3-dimethyl-butyryl]-piperidin-4-yloxy}-benzoic acid To a cold solution (0° C.) of the latter compound (100 mg, 0.16 mmol) in a mixture of THF/MeOH/$H_2O$ (3:1:1; 2.5 ml) was added LiOH (33 mg). The reaction mixture was stirred for 48 hours at room temperature. The solvent was removed under vacuo and the crude dissolved in water. The aqueous layer was extracted by means of $Et_2O$ and then acidified to pH=1 by means of HCl 1 N. The desired product was then extracted from $Et_2O$. The organic layer was dried over $MgSO_4$ and the solvent removed under reduced pressure to yield the desired compound as a white solid in 61% yield.

$^1$H-NMR; δ ($CDCl_3$ rotamers), 8.06–8.01 (2H, m), 7.38–7.30 (5H, m), 7.09–6.99 (1H, 2d, J=9.3 Hz), 6.94–6.89 (2H, m), 5.02 (1H, d, J=9.4 Hz), 4.75 (2H, s), 4.69–4.61 (1H, m), 4.08–3.67 (4H, m), 3.58–3.42 (2H, m), 3.17–3.01 (2H, m), 2.62 (1H, m), 2.10–1.40 (15H, m), 1.01 (9H, s); LRMS: +ve ion 594 [M+H], −ve ion 592 [M−1]. HPLC: RT=5.92 min, 98% pure.

Step C: 4-(1-{2S-[3-(Benzyloxy-formyl-amino)-2R-cyclopentylmethyl-propionylamino]-3,3-dimethyl-butyryl}-piperidin-4-yloxy)-benzoic acid To a cold (0° C.) of the acid (4.8 g, 8.1 mmol) in THF (100 ml) were added the mixed anhydride (1.8 g, 20.3 mmol) and $NEt_3$ (3.33 ml, 24.3 mmol). The reaction mixture was stirred at room temperature for 12 hours. The solvent was then removed under reduced pressure and the residue was dissolved in $CH_2Cl_2$. The organic layer was washed with wate and brine and dried over $MgSO_4$. The solvent was removed in vacuo to yield the desired derivative.

$^1$H-NMR; δ ($CDCl_3$, rotamers), 8.19–7.89 (3H, bs), 7.46–7.30 (5H, m), 7.02–6.85 (1H, m), 5.02–4.53 (4H, m), 4.04–3.37 (6H, m), 2.70 (1H, m), 1.98–1.35 (15H, m), 0.97 (9H, s); LRMS: +ve ion 644 [M+Na], −ve ion 620 [M−1] HPLC: RT=6.29 min, 95% pure.

Step D: 4-(1-{2S-[3-(Benzyloxy-formyl-amino)-2R-cyclopentylmethyl-propionylamino]-3,3dimethyl-butyryl}-piperidin-4-yloxy)-N,N-dimethyl-benzamide To a cold (0° C.)solution of the starting acid (0.35 g, 0.56 mmol) in $CH_2Cl_2$ (8 ml) were added dimethyl amine (0.67 mmol), WSC (118 mg, 0.61 mmol) and HOAt (8 mg, 0.06 mmol). The reaction mixture was stirred at room temperature for 12 hours. Water was added (3 ml) and the resulting solution filtered through polypropylene hydrophobic cartridges (1PS filter). The solvent was then removed under reduced pressure to afford the expected adduct. The crude compound was then purified through flash chromatography to afford a 100% pure compound with a 55% yield.

LRMS: +ve ion 671 [M+Na], HPLC: RT=6.32 min, 100% pure.

Step E: 4-(1S-{2-[2R-Cyclopentylmethyl-3-(formyl-hydroxy-amino)-propionylamino]-3,3-dimethyl-butyryl)}-piperidin-4-yloxy)-N,N-dimethyl-benzamide To a solution of the latter compound (200 mg, 0.31 mmol) were added cyclohexene (0.5 ml) and Pd/C (24 mg). The reaction mixture was stirred to reflux for 3 h. Pd/C was then filtered off through a celite pad. The solvent was removed under reduced pressure to afford the desired adduct as a pure compound. LRMS: +ve ion 581 [M+Na], HPLC: RT=5.49 min, 100% pure.

The compounds of Examples 88a-93 were prepared by the synthetic route outlined in Scheme 9 and as described in detail for Example 88. Step C and Step D were carried out in parallel format for all examples. Characterisation data for the compounds are provided in Table 7.

TABLE 7
| Example | Structure | Mass Spectral Data | HPLC RT (min) |
|---|---|---|---|
| 88 | 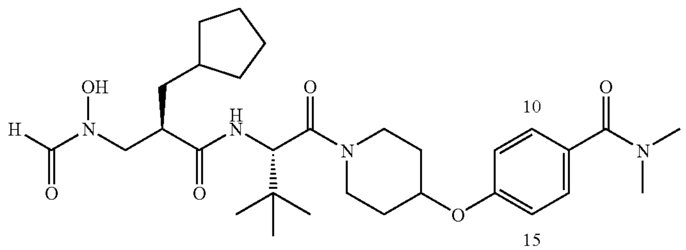 | 581 (M + Na), 559 (M + 1), 557 (M − 1). | 5.5 |
| 88a | 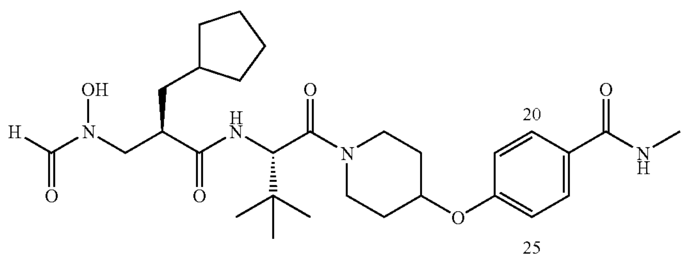 | 545 (M + 1), 567 (M + Na), 543 (M − 1). | 5.3 |
| 89 | 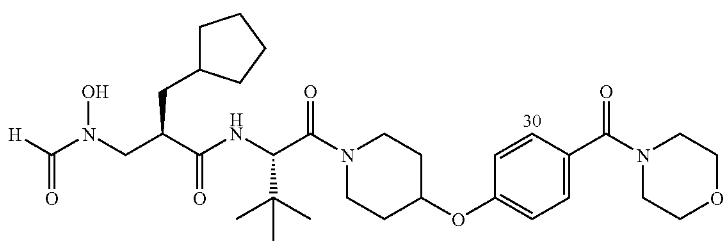 | 601 (M + 1), 623 (M + Na), 599 (M − 1). | 5.4 |
| 90 | 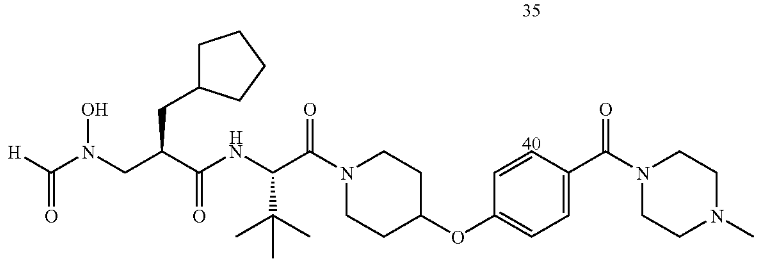 | 614 (M + 1), 636 (M + Na), 612 (M − 1). | 4.8 |
| 91 | 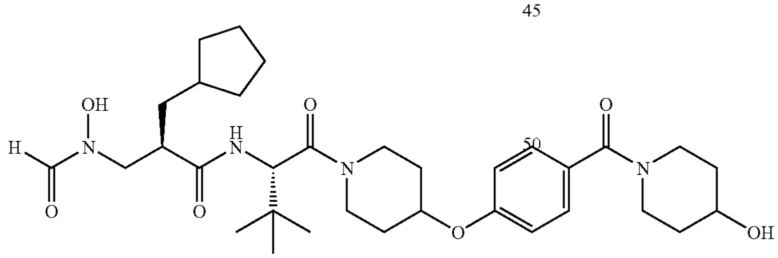 | 615 (M + 1), 637 (M + Na), 613 (M − 1). | 5.2 |
| 92 | 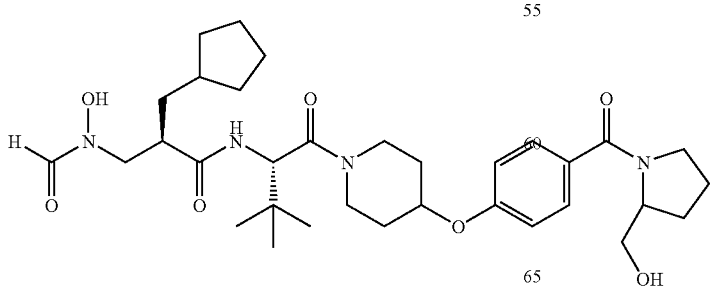 | 615 (M + 1), 637 (M + Na), 613 (M − 1). | 5.4 |

The compounds of Examples 88a -93 are named as follows:

EXAMPLE 88a 4-(1-{2S-[3-(Benzyloxy-formyl-amino)-2R-cyclopentylmethyl-propionylamino]-3,3-dimethyl-butyryl}-piperidin-4-yloxy)N-methyl benzamide

EXAMPLE 89

2R-Cyclopentylmethyl-N-(2,2-dimethyl-1S-{4-[4-(morpholine-4-carbonyl)-phenoxy]-piperidine-1-carbonyl}-propyl)-3-(formyl-hydroxy-amino)-propionamide.

EXAMPLE 90

2R-Cyclopentylmethyl-N-(2,2-dimethyl-1S-{4-[4-(4-methyl-piperazine-1-carbonyl)-phenoxy]-piperidine-1-carbonyl}-propyl)-3-(formyl-hydroxy-amino)-propionamide.

EXAMPLE 91

2R-Cyclopentylmethyl-3-(formyl-hydroxy-amino)-N-(1S-{4-[4-(4-hydroxy-piperidine-1-carbonyl)-phenoxy]-piperidine-1-carbonyl}-2,2-dimethyl-propyl)-propionamide.

EXAMPLE 92

2R-Cyclopentylmethyl-3-(formyl-hydroxy-amino)-N-(1S-{4-[4-(2S-hydroxymethyl-pyrrolidine-1-carbonyl)-phenoxy]-piperidine-1-carbonyl}-2,2-dimethyl-propyl)-propionamide.

EXAMPLE 93

4-(1-{2S-[2R-Cyclopentylmethyl-3-(formyl-hydroxy-amino)-propionylamino]-3,3-dimethyl-butyryl)piperidin-4-yloxy)benzoic acid

EXAMPLE 94

4-(1-(2S-[2R-Cyclopentylmethyl-3-(formyl-hydroxy-amino)-propionylamino]-3,3-dimethyl-butyryl}-piperidin-4-yloxy)-benzoic acid methyl ester

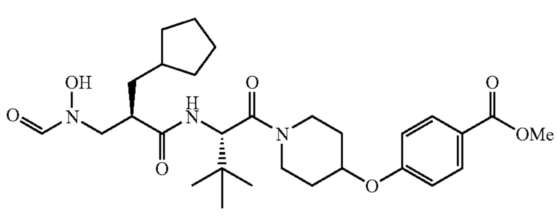

The title compound was prepared as detailed below (see scheme 9) from 4-(1-{2S-[3-(Benzyloxy-formyl-amino)-2R-cyclopentylmethyl-propionylamino]-3,3-dimethyl-butyryl}-piperidin-4-yloxy)-benzoic acid methyl ester (scheme 8).

Scheme 9

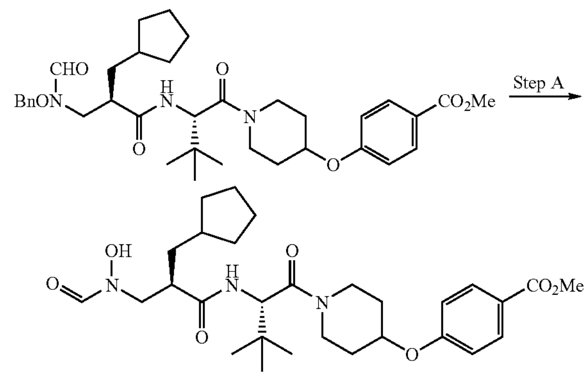

To a solution of 4-(1-{2S-[3-(Benzyloxy-formyl-amino)-2R-cyclopentylmethyl-propionylamino]-3,3-dimethyl-butyryl}-piperidin-4-yloxy)benzoic acid methyl ester (80 mg, 0.125 mmol) in EtOH (4 ml) was added Pd/C (10 mg). To the resulting suspension, $H_2$ was bubbled for 2 h. Pd/C was filtered off through a celite pad to give the desired compound in 88% yield.

$^1$H NMR δ ($CDCl_3$), 8.40 (0.3H, s), 7.99 (2H, dd, $J_1$=3.04 $J_2$=8.85), 7.81 (0.7H, s), 6.91 (2H, dd, $J_1$=4.87 $J_2$=8.84), 6.78 (1H, m), 4.94 (1H, m), 4.64 (1H, m), 3.99 (2H, m), 3.89 (3H, s), 3.75 (2H, m), 3.48 (3H, m), 2.81 (1H, m), 2.10–1.32 (13H, m), 1.08 (2H, bs), 0.97 (9H, m); $^{13}$C NMR δ ($CDCl_3$), 175.7. 173.6, 170.3, 167.1, 161.2, 132.1, 123.4, 115.5, 72.3, 58.7, 55.1, 54.8, 52.9, 52.3, 44.2, 43.6, 39.2, 39.1, 38.4, 36.6, 35.8, 33.2, 31.6, 31.2, 27.0, 25.5.

EXAMPLE 95

2R-Cyclopentylmethyl-3-(formyl-hydroxy-amino)-N-{1S-[4-(4-hydroxymethyl-phenoxy)-piperidine-1-carbonyl]-2,2-dimethyl-propyl}-propionamide

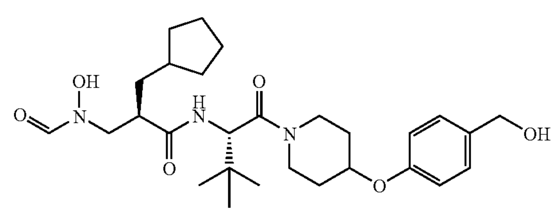

The title compound was prepared as detailed below (see scheme 10) from 4-[1-(2S-Benzyloxycarbonylamino-3,3dimethyl-butyryl)-piperidin4-yloxy]-benzoic acid Scheme 10

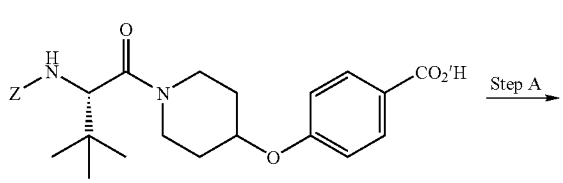

-continued

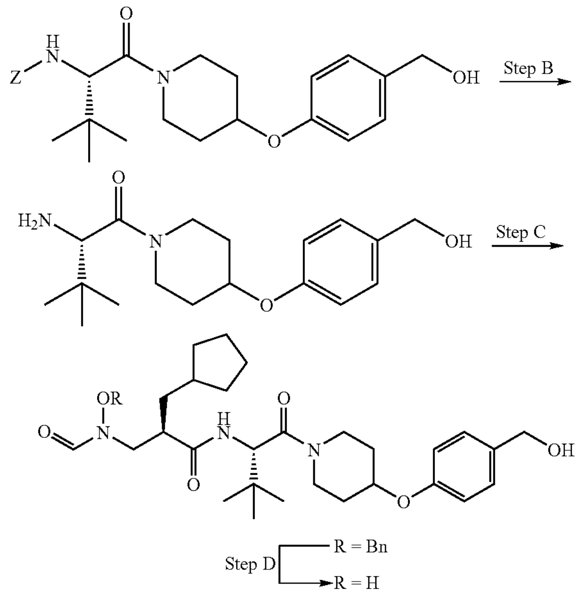

Step A: {1S-[4-(4-Hydroxymethyl-phenoxy)-piperidine-1-carbonyl]-2,2-dimethyl-propyl}-carbamic acid benzyl ester To a cold (10° C.) solution of the 4-[1-(2S-Benzyloxy-carbonylamino-3,3-dimethyl-butyryl)-piperidin-4-yloxy]-benzoic acid (750 mg, 1.6 mmol) in THF (10 ml) was added dropwise $BH_3$ The reaction mixture was stirred at room temperature for 12 hours. Water was then added dropwise and the solvent removed under reduced pressure. The crude material was taken-up in EtOAc. After filtration, the organic layer was concentrated to yield a white foam as a pure compound in 93% yield.

$^1$H NMR δ ($CDCl_3$), 7.35–7.28 (7H, m), 6.89 (2H, m), 5.60 (1H, m), 5.15–5.03 (2H, AB system), 4.65–4.48 (3H, m), 3.91–3.51 (5H, m), 1.95–1.25 (4H, m), 1.00 (9H, s). ESMS: +ve ion 477 [M+Na], HPLC: RT=6.3 min, 93% pure.

Step B: 2S-Amino-1-[4-(4-hydroxymethyl-phenoxy)-piperidin-1-yl]-3,3-dimethyl-butan-1-one To a solution of the latter compound (680 mg, 1.49 mmol) in EtOH (10 ml) was added Pd/C (68 mg) and $H_2$ was bubbled through the resulting suspension for 2 hours. The reaction mixture was then stirred for two hours under a blanket of $H_2$. Pd/C was then filtered off through a celite pad. The solvent was removed under reduced pressure to give the desired compound in 94% yield. $^1$H NMR δ ($CDCl_3$), 7.29–6.86 (4H, AB system), 4.62 (2H, s), 4.55 (1H, m), 3.82–3.58 (2H, m), 1.92–1.73 (11H), 1.00 (9H, s). ESMS: +ve ion 321 [M+1].

Step C: 3-(Benzyloxy-formyl-amino)-2R-cyclopentylmethyl-N-{1S-[4-(4-hydroxymethyl-phenoxy)-piperidine-1-carbonyl]-2,2-dimethyl-propyl}-propionamide To a solution of the latter compound, were added PFP ester (635 mg, 1.35 mmol) and $NEt_3$ (193 ml, 1.41 mmol). The reaction mixture was then stirred for 12 hours. DMF was removed under reduced pressure and the crude material was taken-up in EtOAc, washed with water, sodium carbonate (1N), saturate aqueous solution of $NH_4Cl$ and brine. The combined organic layer was dried over $MgSO_4$ and the solvent was removed under reduced pressure. After purification through flash chromatography the desired adduct was obtained as a white foam in 63% yield. $^1$H NMR; δ ($CDCl_3$), 8.13 (0.25H, m), 7.88 (0.25H, m), 7.38 (5H, s), 7.27 (2.5H, m), 6.87 (2H, m), 6.32 (1H, m), 4.89 (3H, m), 4.56 (3H, m), 3.96 (1H, m), 3.73 (2H, m), 3.45 (1H, m), 2.60 (1H, m), 2.06–1.31 (15H, m), 1.06 (11H, m); ESMS: +ve ion 630 [M+Na], HPLC: RT=6.31 min, 100% pure.

Step D: 2R-Cyclopentylmethyl-3-(formyl-hydroxy-amino)-N-{1S-[4(4-hydroxymethyl-phenoxy)piperidine-1-carbonyl]-2,2-dimethyl-propyl}-propionamide To a solution of the latter compound (50 mg, 0.08 mmol) in MeOH (3 ml) were added $HCO_2NH_4$ (26 mg, 0.41 mmol) and Pd/C (5 mg). The resulting suspension was stirred for 2 hours. Pd/C was filtered off. The solvent was removed under reduced pressure and the crude material taken-up in EtOAc, washed with water and brine. The combined organic layer was dried over $MgSO_4$ and the solvent was removed under reduced pressure to yield the expected compound in 62% yield. $^1$H NMR; δ ($CDCl_3$), 8.39 (0.3H, s), 7.81 (0.7H, s), 7.29 (2H, dd, $J_1$=3.47 $J_2$=9.11), 6.89 (2H, dd, $J_1$=3.64 $J_2$=8.55), 6.73 (1H, m), 4.94 (1H, m), 4.62 (3H, m), 4.01 (2H,m), 3.76 (2H, m), 3.48 (3H, m), 2.74 (1H, m), 2.08–1.35 (19H, m), 1.02 (13H, m); ESMS: +ve ion 540 [M+Na], −ve ion 516 [M−1] HPLC: RT=5.49 min, 100% pure.

BIOLOGICAL EXAMPLE

Minimal inhibitory concentrations (MIC) of compounds of the invention against *E. coli* strain DH5α (Genotype; F-φ80dlacZΔM15Δ(lacZYA-argF)U169 deoR recA1 endA1 hsdR17($r_k^-$, $m_k^+$)phoA supE44λ$^-$ thi-1 gyrA96 relA1) obtained from GibcoBRL Life Technologies, or *Staphylococcus capitis* (American Type Culture Collection number 35661) were determined as follows. Stock solutions of each test compound were prepared by dissolution of the compound in dimethylsulfoxide at 10 mM. For the determination of the minimal inhibitory concentration, two fold serial dilutions were prepared in 2xYT broth (typtone 16 g/1, yeast extract 10 g/l, sodium chloride 5 g/1 obtained from BIO 101 Inc. 1070 Joshua Way, Vista, Calif.92083, USA) to yield 0.05 ml compound-containing medium per well. Inocula were prepared from cultures grown overnight in 2xYT broth at 37° C. Cell densities were adjusted to absorbance at 660 nm ($A_{660}$)=0.1; the optical density-standardised preparations were diluted 1:1000 in 2xYT broth; and each well inoculated with 0.05 ml of the diluted bacteria. Microtiter plates were incubated at 37° C. for 18 hours in a humidified incubator. The MIC (μM) was recorded as the lowest drug concentration that inhibited visible growth.

In general, the compounds of the Examples were more active against the Gram positive *S. capitis* than the Gram negative *E. coli*. Results for some of the compounds of the Examples are reported in Table 8:

TABLE 8

| Example No. | *E. Coli* MIC (μM) | *S. Capitis* (μM) |
|---|---|---|
| 24 | >200, <400 | 100 |
| 29 | 100 | >200, <400 |
| 44 | 200 | 12 |
| 50 | 200 | 6.2 |
| 52 | 200 | 6.2 |
| 54 | 200 | 3.1 |
| 55 | 200 | 6.2 |
| 56 | 50 | 25 |
| 57 | 100 | 6.2 |

TABLE 8-continued

| Example No. | *E. Coli* MIC (μM) | *S. Capitis* (μM) |
|---|---|---|
| 69 | 200 | 25 |
| 74 | 200 | 25 |
| 78 | >200, <400 | 200 |
| 79 | >200, <400 | 6.25 |
| 88 | 100 | 6.2 |
| 89 | 200 | 25 |
| 91 | 200 | 25 |

Using the above protocol for establishing the MIC values against *S. capitis*, it appears that in general compounds of the invention of formula (II) wherein Q is a hydroxamate group have activities comparable to compounds of similar structure wherein Q is an N-formylhydroxylamine group.

In another experiment, the MICs of the compound of Example 91 were determined against certain respiratory tract pathogens, using the Microdilution Broth Method according to the approved standard of the National Committee for Clinical Laboratory Standards procedure (Methods for dilution antimicrobial susceptibility tests for bacteria that grow aerobically—Fourth Edition ISBN 1-56238-3094). The results appear in Table 9.

TABLE 9

| Organism | MIC (μg/ml) |
|---|---|
| *Moraxella catarrhalis* 2413 | 0.25 |
| *Moraxella catarrhalis* 2412 | 0.5 |
| *Haemophilus Infuenzae* 1414 | 4 |
| *Haemophilus Infuenzae* 1390 | 1 |
| *Streptococcus pneumoniae* (PRP) 2390 | 0.25 |
| *Streptococcus pneumoniae* (PIP) 2391 | 0.25 |
| *Streptococcus pneumoniae* (PSP) 2403 | 0.25 |

The invention claimed is:

1. A compound of formula (II), or a pharmaceutically or veterinarily acceptable salt, hydrate or solvate thereof

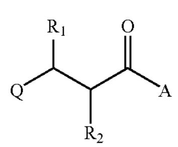

(II)

wherein

Q represents a radical of formula —N(OH)CH(═O) or formula —C(O)NH(OH);

when Q is —N(OH)CH(═O), $R_1$ represents hydrogen, $C_1$–$C_6$ alkyl, or $C_1$–$C_6$ alkyl substituted by one or more halogen atoms;

when Q is —C(═O)NH(OH), $R_1$ represents hydrogen, $C_1$–$C_6$ alkyl, $C_1$–$C_6$ alkyl substituted by one or more halogen atoms, a hydroxy, $C_1$–$C_6$ alkoxy, $C_2$–$C_6$ alkenyloxy, amino, $C_1$–$C_6$ alkylamino, or di-($C_1$–$C_6$ alkyl) amino group;

$R_2$ represents a substituted or unsubstituted $C_1$–$C_6$ alkyl, cycloalkyl ($C_1$–$C_6$ alkyl)- or aryl($C_1$–$C_6$ alkyl)-group;

and A represents a group of formula (hA), or (IIB):

(IIA)

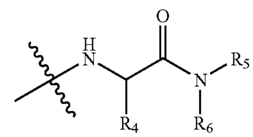

(IIB)

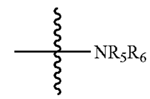

wherein $R_4$ represents the characterizing group of a natural a amino acid or 4-methoxyphenylmethyl, in which any functional group may be protected, any amino group may be acylated and any carboxyl group present may be amidated; or a group -$(Alk)_nR_6$ where Alk is a $(C_1$–$C_6)$alkylene or $(C_2$–$C_6)$alkenylene group optionally interrupted by one or more —O—, or —S-atoms or —$N(R_{12})$-groups where $R_{12}$ is a hydrogen atom or a $(C_1$–$C_6)$alkyl group, n is 0 or 1, and $R_9$ is hydrogen or an optionally substituted phenyl, aryl, heterocyclyl, cycloalkyl or cycloalkenyl group or (only when n is 1) $R_9$ may additionally be hydroxy, mercapto, $(C_1$–$C_6)$ alkylthio, amino, halo, trifluoromethyl, nitro, —COGH, —$CONH_2$, —$COOR^A$, —$NHCOR^A$, —$CONHR^A$, —$NHR^A$, —$NR^AR^B$, or —$CONR^AR^B$ wherein R and RB are independently a$(C_1$–$C_6)$ alkyl group; or a benzyl group substituted in the phenyl ring by a group of formula $OCH_2COR_8$ where $R_8$ is hydroxyl, amino, $(C_1$–$C_6)$alkoxy, phenyl$(C_1$–$C_6)$alkoxy, $(C_1$–$C_6)$alkylamino, di($(C_1$–$C_6)$alkyl)amino, phenyl $(C_1$–$C_6)$ alkylamino; or a heterocyclic$(C_1$–$C_6)$alkyl group, either being unsubstituted or mono- or di-substituted in the heterocyclic ring with halo, nitro, carboxy, $(C_1$–$C_6)$alkoxy, cyano, $(C_1$–$C_6)$alkanoyl, trifluoromethyl $(C_1$–$C_6)$alkyl, hydroxy, formyl, amino, $(C_1$–$C_6)$alkylamino, di-$(C_1$–$C_6)$alkylamino, mercapto, $(C_1$–$C_6)$alkylthio, hydroxy$(C_1$–$C_6)$alkyl, mercapto$(C_1$–$C_6)$alkyl or $(C_1$–$C_6)$alkylphenylmethyl; or a group —$CR_aR_bR_c$ in which:

each of $R_a$, $R_b$ and $R_c$ is independently hydrogen, $(C_1$–$C_6)$alkyl, $(C_2$–$C_6)$alkenyl, $(C_2$–$C_6)$ alkynyl, phenyl$(C_1$–$C_6)$alkyl, $(C_3$–$C_8)$cycloalkyl; or $R_c$ is hydrogen and $R_a$ and $R_b$ are independently phenyl or heteroaryl; or $R_c$ is hydrogen, $(C_1$–$C_6)$alkyl, $(C_2$–$C_6)$alkenyl, $(C_2$–$C_6)$ alkynyl, phenyl $(C_1$–$C_6)$ alkyl, or $(C_3$–$C_8)$cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring; or $R_a$ and $R_b$ are each independently $(C_1$–$C_6)$alkyl, $(C_2$–$C_6)$alkenyl, $(C_2$–$C_6)$alkynyl, phenyl$(C_1$–$C_6)$ alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —$CO_2H$, $(C_1$–$C_4)$perfluoroalkyl, —$CH_2OH$, —CO $_2(C_1$–$C_6)$alkyl, —$O(C_1$–$C_6)$alkyl, —O($C_2$–$C_6$)alkenyl, —S($C_1$–$C_6$)alkyl, —SO($C_1$–$C_6$)alkyl, —$SO_2$($C_1$–$C_6$)alkyl, —S($C_2$–$C_6$)alkenyl, —SO($C_2$–$C_6$) alkenyl, —$SO_2$($C_2$–$C_6$) alkenyl or a group -Q-W wherein Q represents a bond or —O—, —S—, —SO— or —$SO_2$— and W represents a phenyl, phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —$CO_2$H, —$CO_2$($C_1$–$C_6$)alkyl, —$CONH_2$, —CONH($C_1$–$C_6$)alkyl, —CONH($C_1$–$C_6$alkyl)$_2$, —CHO, —$CH_2$OH, ($C_1$–$C_4$perfiuoroalkyl, —O($C_1$–$C_6$)alkyl, —S($C_1$–$C_6$) alkyl, —SO($C_1$–$C_6$)alkyl, —$SO_2$($C_1$–$C_6$)alkyl, —$NO_2$, —$NH_2$, —NH($C_1$–$C_6$)alkyl, —N(($C_1$–$C_6$)alkyl)$_2$, —NHCO($C_1$–$C_6$)alkyl, ($C_1$–$C_6$)alkyl, ($C_2$–$C_6$)alkenyl, ($C_2$–$C_6$)alkynyl, ($C_3$–$C_8$)cycloalkyl, ($C_4$–$C_8$)cycloalkenyl, phenyl or benzyl; and $R_5$ and $R_6$ are taken together with the nitrogen atom to which they are attached to form a piperidinyl ring; wherein the piperidinyl ring is substituted by a group of formula (IIC), provided that the piperidinyl ring is not substituted by phenoxy, benzyl or benzyl substituted by ($C_1$–$C_6$)alkyl, ($C_1$–$C_6$)alkoxy, phenoxy, hydroxy, mercapto, ($C_1$–$C_6$)alkylthio, amino, halo, trifluoromethyl, nitro, —COOH, —$CONH_2$, —$COR^A$, —$COOR^A$, —$NHCOR^A$, —$CONHR^A$, —$NHR^A$, —$NR^AR^B$, or —$CONR^AR^B$ wherein $R^A$ and $R^B$ are independently a ($C_1$–$C_6$)alkyl group, (IIC)

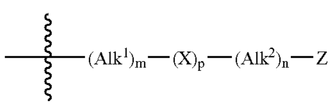

wherein m, p and n are independently 0 or 1;

Z represents, a hydroxy group, or a phenyl or heterocyclic ring of 5 to 7 atoms which is optionally fused to a saturated or unsaturated carbocyclic or heterocyclic second ring of 5 to 7 atoms $Alk^1$ and $Alk^2$ independently represent divalent $C_1$–$C_3$ alkylene radicals;

X represents —O—, —S—, —S(O)—, —S($O_2$)—, —C(=O)—, —NH—, —$NR_7$— where $R_7$ is $C_1$–$C_3$ alkyl;

and wherein $Alk^1$, $Alk^2$ and Z when Z is not a hydroxy group independently or optionally substituted by ($C_1$–$C_6$)alkyl, ($C_2$–$C_6$)alkenyl, or ($C_2$–$C_6$)alkynyl, phenyl, or halophenyl, trifluoromethyl, monocyclic 5 or 6-membered heterocyclic, benzyl, or halophenylmethyl, hydroxy, phenoxy, ($C_1$–$C_6$)alkoxy, or hydroxy($C_1$–$C_6$) alkyl, mercapto, ($C_1$–$C_6$)alkylthio or mercapto($C_1$–$C_6$)alkyl, oxo, nitro, cyano (—CN)

halo

—COOH, or —$COOR^A$,

—$CONH_2$, —$CONHR^A$, —$CONR^AR^B$

—$COR^A$, —$SO_2R^A$,

—$NHCOR^A$,

—$NH_2$, —$NHR^A$, or —-$NR^AR^B$, wherein $R^A$ and $R^B$ are independently a ($C_1$–$C_6$)alkyl group, $R^A$ and $R^B$ taken together with the nitrogen atom to which they are attached form a 5- or 6 membered heterocyclic ring which may be substituted by ($C_1$–$C_3$)alkyl, hydroxy, or hydroxyl($C_1$–$C_3$) alkyl.

2. A compound as claimed in claim 1 wherein the piperidinyl ring is substituted by a group of formula (IIC), provided that the piperidinyl ring is not substituted by phenoxy, benzyl or benzyl substituted by ($C_1$–$C_6$)alkyl, ($C_1$–$C_6$)alkoxy, phenoxy, hydroxy, mercapto, ($C_1$–$C_6$)alkylthio, amino, halo, trifluoromethyl, nitro, —COOH, —$CONH_2$, —$COR^A$, —$COOR^A$, —$NHCOR^A$, —$CONHR^A$, —$NHR^A$, —$NR^AR^B$, or —$CONR^AR^B$ wherein $R^A$ and $R^B$ are independently a ($C_1$–$C_6$)alkyl group, (IIC)

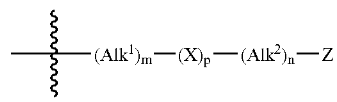

wherein m, p and n are independently 0 or 1;

Z represents, a hydroxy group, or a phenyl or heterocyclic ring of 5 to 7 atoms which is optionally fused to a saturated or unsaturated carbocyclic or heterocyclic second ring of 5 to 7 atoms $Alk^1$ and Alk2 independently represent divalent $C_1$–$C_3$ alkylene radicals;

X represents —O—, —S—, —1S(O)—, —S($O_2$)—, —C(=O)—, —NH—, —$NR_7$— where $R_7$ is $C_1$–$C_3$ alkyl;

and wherein $Alk_1$, $Alk_2$ and Z when Z is not a hydroxy group independently are optionally substituted by ($C_1$–$C_6$) alkyl, ($C_2$–$C_6$)alkenyl, or ($C_2$–$C_6$)alkynyl, phenyl, or halophenyl, trifluoromethyl, monocyclic 5 or 6-membered hetrocyclic, benzyl, hydroxy, phenoxy, or ($C_1$–$C_6$)alkoxy, mercapto, or ($C_1$–$C_6$)alkylthio, oxo, ntro, —COOH, or —$COOR^A$, —$CONH_2$—$CONHR^A$, or —$CONR^AR^B$

—$COR^A$,

—$NHCOR^A$,

—$NH_2$, —$NHR^A$, or —$NR^AR^B$, wherein $R^A$ and $R^B$ are independently a ($C_1$–$C_6$)alkyl group.

3. A compound as claimed in claim 1 wherein $R_1$ is hydrogen.

4. A compound as claimed in claim 3 wherein $R_2$ is ($C_1$–$C_6$)alkyl-, cycloalkylmethyl-, ($C_1$–$C_3$)alkyl-S—($C_1$–$C_3$)alkyl-, or ($C_1$–$C_3$)alkyl-O—($C_{C3}$)alkyl-.

5. A compound as claimed in claim 3 wherein $R_2$ is n-propyl, n-butyl, n-pentyl, cyclopentylmethyl, cyclopentylethyl, cyclohexylmethyl or cyclohexylethyl.

6. A compound as claimed in claim 5 wherein $R_4$ is methyl, ethyl, n-propyl, n-butyl, benzyl, 4-chlorobenzyl, 4-hydroxybenzyl, phenyl, cyclohexyl, cyclohexylmethyl, pyridin-3-ylmethyl, tertbutoxymethyl, naphthylmethyl, iso-butyl, sec-butyl, tert-butyl, 1-benzylthio-1-methylethyl, 1-methylthio-1-methylethyl, 1-mercapto-1-methylethyl, 1-methoxy-1-methylethyl, 1-hydroxy-1-methylethyl, 1-fluoro-1-methylethyl, hydroxymethyl, 2-hydroxetyl, 2-carboxyethyl, 2-methylcarbamoylethyl, 2-carbamoyl-ethyl,or 4-aminobutyl.

7. A compound as claimed in claim 5 wherein $R_4$ is tert-butyl, iso-butyl, benzyl, isopropyl or methyl.

8. A compound as claimed in claim 5, wherein the substituent (IIC) has the formula —$CH_2Z$, —OZ, or —(C═O)Z.

9. A compound as claimed in claim 5 wherein in the substituent (IIC), Z is a phenyl, 3,4-methylenedioxyphenyl, morpholinyl, pyrimidinyl, 1,2,3-thiadiazolyl, 1,4-thiazolyl, benzofuranyl, furanyl, thienyl, pyranyl, pyrrolyl, pyrazolyl, isoxazolyl, or pyridyl ring which may optionally be substituted.

10. A compound as claimed in claim 5 wherein in the substituent (IIC) Z is a phenyl, 3,4-methylenedioxyphenyl, morpholinyl, pyrimidin-2-yl, 1,2,3-thiadiazol-5-yl, 1,4-thiazol-5-yl,benzofuran-2-yl, 2 or 3-furanyl, 2- or 3-thienyl, 2- or 3-pyranyl, 2-, 3- or 4-pyrroiyl, 3-4-or 5-pyazolyl, 3-, 4-or 5-isoxazolyl, or 2-, 3-or 4-pyridyl ring which may optionally be substituted.

11. A compound as claimed in claim 1 wherein $R_1$ is hydrogen; $R_2$ is n-propyl, n-butyl, n-pentyl, cyclopentylm-ethyl, cyclopentylethyl, cyclohexylmethyl or cyclohexyl-ethyl; $R_4$ is tert-butyl, iso-butyl, benzyl or methyl; the substituent (IIC) has the formula —$CH_2Z$, —OZ, or —C═O)Z wherein Z is a phenyl, 3,4-methylenedioxyphe-nyl, morpholinyl, pyrimidin-2-yl, 1,2,3-thiadiazol-5-yl, 1,4-thiazol-5-yl,benzofuran-2-yl, 2 or 3-furanyl, 2- or 3-thienyl, 2- or 3-pyranyl, 2-, 3- or 4-pyrrolyl, 3-, 4- or 5-pyazo 3-, 4- or 5-isoxazolyl, or 2-, 3- or 4-pyridyl ring which may optionally be substituted.

12. A compound as claimed in claim 1 wherein the compound is one selected from the group consisting of compounds of formulae (IID),(IIF), (IIW), and (IIY):

(IID)

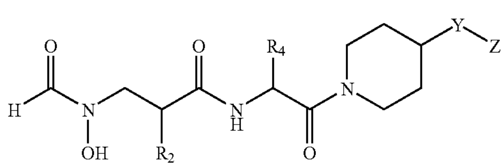

(IIF)

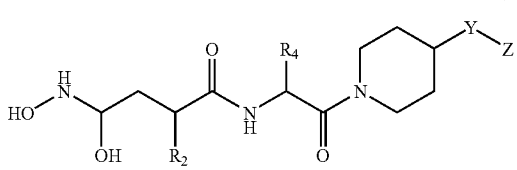

-continued (IIW)

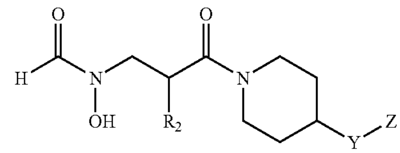

(IIY)

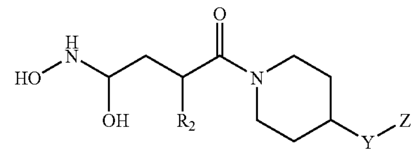

wherein $R_2$ is n-propyl, n-butyl, n-pentyl, cyclopentylmethyl, cyclopentylethyl, cyclohexylmethyl or cyclohexyl-ethyl;

$R_4$ is tert-butyl, iso-butyl, benzyl or methyl;

Y is —$CH_2$—, —O— or —(C═O)—; and

Z is a phenyl, 3,4-methylenedioxyphenyl, morpholinyl, pyrimidin-2-yl, 1,2,3-thiadiazol-5-yl, 1 ,4-thiazol-5-yl, benzofuran-2-yl, 2 or 3-furanyl, 2- or 3-thienyl, 2- or 3-pyranyl, 2-, 3- or 4-pyrrolyl, 3-, 4-or 5-pyazolyl, 3-, 4-or 5-isoxazolyl, or 2-, 3-or 4-pyridyl ring which may optionally be substituted.

13. A method for the treatment of bacterial infections in humans and non-human mammals, which comprises administering to a subject suffering such infection an antibacterially effective dose of a compound as claimed in claim 1.

14. A method for the treatment of bacterial contamination by applying an antibacterially effective amount of a compound as claimed in claim 1 to the site of contamination.

15. A pharmaceutical or veterinary composition comprising a compound as claimed in claim 1 together with a pharmaceutically or veterinarily acceptable carrier.

16. A method for the treatment of bacterial infections in humans and non-human mammals, which comprises administering to a subject suffering such infection an antibacterially effective dose of a compound as claimed in claim 12.

17. A method for the treatment of bacterial contamination by applying an antibacterially effective amount of a compound as claimed in claim 12 to the site of contamination.

18. A pharmaceutical or veterinary composition comprising a compound as claimed in claim 12 together with a pharmaceutically or veterinarily acceptable carrier.

* * * * *